(12) United States Patent
Heuer

(10) Patent No.: US 10,363,249 B2
(45) Date of Patent: Jul. 30, 2019

US010363249B2

(54) FATTY ACID SYNTHASE INHIBITOR FOR USE IN THE TREATMENT OF DRUG RESISTANT CANCER

(71) Applicant: 3-V Biosciences, Inc., Menlo Park, CA (US)

(72) Inventor: Timothy Sean Heuer, Menlo Park, CA (US)

(73) Assignee: 3-V Biosciences, Inc., San Mateo, CA (US)

( * ) Notice: Subject to any disclaimer, the term of this patent is extended or adjusted under 35 U.S.C. 154(b) by 28 days.

(21) Appl. No.: 15/503,809

(22) PCT Filed: Aug. 14, 2015

(86) PCT No.: PCT/US2015/045244
§ 371 (c)(1),
(2) Date: Feb. 14, 2017

(87) PCT Pub. No.: WO2016/025816
PCT Pub. Date: Feb. 18, 2016

(65) Prior Publication Data
US 2017/0273964 A1 Sep. 28, 2017

Related U.S. Application Data

(60) Provisional application No. 62/038,113, filed on Aug. 15, 2014.

(51) Int. Cl.
| *A61K 31/454* | (2006.01) |
| *A61K 45/06* | (2006.01) |
| *A61K 31/00* | (2006.01) |
| *A61K 31/337* | (2006.01) |
| *A61K 31/4178* | (2006.01) |
| *A61K 47/64* | (2017.01) |
| *A61K 47/69* | (2017.01) |

(52) U.S. Cl.
CPC ............ *A61K 31/454* (2013.01); *A61K 31/00* (2013.01); *A61K 31/337* (2013.01); *A61K 31/4178* (2013.01); *A61K 45/06* (2013.01); *A61K 47/643* (2017.08); *A61K 47/6935* (2017.08)

(58) Field of Classification Search
None
See application file for complete search history.

(56) References Cited

U.S. PATENT DOCUMENTS

| 8,871,790 | B2 | 10/2014 | Oslob et al. |
| 9,428,502 | B2 | 8/2016 | Oslob et al. |
| 9,624,173 | B2 | 4/2017 | Oslob et al. |
| 9,809,591 | B2 | 11/2017 | Oslob et al. |
| 9,994,550 | B2 | 6/2018 | Wagman et al. |
| 2008/0103208 | A1 | 5/2008 | Ossovskaya et al. |
| 2009/0105305 | A1 | 4/2009 | Butlin et al. |
| 2009/0118332 | A1 | 5/2009 | Butlin et al. |
| 2012/0264737 | A1* | 10/2012 | Oslob .................. C07D 405/14 514/210.21 |
| 2013/0287791 | A1 | 10/2013 | Xu et al. |
| 2014/0322355 | A1 | 10/2014 | Oslob et al. |
| 2015/0210688 | A1 | 7/2015 | Oslob et al. |
| 2015/0259292 | A1 | 9/2015 | Oslob et al. |
| 2016/0102091 | A1 | 4/2016 | Oslob et al. |
| 2016/0311803 | A1 | 10/2016 | Oslob et al. |
| 2016/0326141 | A1 | 11/2016 | Wagman et al. |
| 2016/0338998 | A1 | 11/2016 | Heuer et al. |
| 2017/0119786 | A1 | 5/2017 | Buckley et al. |
| 2018/0079746 | A1 | 3/2018 | Oslob et al. |

FOREIGN PATENT DOCUMENTS

| WO | WO-2007/063012 A1 | 6/2007 |
| WO | WO-2008/059214 A1 | 5/2008 |
| WO | WO-2008/075064 A1 | 6/2008 |
| WO | WO-2008/075077 A1 | 6/2008 |
| WO | 2012/122391 * | 9/2012 |
| WO | WO 2012/122391 A1 | 9/2012 |
| WO | WO 2014/008197 A1 | 1/2014 |
| WO | WO-2014/008197 A1 | 1/2014 |
| WO | WO 2015/095767 A1 | 6/2015 |
| WO | WO 2015/105860 A1 | 7/2015 |
| WO | WO-2016/025816 A1 | 2/2016 |
| WO | WO-2016/149271 A1 | 9/2016 |

OTHER PUBLICATIONS

Brunton, LL; Gilman, A; Goodman, LS. Goodman & Gilman's Manual of Pharmacology and Therapeutics, New York : McGraw-Hill Professional, 2008. (McGraw Hill Professional). ISBN: 9780071443432, pp. 844-861 (Year: 2008).*
Brunton, LL; Gilman, A; Goodman, LS. Goodman & Gilman's Manual of Pharmacology and Therapeutics, New York : McGraw-Hill Professional, 2008. (McGraw Hill Professional). ISBN: 9780071443432, pp. 883-884 (Year: 2008).*
Di Costanzo, F. et al. "Targeted delivery of albumin bound paclitaxel in the treatment of advanced breast cancer", Oncotargets and Therapy, 2009, p. 179.
Flavin, R. et al. "Fatty acid synthase as a potential therapeutic target in cancer", Future Oncology, vol. 6, No. 4, 2010, p. 551-562.
Lupu, R. et al. "Pharmacological inhibitors of fatty acid synthase (FASN)-catalyzed endogenous fatty acid biogenesis: A new family of anti-cancer agents?", Current Pharmaceutical Biotechnology, vol . 7, No. 6, 2006, p. 483-494.
Meena, A. et al. "Inherent and Acquired Resistance to Paclitaxel in Hepatocellular Carcinoma: Molecular Events Involved", PLoS One, vol. 8, No. 4, 2013, p. e61524.

(Continued)

*Primary Examiner* — Karl J Puttlitz
(74) *Attorney, Agent, or Firm* — Cooley LLP

(57) ABSTRACT

Compounds that are fatty acid synthesis modulators are provided. The compounds may be used in pharmaceutical compositions to treat taxane-resistant cancers. Methods are provided for treating taxane-resistant cancer in a subject. Methods are also provided for increasing the sensitivity of a cancer cell to taxanes (i.e., paclitaxel, Nab-paclitaxel docetaxel, and/or cabazitaxel) treatment.

20 Claims, No Drawings

(56) References Cited

OTHER PUBLICATIONS

Menendez, J. et al. "Pharmacological and small interference RNA-mediated inhibition of breast cancer-associated fatty acid synthase (oncogenic antigen-519) synergistically enhances Taxol (paclitaxel)-induced cytotoxicity", International Journal of Cancer, 2005, vol. 115, No. 1, p. 19-35.
Ueda, S. et al. "Expression of Fatty Acid Synthase Depends on NAC1 and Is Associated with Recurrent Ovarian Serous Carcinomas" Journal of Oncology, 2010, 12 pages, Article ID 285191.
Vazquez, M. et al. "Discovery of GSK837149A, an inhibitor of human fatty acid synthase targeting the [beta]-ketoacyl reductase reaction", FEBS Journal, vol. 275, No. 7, 2008, pp. 1556-1567.
Acton, Q. Ashton, "Multiple Myeloma: New Insights for the Healthcare Professional", 2013 Edition, p. 71.
Appel and Llinas, "Combination Therapy", http.//www.healthcommunities.com/high-blood-pressure/combination-therapy_lhmwp.shtml, 2013, 1 page.
Bentzien et al., "Pyrrolidinyl and piperidinyl compounds useful as NHE-1 inhibitors and their preparation and pharmaceutical compositions," *CAPLUS* 152:144485, 2010.
Colombo et al., "Novel Platforms for Oral Drug Delivery", *Pharmaceutical Research* (2009), 26(3):601-611.
Cui, "Preparation of aminoheteroaryl compounds as protein kinase inhibitors," *CAPLUS* 141:260769, 2004.
Improper Markush Fed. Registry, vol. 76(27) p. 7162-75, slide 1, 64-67 (2011).
Knust et al., "Preparation of piperidine derivatives as NK-3 receptor antagonists," *CAPLUS* 153:456481, 2010.
Menet et al., "Novel triazolopyridine compounds as JAK kinase inhibitors useful for the treatment of degenerative and inflammatory diseases and their preparation," *CAPLUS* 152:192130, 2010.
Rodon et al., "Combining Targeted Therapies: Practical Issues to Consider at the Bench and Bedside", *The Oncologist* (2010), 15:37-50.
Schneider et al., "Preparation of 5-alkynyl-pyrimidines as kinase inhibitors," *CAPLUS* 155:271283, 2011.
Teicher and Andrews. *Anticancer Drug Development Guide*, second edition, Humana Press, Chapter 1 (2004).
Shah, U. S. et al. "Inhibition of fatty acid synthase (FAS) increases cell toxicity in androgen independent prostate Cancer cells in conjunction with paclitaxel and docetaxel treatment", *Cancer Research, Proc Amer Assoc Cancer Res*. Apr. 2006. 47. Retrieved from the Internet<http://cancerres.aacrjournals.org/content/66/8_Supplement/639.4>.

* cited by examiner

FATTY ACID SYNTHASE INHIBITOR FOR USE IN THE TREATMENT OF DRUG RESISTANT CANCER

RELATED APPLICATIONS

This application is a U.S. National Phase application, filed under 35 U.S.C. § 371(c), of International Application No. PCT/US2015/045244, filed Aug. 14, 2015, which claims the benefit of and priority to U.S. provisional application No. 62/038,113, filed Aug. 15, 2014, the entire contents of each of which are incorporated herein by reference in their entireties.

FIELD

The present disclosure relates generally to modulators of lipid synthesis, e.g., fatty acid synthase inhibitors, and methods of use thereof. The present modulators of lipid synthesis can be used for the treatment of paclitaxel-resistant cancers. The present modulators of lipid synthesis can also be used to increase the sensitivity of a cancer to treatment with paclitaxel or Nab-paclitaxel.

BACKGROUND

The dominant therapeutic approaches that are currently employed to treat cancer include surgical removal of primary tumors, tumor irradiation, and parenteral application of anti-mitotic cytotoxic agents. The continued dominance of long established therapies is mirrored by the lack of improvement in survival rates for most cancers. Surgical intervention often results in a release of tumor cells into the circulation or lymph systems from which metastatic tumors can subsequently be established.

Resistance of tumor cells to chemotherapeutic drugs is an important problem in the clinical management of cancer. Paclitaxel is an anti-mitotic cytotoxic agent that has provided improvement in patient outcomes. Unfortunately, despite this success, many patients will eventually progress to a phase of the disease that becomes resistant or unresponsive to treatment with paclitaxel and other traditional chemotherapeutic drugs.

The compounds useful in the present invention have been disclosed as inhibitors of fatty acid synthesis in U.S. Publication No. 2012/0264737, International PCT Publication No. WO 2015/105860, and International PCT Publication No. WO 2014/008197, which are incorporated herein by reference in their entirety. Surprisingly, the compounds of the present disclosure have been found to be useful to resensitize paclitaxel-resistant cancers to treatment with paclitaxel or Nab-paclitaxel.

BRIEF SUMMARY

In brief, the present invention is directed to fatty acid synthase inhibitors and methods of use thereof. Fatty acid synthase inhibitors can be used for the treatment of paclitaxel-resistant cancers. Fatty acid synthase inhibitors can also be used to increase the sensitivity of a cancer to taxanes such as paclitaxel, Nab-paclitaxel, docetaxel, and cabazitaxel.

In one embodiment, the methods and compositions described herein are useful for treating a paclitaxel-resistant tumor or cancer in a subject, the method comprising administering to the subject in need thereof, a therapeutically effective amount of a fatty acid synthase inhibitor and a therapeutically effective amount of paclitaxel or Nab-paclitaxel.

In particular embodiments, a method for treating a paclitaxel-resistant cancer in a subject is provided, the method comprising:

(a) determining that the subject is paclitaxel-resistant or has a paclitaxel-resistant tumor or cancer, and (b) administering to the subject in need thereof, a therapeutically effective amount of a fatty acid synthase inhibitor and a therapeutically effective amount of paclitaxel or Nab-paclitaxel.

In one embodiment, the methods and compositions described herein are useful for treating or preventing a tumor or cancer in a subject in need thereof, the method comprising administering to the subject in need thereof, a therapeutically effective amount of a fatty acid synthase inhibitor and a therapeutically effective amount of paclitaxel or Nab-paclitaxel.

In particular embodiments, the methods and compositions described herein are useful for enhancing the activity of paclitaxel or Nab-paclitaxel in treating a tumor or a cancer, the method comprising administering to a subject in need thereof, a therapeutically effective amount of a fatty acid synthase inhibitor and a therapeutically effective amount of paclitaxel or Nab-paclitaxel.

In various embodiments, the methods and compositions described herein are useful for increasing the sensitivity of a tumor or cancer cell to paclitaxel or Nab-paclitaxel, the method comprising administering to a subject in need thereof, a therapeutically effective amount of a fatty acid synthase inhibitor and a therapeutically effective amount of paclitaxel or Nab-paclitaxel.

In particular embodiments, the fatty acid synthase inhibitor described herein is a compound having the structure of:

(a) Formula (I):

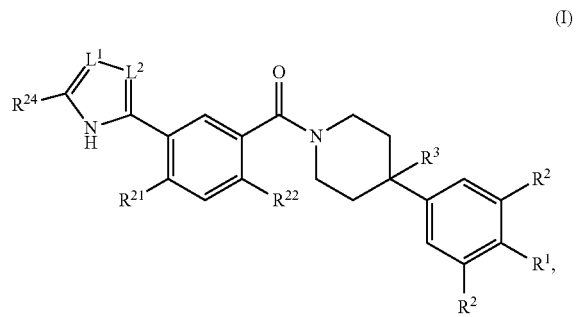

or (b) Formula (II):

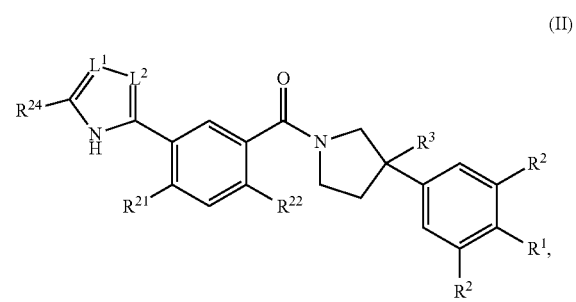

or (c) Formula (III):

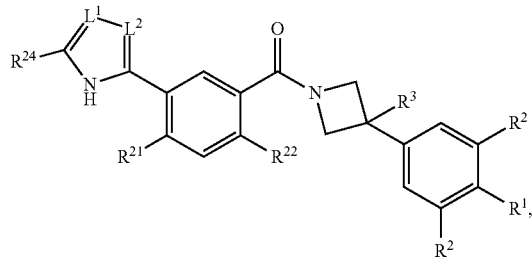

or a pharmaceutically acceptable salt thereof,
wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:
t is 0 or 1;
the $C_3$-$C_5$ cycloalkyl optionally includes an oxygen or nitrogen heteroatom;
$L^1$ is $CR^{23}$ or N;
$L^2$ is $CR^{23}$ or N;
at least one of $L^1$ or $L^2$ is N; and
$R^{23}$ is H or $C_1$-$C_4$ straight or branched alkyl.

In various aspects, pharmaceutical compositions are provided which comprise:
(i) a compound of Formula (I):

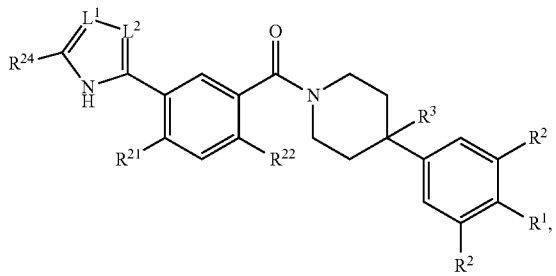

or a pharmaceutically acceptable salt thereof,
wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is independently, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:
t is 0 or 1;
the $C_3$-$C_5$ cycloalkyl optionally includes an oxygen or nitrogen heteroatom;
$L^1$ is $CR^2$ or N;
$L^2$ is CH or N;
at least one of $L^1$ or $L^2$ is N; and
$R^{23}$ is H or $C_1$-$C_4$ straight or branched alkyl; and
(ii) Nab-paclitaxel.

In particular embodiments, the fatty acid synthase inhibitor is one or more compounds, forms, and/or agents that act as an inhibitor of FASN gene expression or FASN protein activity. The fatty acid synthase inhibitor can be selected from cerulenin, 4-Methylene-2-octyl-5-oxotetrahydrofuran-3-carboxylic acid (C75), orlistat, C93 (FAS93), FAS31, C247, GSK837149A ((4,4'-(carbonylbis(azanediyl))bis(N-(4-methylpyrimidin-2-yl)benzenesulfonamide)), platensimycin, (−)-epigallocatechin-3-gallate (EGCG), luteolin, taxifolin, kaempferol, quercetin, apigenin, catchin, soy protein, and oleic acid, or the like.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_{1-12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1, 1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$, —$(CH_2CH_2O)_{2-10}R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. The above non-hydrogen groups are generally referred to herein as "substituents". In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see. Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a subject for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Subject" or "patient" includes mammals, which includes humans and both domestic animals such as laboratory animals and household pets (e.g., cats, dogs, swine, cattle, sheep, goats, horses, rabbits), and non-domestic animals such as wildlife and the like. Accordingly, the term "subject" or "patient" as used herein means any mammalian patient or subject to which the compounds of the invention can be administered. In an exemplary aspect of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that are associated with the targeted or suspected disease or condition. These and other routine methods allow the clinician to select patients in need of therapy using the methods and formulations of the present invention.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

"Effective amount" or "therapeutically effective amount" refers to that amount of a compound of the invention which, when administered to a subject, preferably a human, is sufficient to treat a paclitaxel-resistant cancer, or to re-sensitize a paclitaxel-resistant cancer to treatment with paclitaxel or Nab-paclitaxel. The amount of a compound of the invention which constitutes a "therapeutically effective amount" will vary depending on the compound, the condition and its severity, the manner of administration, and the age or weight of the subject to be treated, but can be determined routinely by one of ordinary skill in the art having regard to his own knowledge and to this disclosure.

"Treating" or "treatment" as used herein covers the treatment of the disease or condition of interest in a subject, preferably a human, having the disease or condition of interest, and includes:

(i) preventing the disease or condition from occurring in a subject, in particular, when such subject is predisposed to the condition but has not yet been diagnosed as having it, or when a subject has had the disease and reoccurrence is possible or likely;

(ii) inhibiting the disease or condition, i.e., arresting its development;

(iii) relieving the disease or condition, i.e., causing regression of the disease or condition;

(iv) relieving the symptoms resulting from the disease or condition, i.e., relieving pain or side effects without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians; or (v) resensitization of disease cells to treatment with a compound to which the disease is resistant or refractory.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposeable mirror images of one another.

A "tautomer" refers to a proton shift from one atom of a molecule to another atom of the same molecule. The present invention includes tautomers of any said compounds.

"Paclitaxel" refers to paclitaxel and all various form or derivatives thereof, e.g., nanoparticle albumin-bound paclitaxel ("Nab-paclitaxel").

"Paclitaxel-resistant" refers to a tumor, a cancerous cell, or a patient diagnosed with cancer that has intrinsic or acquired resistance to the chemotherapeutic effect of paclitaxel. This includes, without limitation, tumors or cancers that were once responsive to paclitaxel but have become refractory or unresponsive to treatment with paclitaxel.

"Docetaxel-resistant" refers to a tumor, a cancerous cell, or a patient diagnosed with cancer that has intrinsic or acquired resistance to the chemotherapeutic effect of docetaxel. This includes, without limitation, tumors or cancers that were once responsive to docetaxel but have become refractory or unresponsive to treatment with paclitaxel.

"Cabazitaxel-resistant" refers to a tumor, a cancerous cell, or a patient diagnosed with cancer that has intrinsic or acquired resistance to the chemotherapeutic effect of cabazitaxel. This includes, without limitation, tumors or cancers that were once responsive to cabazitaxel but have become refractory or unresponsive to treatment with cabazitaxel.

"Taxane-resistant" refers to a tumor, a cancerous cell, or a patient diagnosed with cancer that has intrinsic or acquired resistance to the chemotherapeutic effect of a taxane. This includes, without limitation, tumors or cancers that were once responsive to a taxane but have become refractory or unresponsive to treatment with taxane.

Pharmaceutical Combination and Treatment Regimes

In the case of a treatment-regime, a compound of the invention, or pharmaceutically acceptable derivatives thereof, may be administered simultaneously with, prior to, or after administration of any other compound of the invention. Compounds of the invention, or pharmaceutically acceptable derivatives thereof, may also be administered simultaneously with, prior to, or after administration of one or more other therapeutic agents. Such combination therapies include administration of a single pharmaceutical dosage formulation which contains one or more compounds of the invention, as well as administration of one compound of the invention and another compound of the invention in their own separate pharmaceutical dosage formulation. For example, the compounds of the invention can be administered to the patient together in a single dosage formulation such as a tablet, capsule or injection, or each agent administered in separate dosage formulations. In addition, the compounds of the invention may be administered to the patient via any of the accepted modes of administration of agents for serving similar utilities. Where separate dosage formulations are used, the compounds of the invention (and as applicable, any additional active agents) can be administered at essentially the same time, i.e., concurrently, or at separately staggered times, i.e., sequentially. Combination therapy is understood to include all these treatment regimens.

In certain embodiments, the additional therapeutically active agent included in a pharmaceutical combination or treatment regime of the invention is selected, for example, from paclitaxel and Nab-paclitaxel.

In various aspects, pharmaceutical compositions are provided which comprise:
(i) a compound of Formula (I):

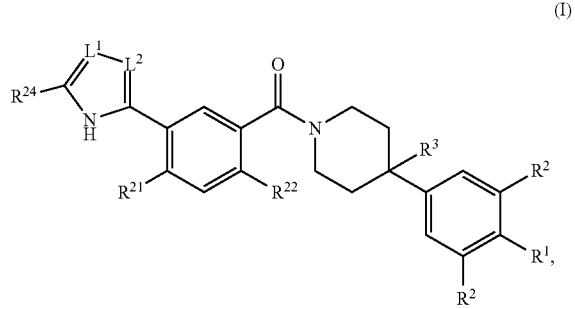

or a pharmaceutically acceptable salt thereof,
wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is $CR^{23}$ or N;

$L^2$ is CH or N;

at least one of $L^1$ or $L^2$ is N; and $R^{23}$ is H or $C_1$-$C_4$ straight or branched alkyl; and (ii) Nab-paclitaxcel.

In some aspects of Formula (I), $R^{24}$ is $C_1$-$C_4$ straight or branched alkyl, —($C_1$-$C_4$ alkyl)$_t$-O—($C_1$-$C_4$ straight or branched alkyl) wherein t is 0 or 1.

In some aspects of Formula (I), $R^{21}$ is halogen, $C_1$-$C_4$ straight or branched alkyl, $C_3$-$C_5$ cycloalkyl wherein the $C_3$-$C_5$ cycloalkyl optionally includes an oxygen or nitrogen heteroatom, —S(O)$_u$—($C_1$-$C_4$ straight or branched alkyl) wherein u is 0 or 2, or —S(O)$_u$—($C_3$-$C_5$ cycloalkyl) wherein u is 0 or 2;

In some aspects of Formula (I), $R^3$ is H or halogen.

In some aspects of Formula (I), $R^1$ is halogen, —CN or $C_1$-$C_2$ haloalkyl.

In some aspects of Formula (I), both $L^1$ and $L^2$ are N.

In some aspects of Formula (I), $R^{21}$ is $C_1$-$C_2$ alkyl or $C_3$-$C_5$ cycloalkyl and $R^{22}$ is $C_1$-$C_2$ alkyl.

In some aspects of Formula (I), $R^{21}$ is $C_3$-$C_5$ cycloalkyl and $R^{22}$ is $C_1$-$C_2$ alkyl.

In some aspects of Formula (I), $R^{24}$ is —($C_1$-$C_2$ alkyl)$_t$-O—($C_1$-$C_2$ alkyl) wherein t is 0 or 1.

In some aspects of Formula (I), $R^{21}$ is $C_3$-$C_5$ cycloalkyl, $R^{22}$ is $C_1$-$C_2$ alkyl and $R^{24}$ is $C_1$-$C_2$ alkyl.

In some aspects of Formula (I), $R^{21}$ is cyclobutyl, $R^{22}$ is $C_1$-$C_2$ alkyl and $R^{24}$ is $C_1$-$C_2$ alkyl.

In some aspects of Formula (I), $R^{21}$ is cyclobutyl.

In some aspects of Formula (I), $R^3$ is H or F.

In some aspects of Formula (I), $R^1$ is —CN.

In some aspects of Formula (I), $R^1$ is —CF$_3$.

In some aspects of Formula (I), $R^{22}$ is H, methyl or ethyl.

In some aspects of Formula (I), $R^{22}$ is H.

In some aspects of Formula (I), $R^{22}$ is methyl.

In some aspects of Formula (I), $R^1$ is —CN, each $R^2$ is hydrogen, $R^3$ is H or F, $R^{21}$ is $C_3$-$C_4$ cycloalkyl, $R^{22}$ is methyl, $L^1$ and $L^2$ are N, and $R^{24}$ is methyl, ethyl, hydroxymethyl, methoxymethyl, 2-methoxyethyl.

In some aspects of Formula (I), $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methoxy or ethoxy.

In some aspects of Formula (I), $R^1$ is —CN, each $R^2$ is H, $R^3$ is H or F, $R^{21}$ is $C_3$-$C_4$ cycloalkyl, $R^{22}$ is methyl, $L^1$ is CH, $L^2$ is N, and $R^{24}$ is methyl, ethyl, hydroxymethyl, methoxymethyl, or 2-methoxyethyl.

In some aspects of Formula (I), $R^1$ is —CN, each $R^2$ is H, $R^3$ is H or F, $R^{21}$ is $C_3$-$C_4$ cycloalkyl, $R^{22}$ is methyl, $L^1$ is N, $L^2$ is CH, and $R^{24}$ is methyl, ethyl, hydroxymethyl, methoxymethyl, or 2-methoxyethyl.

In particular embodiments, the compound of Formula (I) is:

In particular embodiments, the compound of Formula (I) is:

In particular embodiments, the compound of Formula (I) is:

In particular embodiments, the compound of Formula (I) is:

In other aspects, pharmaceutical compositions are provided which comprise: (i) a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, and (ii) a taxane.

In other aspects, pharmaceutical compositions are provided which comprise: (i) a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, and (ii) paclitaxel.

In other aspects, pharmaceutical compositions are provided which comprise: (i) a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, and (ii) Nab-paclitaxel.

In other aspects, pharmaceutical compositions are provided which comprise: (i) a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, and (ii) docetaxel.

In other aspects, pharmaceutical compositions are provided which comprise: (i) a compound of Formula (I), (II), (III), (IV), (V), (VI), (VII), (VIII), (IX), (X) (XI), (XII), (XIII), (XIV), (XV), (XVI), (XVII), (XVII), (XIX), (XX), (XXI), (XXIII), (XXIII), (XXIV), (XXV), (XXVI), (XXVII), (XXVIII), or (XXIX), or a pharmaceutically acceptable salt thereof, and (ii) cabazitaxel.

It is understood that in the present description, combinations of substituents and/or variables of the depicted formula are permissible only if such contributions result in stable compounds.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

Method of Treatment

As described above, fatty acid synthase inhibitors can also be used to increase the sensitivity of a cancer to taxanes such as paclitaxel, Nab-paclitaxel, docetaxel, and cabazitaxel. In some embodiments, the methods and compositions described herein are useful for treating a taxane-resistant tumor or cancer in a subject, the method comprising administering to the subject in need thereof, a therapeutically effective amount of a fatty acid synthase inhibitor and a therapeutically effective amount of a taxane.

One aspect of the present invention relates to a method of treating or preventing a taxane-resistant tumor or cancer in a subject in need thereof, the method comprising administering to the subject a fatty acid synthase inhibitor compound having the structure of:

(a) Formula (I):

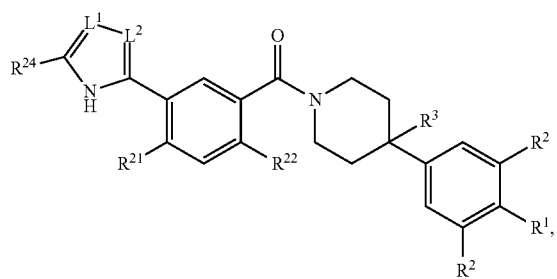

(I)

or (b) Formula (II):

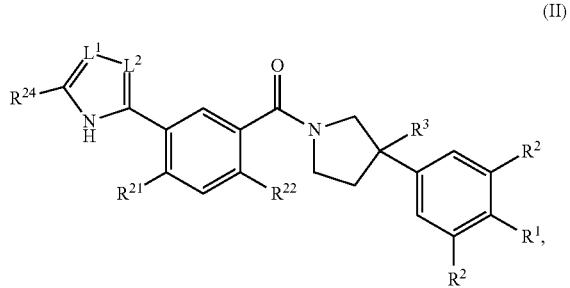

(II)

or (c) Formula (III):

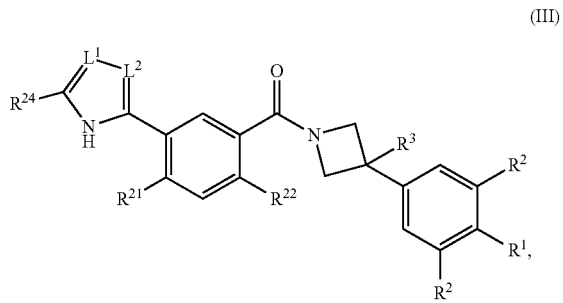

(III)

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: the $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is $CR^{23}$ or N;

$L^2$ is $CR^{23}$ or N;

at least one of $L^1$ or $L^2$ is N; and $R^{23}$ is H or $C_1$-$C_4$ straight or branched alkyl;

or (d) Formula (IV):

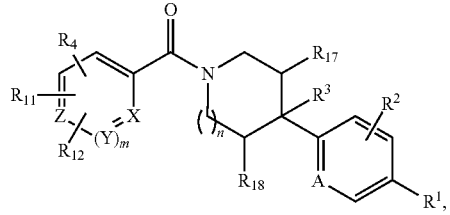

(IV)

or a pharmaceutical acceptable salt thereof,
wherein:

X, Y, and Z are each independently CR or NR', wherein R is hydrogen or $C_{1-6}$ alkyl and R' is hydrogen, $C_{1-6}$ alkyl, or absent;

A is CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$ $R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{15}$ and $R_{16}$ are each independently hydrogen, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

n is 1 or 2; and m is 0 or 1;

or (e) Formula (V):

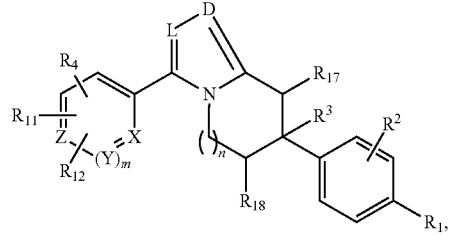

(V)

or a pharmaceutically acceptable salt thereof,
wherein:

X, Y, and Z are each independently CR or NR', wherein R is hydrogen or $C_{1-6}$ alkyl and R' is hydrogen, $C_{1-6}$ alkyl, or absent;

L and D are each independently C or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, \—N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$ $R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{15}$ and $R_{16}$ are each independently hydrogen, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

n is 1 or 2; and m is 0 or 1;

or (f) Formula (VI):

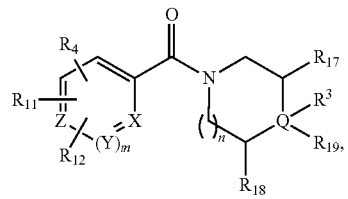

(VI)

or a pharmaceutically acceptable salt thereof, wherein:
X, Y, and Z are each independently CR or NR', wherein R is hydrogen or $C_{1-6}$ alkyl and R' is hydrogen, $C_{1-6}$ alkyl, or absent;
Q is C or N;
$R_3$ is hydrogen, hydroxyl, halo, $C_{1-6}$ alkyl, $C_{1-6}$ alkoxy, or if Q is N then $R_3$ is absent;
$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;
$R^{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;
$R_{12}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_{11}$ and $R_{12}$ taken together with the atoms to which they are attached join together to form a heteroaryl;
$R_{20}$ is hydrogen or $C_{1-6}$ alkyl, $C_{1-6}$ alkoxy, or —N($R_{13}$)($R_{14}$);
$R_5$, $R_6$, $R_7$, $R_8$, $R_9$ $R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2R_{20}$;
$R_{15}$ and $R_{16}$ are each independently hydrogen, $C_{1-6}$ alkyl, cycloalkyl, aryl, heterocyclyl, heteroaryl, or alkylamino;
$R_{17}$ and $R_{18}$ are each independently hydrogen or alkyl or can optionally join together to form a bond;
$R_{19}$ is aryl, heteroaryl, cycloalkyl, or heterocyclyl;
n is 0, 1, or 2; and
m is 0 or 1;
or
(g) Formula (VII):

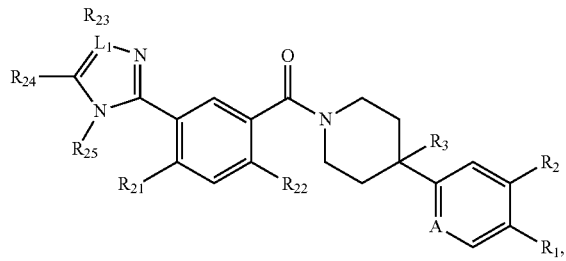

(VII)

or,
(h) Formula (VIII):

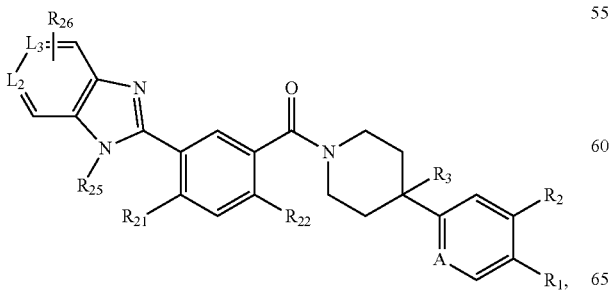

(VIII)

or,
(i) Formula (IX):

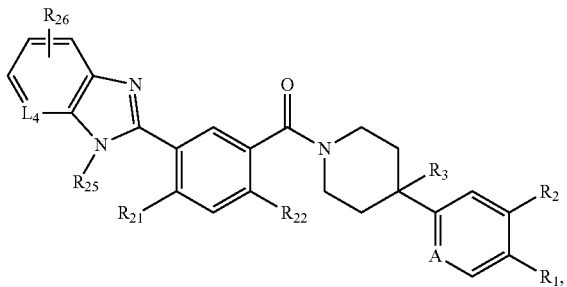

(IX)

or a pharmaceutically acceptable salt thereof,
wherein:
$L_1$, $L_2$, $L_3$, $L_4$, and A are each independently CH or N;
$R_1$ is hydrogen, cyano, halo, $C_{1-6}$ alkyl, $C_{1-6}$ alkoxy, —C(=O)N($R_{13}$)($R_{14}$), —($CH_2$)C(=O)N($R_{13}$)($R_{14}$), $CF_3$, —$OCF_3$, or —S(=O)$_2R_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, $CF_3$, —$OCF_3$, or —S(=O)$_2R_{20}$;
$R_{23}$ is hydrogen, —N($R_{13}$)($R_{14}$), $C_{1-6}$ alkyl, $C_{1-6}$ alkoxy, is absent if $L_1$ is N, or $R_{23}$ and $R_{24}$ taken together with the atoms to which they are attached join together to form a heterocyclyl, heteroaryl, or cycloalkyl;
$R_{24}$ is hydrogen, —N($R_{13}$)($R_{14}$), $C_{1-6}$ alkyl, $C_{1-6}$ alkoxy, —($C_{1-6}$ alkoxy)(heterocyclyl), heterocyclyl, or $R_{23}$ and $R_{24}$ taken together with the atoms to which they are attached join together to form a heterocyclyl, heteroaryl, or cycloalkyl;
$R_{26}$ is hydrogen, heteroaryl, heterocyclyl, —N($R_{13}$)($R_{14}$), or —S(=O)$_2R_{20}$;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2R_{20}$;
$R_{25}$ is hydrogen, $C_{1-6}$ alkyl, or $C_{1-6}$ alkoxy; and
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino;
or
(j) Formula (X):

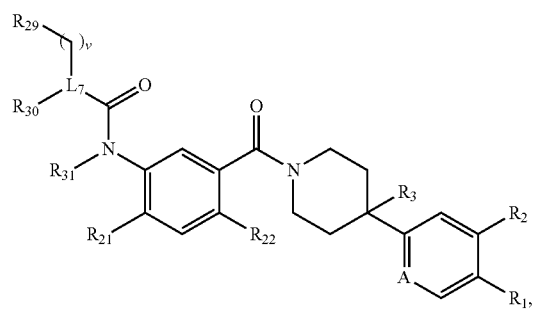

(X)

or a pharmaceutically acceptable salt thereof, wherein:
L$_7$ is N or O, wherein R$_{30}$ is absent if L$_7$ is O;
A is CH or N;
R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;
q is 0, 1, 2, 3, or 4;
R$_{20}$ is hydrogen or C$_{1-6}$ alkyl, C$_{1-6}$alkoxy, or —N(R$_{13}$)(R$_{14}$);
R$_2$ is hydrogen, halo, C$_{1-6}$ alkoxy, or C$_{1-6}$ alkyl;
R$_3$ is halo, C$_{1-6}$ alkyl, or C$_{1-6}$ alkoxy;
R$_{21}$ and R$_{22}$ are each independently hydrogen, halo, cyano, C$_{1-6}$ alkyl, C$_{1-6}$ alkoxy, CF$_3$, —OCF$_3$, or —S(=O)$_2$R$_{20}$;
R$_{29}$ and R$_{30}$ are each independently hydrogen, C$_{1-6}$ alkyl, C$_{1-6}$ alkoxy, hydroxyalkyl, heteroaryl, heterocyclyl, —N(R$_{15}$R$_{16}$), —C(=O)R$_{46}$, —R$_{48}$C(=O)R$_{47}$, or R$_{29}$ and R$_{30}$ taken together with the atoms to which they are attached join together to form a heteroaryl or heterocyclyl, wherein R$_{30}$ is absent if L$_7$ is O;
R$_{46}$ and R$_{47}$ are each independently hydrogen, C$_{1-6}$ alkyl, cycloalkyl, aryl, heterocyclyl, heteroaryl, hydroxyalkyl, —N(R$_{15}$R$_{16}$), or —S(=O)$_2$R$_{20}$;
R$_{48}$ is alkyl or is absent;
R$_{31}$ is hydrogen, C$_{1-6}$ alkyl, or C$_{1-6}$ alkoxy;
R$_{13}$ and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;
R$_{15}$ and R$_{16}$ are each independently hydrogen, C$_{1-6}$ alkyl, cycloalkyl, aryl, heterocyclyl, heteroaryl, hydroxyalkyl, or alkylamino; and
v is 0 or 1;
or
(k) Formula (XI):

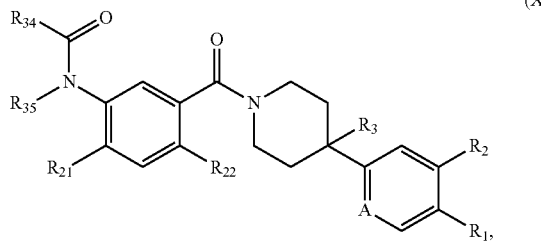

or
(l) Formula (XII):

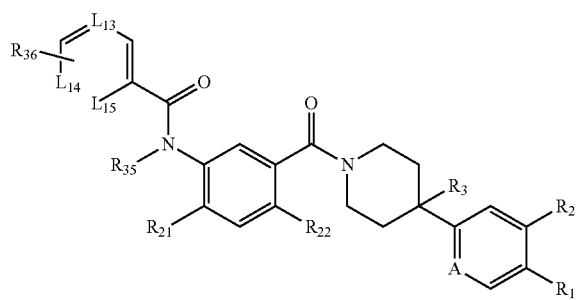

or a pharmaceutically acceptable salt thereof, wherein:
L$_{13}$, L$_{14}$, L$_{15}$, and A are each independently CH or N;
R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;
q is 0, 1, 2, 3, or 4;
R$_{20}$ is hydrogen or C$_{1-6}$ alkyl, C$_{1-6}$ alkoxy, or —N(R$_{13}$)(R$_{14}$);
R$_2$ is hydrogen, halo, C$_{1-6}$ alkoxy, or C$_{1-6}$ alkyl;
R$_3$ is halo, C$_{1-6}$ alkyl, or C$_{1-6}$ alkoxy;
R$_{21}$ and R$_{22}$ are each independently hydrogen, halo, cyano, C$_{1-6}$ alkyl, C$_{1-6}$ alkoxy, CF$_3$, —OCF$_3$, or —S(=O)$_2$R$_{20}$;
R$_{34}$ is hydrogen, C$_{1-6}$ alkyl, C$_{1-6}$ alkoxy, cycloalkyl, hydroxyl, hydroxyalkyl, aryl, heterocyclyl, heteroaryl, alkylamino, CF$_3$, —OCF$_3$, —S(=O)$_2$R$_{20}$, or —N(R$_{15}$R$_{16}$);
R$_{35}$ is hydrogen, C$_{1-6}$ alkyl, or C$_{1-6}$ alkoxy;
R$_{36}$ is hydrogen, C$_{1-6}$ alkyl, C$_{1-6}$ alkoxy, —N(R$_{15}$R$_{16}$), heterocyclyl, or heteroaryl;
R$_{13}$ and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$; and
R$_{15}$ and R$_{16}$ are each independently hydrogen, C$_{1-6}$ alkyl, C$_{1-6}$ alkoxy.
cycloalkyl, aryl, heterocyclyl, heteroaryl, hydroxyalkyl, or alkylamino;
or
(m) Formula (XIII):

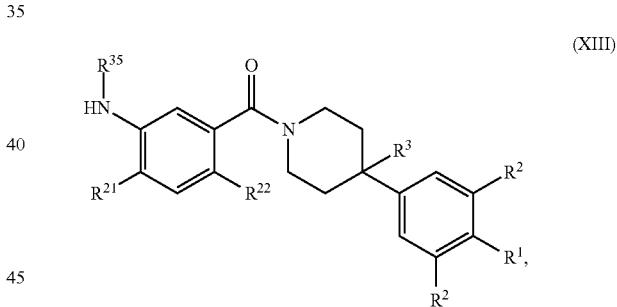

or a pharmaceutically acceptable salt thereof,
wherein:
R$^1$ is H, —CN, halogen, C$_1$-C$_4$ straight or branched alkyl, —O—(C$_3$-C$_5$ cycloalkyl), —O—(C$_1$-C$_4$ straight or branched alkyl) wherein: the C$_3$-C$_5$ cycloalkyl optionally includes an oxygen or nitrogen heteroatom; and when R$^1$ is not H, —CN or halogen, it is optionally substituted with one or more halogens;
each R$^2$ is independently H, halogen or C$_1$-C$_4$ straight or branched alkyl;
R$^3$ is H, —OH, or halogen;
R$^{21}$ is cyclobutyl, azetidin-1-yl, or cyclopropyl;
R$^{22}$ is H, halogen, or C$_1$-C$_2$ alkyl;
R$^{35}$ is —C(O)—R$^{351}$, —C(O)—NHR$^{351}$, —C(O)—O—R$^{351}$ or S(O)$_2$R$^{351}$; and
R$^{351}$ is C$_1$-C$_6$ straight or branched alkyl, cycloalkyl, heterocyclyl, aryl or heteroaryl;

or (n) Formula (XIV):

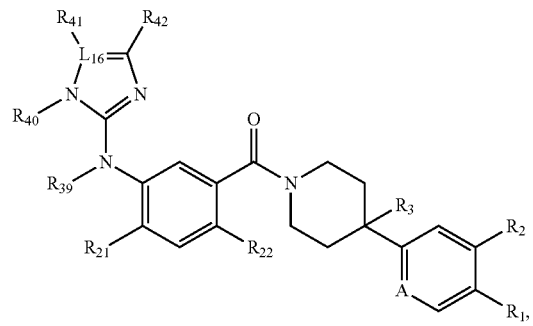

(XIV)

or (o) Formula (XV):

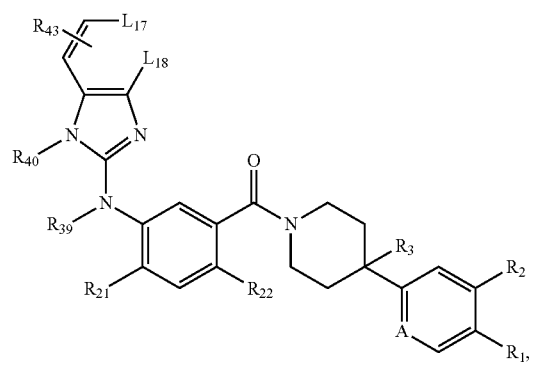

(XV)

or a pharmaceutically acceptable salt thereof,
wherein:
$L_{16}$ is C or N, wherein $R_{41}$ is absent if $L_{16}$ is N.
$L_{17}$, $L_{18}$, and A are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{40}$, $R_{42}$, and $R_{43}$ are each independently hydrogen, $C_{1-6}$ alkyl, $C_{1-6}$ alkoxy, —S(=O)$_2$R$_{20}$, —C(=O)R, hydroxyalkyl, hydroxyl, —N($R_{13}R_{14}$), or $R_{41}$ and $R_{42}$ taken together with the atoms to which they are attached join together to form a heteroaryl or heterocyclyl;
$R_{41}$ is hydrogen, $C_{1-6}$ alkyl, $C_{1-6}$ alkoxy, —S(=O)$_2$R$_{20}$, —C(=O)R, hydroxyalkyl, hydroxyl, —N($R_{13}R_{14}$), $R_{41}$ is absent if $L_{16}$ is N, or $R_{41}$ and $R_{42}$ taken together with the atoms to which they are attached join together to form a heteroaryl or heterocyclyl;
R is hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;

$R_{39}$ is hydrogen, $C_{1-6}$ alkyl, or $C_{1-6}$ alkoxy;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and
$R_{15}$ and $R_{16}$ are each independently hydrogen, $C_{1-6}$ alkyl, cycloalkyl, aryl, heterocyclyl, heteroaryl, hydroxyalkyl, or alkylamino;
or (p) Formula (XVI):

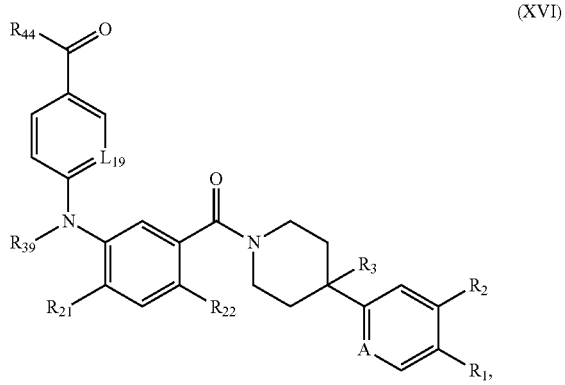

(XVI)

or (q) Formula (XVII):

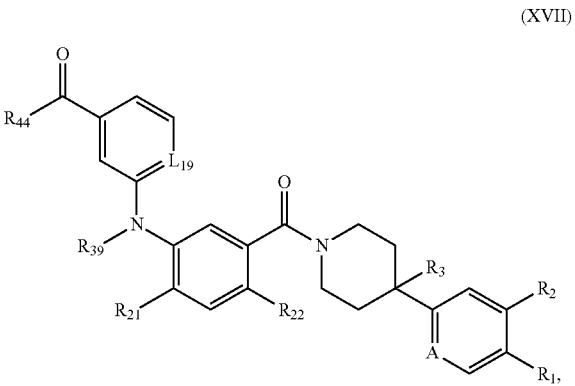

(XVII)

or (r) Formula (XVIII):

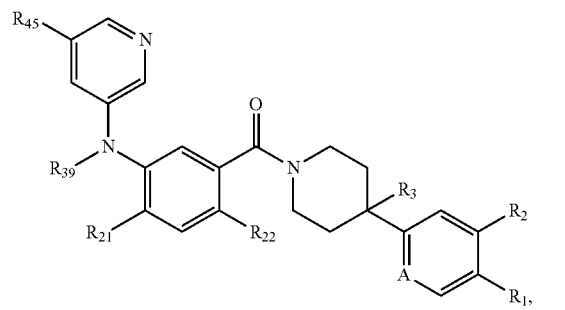

(XVIII)

or a pharmaceutically acceptable salt thereof, wherein:

$L_{19}$ and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{39}$ is hydrogen, $C_{1-6}$ alkyl, or $C_{1-6}$ alkoxy;

$R_{44}$ and $R_{45}$ are each independently hydrogen, $C_{1-6}$ alkyl, $C_{1-6}$ alkoxy, cycloalkyl, hydroxyalkyl, aryl, heterocyclyl, heteroaryl, alkylamino, —S(=O)$_2$R$_{20}$, —C(=O)R, or —N($R_{13}R_{14}$); and $R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino;

or (s) Formula (XIX):

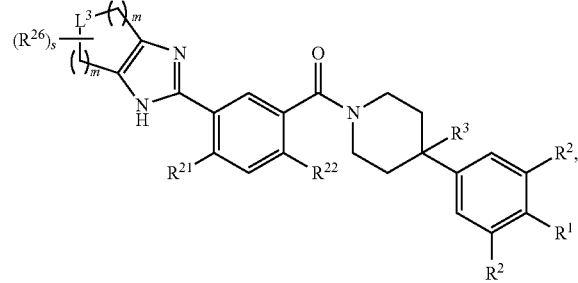

(XIX)

or a pharmaceutically acceptable salt thereof,
wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: the $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH or halogen;

$L^3$ is C($R^{60}$)$_2$, O or NR$^{50}$;

each $R^{60}$ is independently H, —OH, —CN, —O$_t$—($C_3$-$C_5$ cycloalkyl), —O—($C_1$-$C_4$ straight or branched alkyl), or —C(O)—N($R^{601}$)$_2$ wherein:
t is 0 or 1, and
the $C_3$-$C_5$ cycloalkyl optionally includes an oxygen or nitrogen heteroatom;

each $R^{50}$ is independently H, —C(O)—O$_t$—($C_1$-$C_4$ straight or branched alkyl), —C(O)—O$_t$—($C_3$-$C_5$ cyclic alkyl), —$C_3$-$C_5$ cyclic alkyl optionally containing an oxygen or nitrogen heteroatom, —C(O)—N($R^{501}$)$_2$, $C_1$-$C_4$ straight or branched alkyl wherein:
t is 0 or 1, and the $C_3$-$C_5$ cycloalkyl optionally includes an oxygen or nitrogen heteroatom;

n is 1, 2 or 3;

m is 1 or 2;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom $R^{22}$ is H, halogen, $C_1$-$C_2$ alkyl;

each $R^{26}$ is independently —OH, —CN, halogen, $C_1$-$C_4$ straight or branched alkyl, —($C_1$-$C_4$ alkyl)$_t$-O$_t$—($C_3$-$C_5$ cycloalkyl), —($C_1$-$C_4$ alkyl)$_t$-O—($C_1$-$C_4$ straight or branched alkyl), —C(O)—O$_t$—($C_1$-$C_4$ alkyl), or —C(O)—N($R^{501}$)$_2$ wherein:
t is 0 or 1, and
the $C_3$-$C_5$ cycloalkyl optionally includes an oxygen or nitrogen heteroatom;

s is 0, 1 or 2;

each $R^{601}$ and $R^{501}$ is independently H or $C_1$-$C_4$ straight or branched alkyl; and wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$;

or (t) Formula (XX):

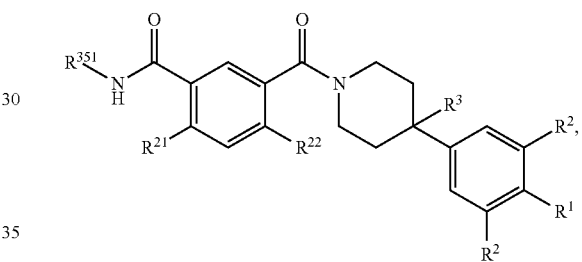

(XX)

or a pharmaceutically acceptable salt thereof,
wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
the $C_3$-$C_5$ cycloalkyl optionally includes an oxygen or nitrogen heteroatom; and
when $R^1$ is not H, —CN or halogen, it is optionally substituted with one or more halogens;

each $R^2$ is independently H, halogen or $C_1$-$C_4$ straight or branched alkyl;

$R^3$ is H, —OH, or halogen;

$R^{21}$ is cyclobutyl, azetidin-1-yl, or cyclopropyl;

$R^{22}$ is H, halogen, $C_1$-$C_2$ alkyl; and $R^{351}$ is $C_1$-$C_2$ alkyl or $C_2$—O—($C_1$ or $C_2$ alkyl);

or (u) Formula (XXI):

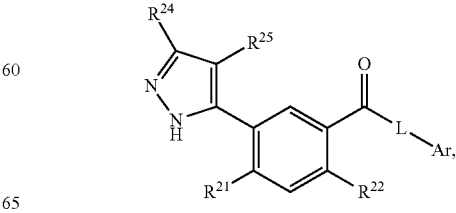

(XXI)

or a pharmaceutically acceptable salt thereof, wherein:

L-Ar is

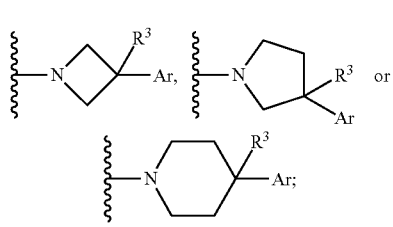

Ar is

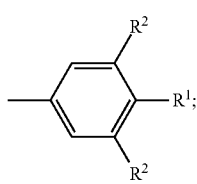

R¹ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when R¹ is not H, —CN or halogen. R¹ is optionally substituted with one or more halogen;

each R² is independently hydrogen, halogen or $C_1$-$C_4$ alkyl;

R³ is H or F;

R²¹ is H, halogen, $C_1$-$C_4$ alkyl, $C_3$-$C_5$ cycloalkyl or 4- to 6-membered heterocycle;

R²² is H, halogen or $C_1$-$C_2$ alkyl;

R²⁴ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein R²⁴ is optionally substituted with one or more hydroxyl or halogen; and R²⁵ is H, halogen, $C_1$-$C_4$ alkyl or $C_3$-$C_5$ cycloalkyl, wherein R²⁵ is optionally substituted with one or more halogen;

or (v) Formula (XXII):

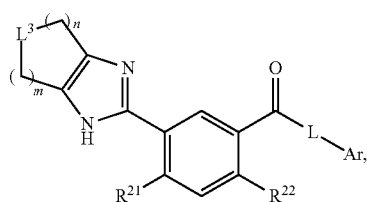

(XXII)

or a pharmaceutically acceptable salt thereof, wherein:

L³ is —CH₂—, —CHR⁵⁰—, —O—, —NR⁵⁰—, —NC(O)R⁵⁰— or —NC(O)OR⁵⁰—, wherein R⁵⁰ is $C_1$-$C_6$ alkyl, $C_3$-$C_5$ cycloalkyl, or 4- to 6-membered heterocycle;

n is 1, 2, or 3;

m is 1 or 2 wherein n+m≥3;

L-Ar is

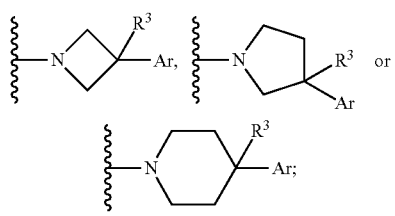

Ar is

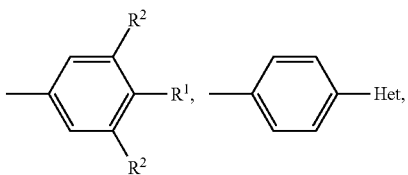

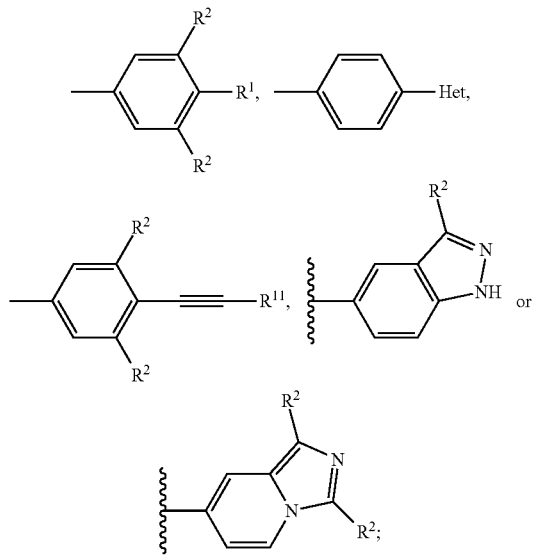

Het is a 5- to 6-membered heteroaryl;

R¹ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when R¹ is not H, —CN or halogen, R¹ is optionally substituted with one or more halogens;

each R² is independently hydrogen, halogen or $C_1$-$C_4$ alkyl;

R³ is H or F;

R¹¹ is H or —CH₃;

R²¹ is H, halogen, $C_1$-$C_4$ alkyl, $C_3$-$C_5$ cycloalkyl or a 4- to 6-membered heterocycle; and R²² is H, halogen, or $C_1$-$C_2$ alkyl;

or (w) Formula (XXIII):

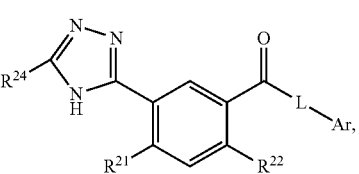

(XXIII)

or a pharmaceutically acceptable salt thereof, wherein:
L-Ar is

[Structure: azetidine with R³ and Ar substituents; pyrrolidine with R³ and Ar substituents; piperidine with R³ and Ar substituents]

Ar is

[Structure: phenyl with R², R¹, R² substituents; phenyl-Het]

[Structure: phenyl with R², R², and alkyne-R¹¹ substituent; indazole with R² substituent]

[Structure: imidazo[1,5-a]pyridine with two R² substituents]

Het is a 5- to 6-membered heteroaryl;

R¹ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when R¹ is not H, —CN or halogen, R¹ is optionally substituted with one or more halogens;

each R² is independently hydrogen, halogen or $C_1$-$C_4$ alkyl;

R³ is H or F;

R¹¹ is H or —CH₃;

R²¹ is H, halogen, $C_1$-$C_4$ alkyl, $C_3$-$C_5$ cycloalkyl or 4- to 6-membered heterocycle;

R²² is H, halogen, or $C_1$-$C_2$ alkyl; and

R²⁴ is H, $C_1$-$C_4$ alkyl, —($C_1$-$C_4$ alkyl)-OH, —($C_1$-$C_4$ alkyl)$_t$-N(R²⁴¹)₂, —($C_1$-$C_4$ alkyl)$_t$-O$_t$—($C_3$-$C_5$ cycloalkyl), —($C_1$-$C_4$ alkyl)$_t$-O$_t$-(4- to 6-membered heterocycle) or —($C_1$-$C_4$ alkyl)$_t$-O—($C_1$-$C_4$ alkyl), wherein:

each t is independently 0 or 1; and each R²⁴¹ is independently H or $C_1$-$C_2$ alkyl;

or (x) Formula (XXIV):

[Structure XXIV: imidazole with R²⁴, R²⁵ substituents connected to benzene with R²¹, R²² substituents and C(=O)-L-Ar group]

(XXIV)

or a pharmaceutically acceptable salt thereof,
wherein:
L-Ar is

[Structure: azetidine with R³ and Ar substituents; pyrrolidine with R³ and Ar substituents; piperidine with R³ and Ar substituents]

Ar is

[Structure: phenyl with R², R¹, R² substituents; phenyl-Het]

[Structure: phenyl with R², R², and alkyne-R¹¹ substituent; indazole with R² substituent]

[Structure: imidazo[1,5-a]pyridine with two R² substituents]

Het is a 5- to 6-membered heteroaryl;

R¹ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when R¹ is not H, —CN or halogen, R¹ is optionally substituted with one or more halogens;

each R² is independently hydrogen, halogen or $C_1$-$C_4$ alkyl;

R³ is H or F;

R¹¹ is H or —CH₃;

R²¹ is H, halogen, $C_1$-$C_4$ alkyl, $C_3$-$C_5$ cycloalkyl or 4- to 6-membered heterocycle;

R²² is H, halogen, or $C_1$-$C_2$ alkyl;

R²⁴ is H, —CN, —($C_1$-$C_4$ alkyl)-CN, $C_1$-$C_4$ alkyl, —($C_1$-$C_4$ alkyl)-OH, —($C_1$-$C_4$ alkyl)-N(R²⁴¹)₂, —($C_1$-$C_4$ alkyl)$_t$-

$O_u$—($C_3$-$C_6$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl), wherein:
t is 0 or 1;
u is 0 or 1;
with the proviso that when u is 1, t is 1; and
each $R^{241}$ is independently H or $C_1$-$C_2$ alkyl; and
$R^{25}$ is halogen, —CN, —($C_1$-$C_4$ alkyl)-CN, $C_1$-$C_2$ alkyl or cyclopropyl;
or
(y) Formula (XXV):

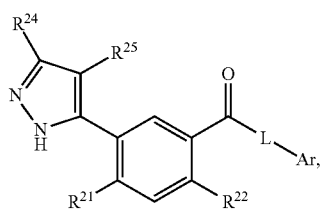

(XXV)

or a pharmaceutically acceptable salt thereof,
wherein:
L-Ar is

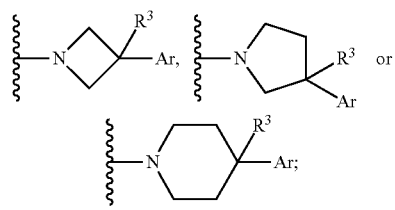

Ar is

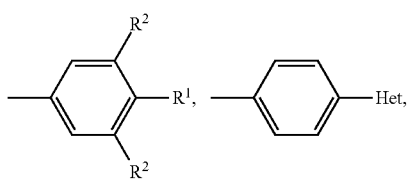

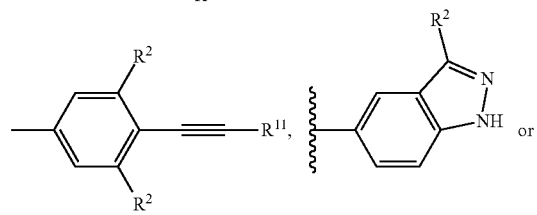

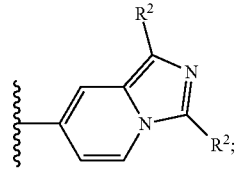

Het is a 5- to 6-membered heteroaryl;
$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;
$R^3$ is H or F;
$R^{11}$ is H or —$CH_3$;
$R^{21}$ is H, halogen, $C_1$-$C_4$ alkyl, $C_3$-$C_5$ cycloalkyl or 4- to 6-membered heterocycle;
$R^{22}$ is H, halogen or $C_1$-$C_2$ alkyl; and
each $R^{24}$ and $R^{25}$ is independently H, halogen, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, O—($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)$_t$-O—($C_1$-$C_4$ alkyl), wherein:
each t is independently 0 or 1;
each u is independently 0 or 1; and
each $R^{241}$ is independently H or $C_1$-$C_2$ alkyl,
wherein the compound is not:

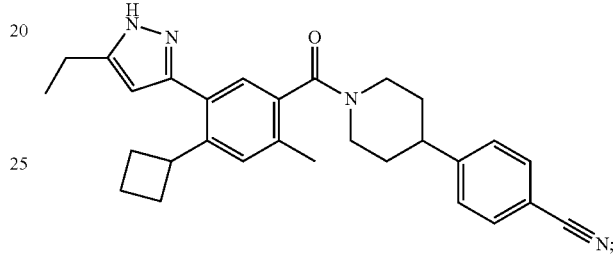

or
(z) Formula (XXVI):

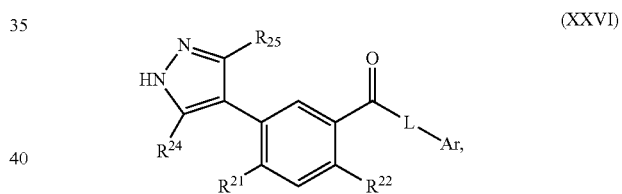

(XXVI)

or a pharmaceutically acceptable salt thereof,
wherein:
L-Ar is

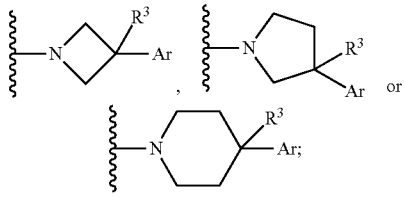

Ar is

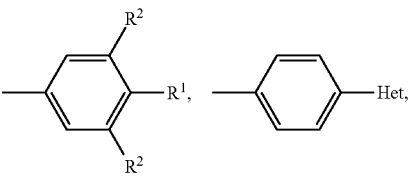

-continued

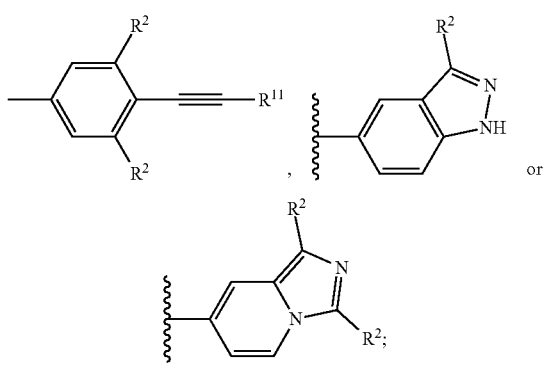

,   or

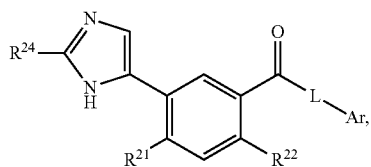

;

Het is a 5- to 6-membered heteroaryl; $R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens; each $R^2$ is independently hydrogen, halogen or $C_1$-$C_4$ alkyl; $R^3$ is H or F; $R^{11}$ is H or —$CH_3$; $R^{21}$ is H, halogen, $C_1$-$C_4$ alkyl, $C_3$-$C_5$ cycloalkyl or 4- to 6-membered heterocycle; $R^{22}$ is H, halogen or $C_1$-$C_2$ alkyl; and each of $R^{24}$ and $R^{25}$ is independently H, —$C_1$-$C_4$ alkyl, or halogen;

or (aa) Formula (XXVII):

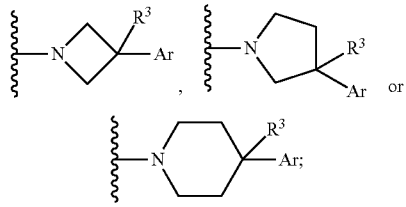

(XXVII)

or a pharmaceutically acceptable salt thereof, wherein:

L-Ar is

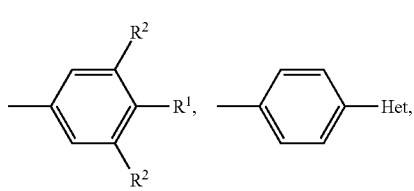

Ar is

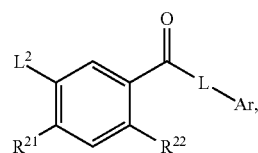

-continued

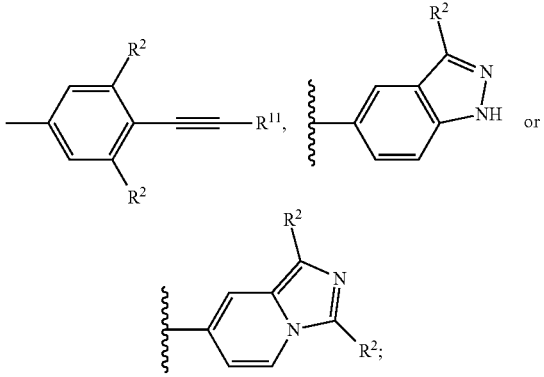

,  or

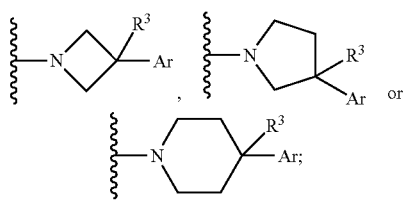

;

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl), wherein:

t is 0 or 1;

u is 0 or 1;

with the proviso that when u is 1, t is 1; and $R^{241}$ is H or $C_1$-$C_2$ alkyl.

or (bb) Formula (XXVIII):

(XXVIII)

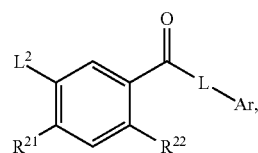

or a pharmaceutically acceptable salt thereof, wherein:

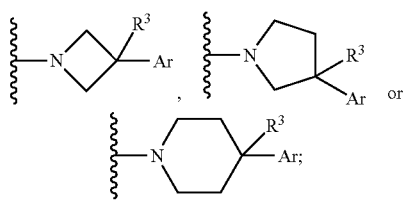

Ar is

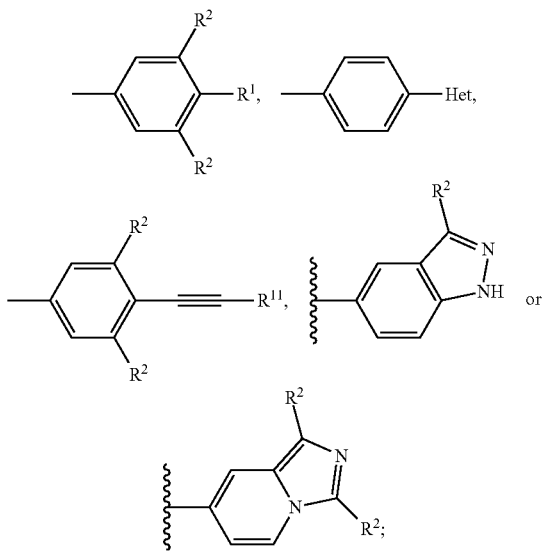

L² is —NHR³⁵ or —C(O)NHR³⁵¹, wherein R³⁵¹ is $C_1$-$C_6$ alkyl, $C_3$-$C_5$ cycloalkyl, 4- to 6-membered heterocycle, aryl or heteroaryl;

Het is a 5- to 6-membered heteroaryl;

R¹ is H, —CN, halogen, $C_1$-$C_4$ alkyl, —O—($C_3$-$C_5$ cycloalkyl), —O-(4- to 6-membered heterocycle), —O—($C_1$-$C_4$ alkyl) wherein when R¹ is not H, —CN or halogen, R¹ is optionally substituted with one or more halogens;

each R² is independently hydrogen, halogen or $C_1$-$C_4$ alkyl;

R³ is H or F;

R¹¹ is H or —CH₃;

R²¹ is H, halogen, $C_1$-$C_4$ alkyl, $C_3$-$C_5$ cycloalkyl or 4- to 6-membered heterocycle;

R²² is H, halogen, or $C_1$-$C_2$ alkyl; and

R³⁵ is —C(O)R³⁵¹, —C(O)NHR³⁵¹, C(O)OR³⁵¹ or S(O)₂R³⁵¹ wherein R³⁵¹ is $C_1$-$C_6$ alkyl, $C_3$-$C_5$ cycloalkyl, 4- to 6-membered heterocycle, aryl or heteroaryl, or (cc) Formula (XXIX):

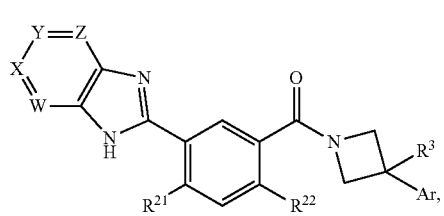

(XXIX)

or a pharmaceutically acceptable salt thereof,
wherein:

each W, X, Y and Z is independently —N— or —CR²⁶— with the proviso that not more than 2 of W, X, Y and Z are —N—;

each R²⁶ is independently H, $C_1$-$C_4$ alkyl, —O—($C_1$-$C_4$ alkyl), —N(R²⁷)₂, —S(O)₂—($C_1$-$C_4$ alkyl), or —C(O)—($C_1$-$C_4$ alkyl);

each R²⁷ is independently H or $C_1$-$C_4$ alkyl or both R²⁷ are $C_1$-$C_4$ alkyl and join to form a 3- to 6-membered ring together with the N to which they are attached and wherein the ring optionally includes one oxygen atom as one of the members of the ring;

Ar is

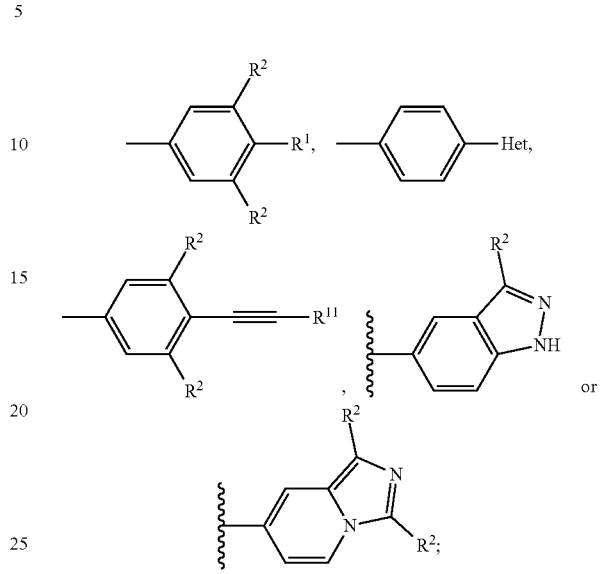

Het is a 5- to 6-membered heteroaryl;

R¹ is H, —CN, halogen, $C_1$-$C_4$ alkyl, —O—($C_3$-$C_5$ cycloalkyl), —O-(4- to 6-membered heterocycle), —O—($C_1$-$C_4$ alkyl) wherein when R¹ is not H, —CN or halogen, R¹ is optionally substituted with one or more halogens;

each R² is independently hydrogen, halogen or $C_1$-$C_4$ alkyl;

R³ is H or F;

R¹¹ is H or —CH₃;

R²¹ is H, halogen, $C_1$-$C_4$ alkyl, $C_3$-$C_5$ cycloalkyl or a 4- to 6-membered heterocycle; and R²² is H, halogen or $C_1$-$C_2$ alkyl.

In some embodiments of treating or preventing a taxane-resistant tumor or cancer with compounds of Formula (IV), $R_3$ is F.

In some embodiments of treating or preventing a taxane-resistant tumor or cancer with compounds of Formula (IV), A is CH.

In some embodiments of treating or preventing a taxane-resistant tumor or cancer with compounds of Formula (IV), A is N.

In some embodiments of treating or preventing a taxane-resistant tumor or cancer with compounds of Formula (IV), X, Y, and Z are NR'.

In some embodiments of treating or preventing a taxane-resistant tumor or cancer with compounds of Formula (IV), $R_4$ is heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, or $R_4$ and $R_{11}$ taken together with the atoms to which they are attached join together to form a heteroaryl.

In some embodiments of treating or preventing a taxane-resistant tumor or cancer with compounds of Formula (IV), $R_5$ is hydrogen and $R_6$ is aryl or heteroaryl.

In some embodiments of treating or preventing a taxane-resistant tumor or cancer with compounds of Formula (IV), the compound is of the Formula (IV-A) or (IV-B):

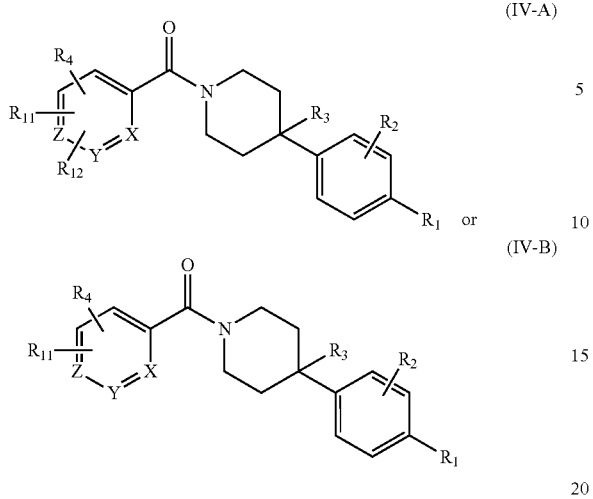

(IV-A)

(IV-B)

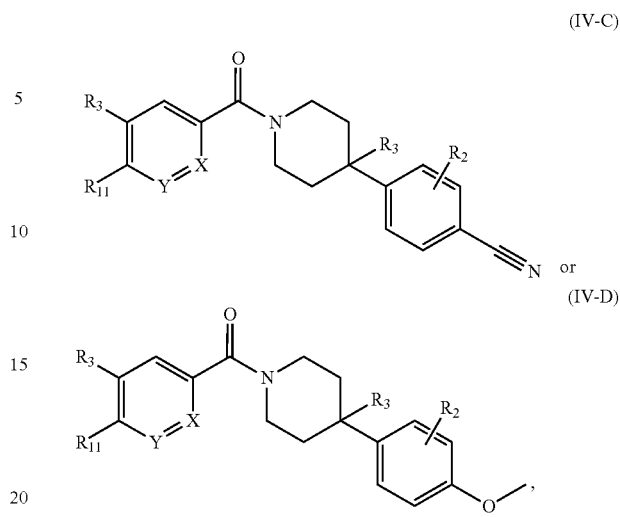

(IV-C)

(IV-D)

or a pharmaceutically acceptable salt thereof.
wherein:

X, Y, and Z are each independently CR or NR', wherein R is hydrogen or $C_{1-6}$ alkyl and R' is hydrogen, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), $(CH_2)_qC$(=O)N($R_{13}$)($R_{14}$), $CF_3$, —$OCF_3$, or —S(=O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$ $R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2R_{20}$;

$R_{15}$ and $R_{16}$ are each independently hydrogen, $C_{1-6}$ alkyl, cycloalkyl, aryl, heterocyclyl, heteroaryl, or alkylamino; and $R_{17}$ and $R_{18}$ are each independently hydrogen or alkyl or can optionally join together to form a bond.

In some embodiments of treating or preventing a taxane-resistant tumor or cancer with compounds of Formula (IV), the compound is of the Formula (IV-C) or (IV-D):

or a pharmaceutically acceptable salt thereof,
wherein:

X, Y, and Z are each independently CR or NR', wherein R is hydrogen or $C_{1-6}$ alkyl and R' is hydrogen, $C_{1-6}$ alkyl, or absent; $R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (IV), the compound is of the Formula (IV-E), (IV-F), (IV-G), (IV-H):

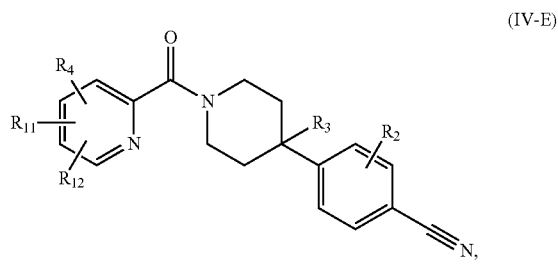

(IV-E)

(IV-F)

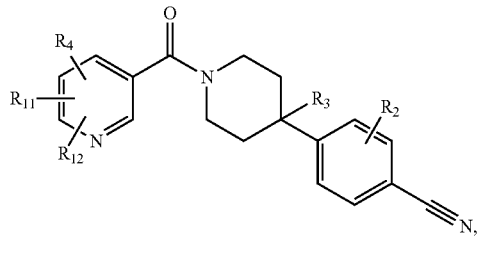

(IV-G)

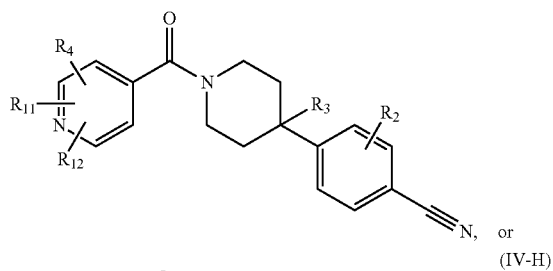

, or (IV-H)

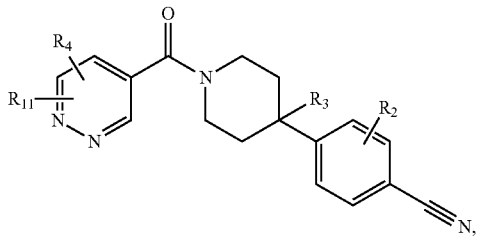

, (IV-I)

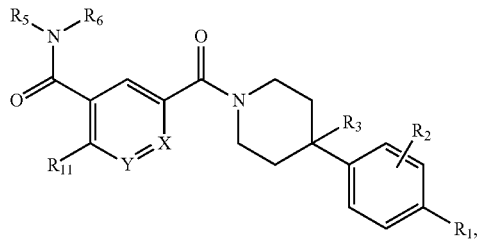

, (IV-J)

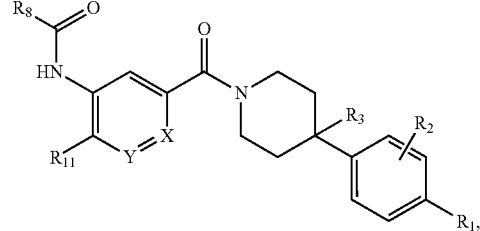

, or (IV-K)

, or a pharmaceutically acceptable salt thereof,
wherein:

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (IV), the compound is of the Formula (IV-I), (IV-J), or (IV-K):

or a pharmaceutically acceptable salt thereof,
wherein:

X and Y are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), $(CH_2)_qC(=O)N(R_{13})(R_{14})$, $CF_3$, —$OCF_3$, or —S(=O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_{11}$ is hydrogen, halo, cyano, $C_{1-6}$ alkyl, $C_{1-6}$ alkoxy, —N($R_{13}R_{14}$), $CF_3$, —$OCF_3$, or —S(=O)$_2R_{20}$;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (IV), the compound is of the Formula (IV-L) or (IV-M):

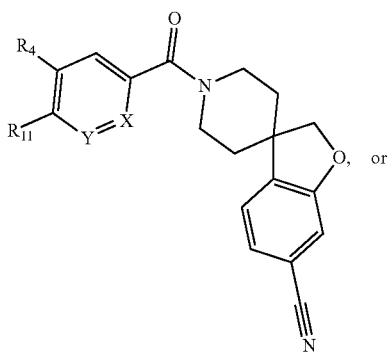

(IV-L)

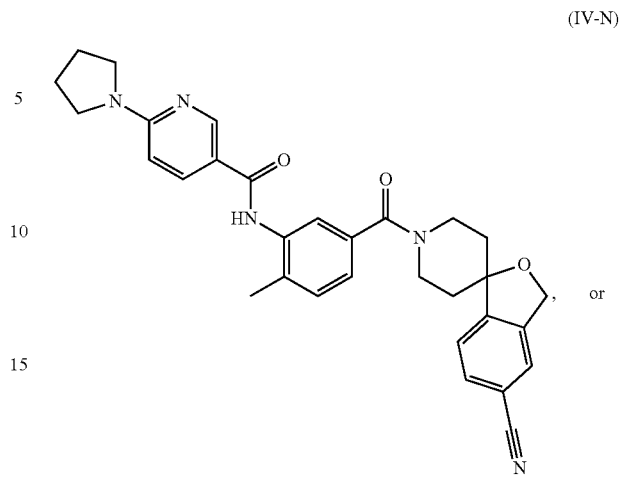

(IV-N)

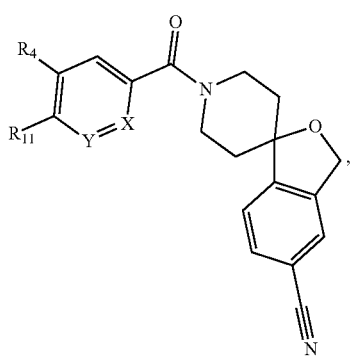

(IV-M)

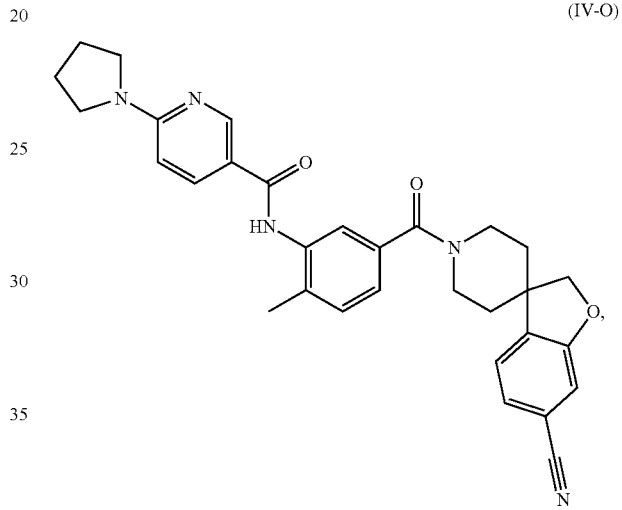

(IV-O)

or a pharmaceutically acceptable salt thereof.

wherein:

X and Y are each independently CR or NR', wherein R is H or $C_{1-6}$ alkyl and R' is H, $C_{1-6}$ alkyl, or absent;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (IV), the compound is of the Formula (IV-N) or (IV-O):

or a pharmaceutically acceptable salt thereof.

In some embodiments of treating or preventing a taxane-resistant tumor or cancer with compounds of Formula (IV), having the following Formula (IV-P):

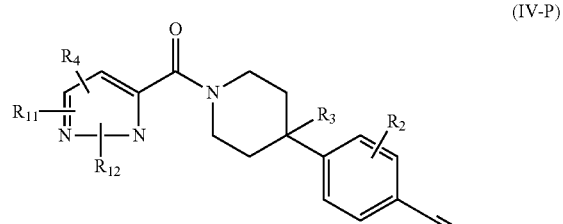

(IV-P)

or a pharmaceutically acceptable salt thereof, wherein:

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and R₁₁ taken together with the atoms to which they are attached join together to form a heteroaryl;

R₂₀ is hydrogen or C₁₋₆ alkyl, C₁₋₆ alkoxy, or —N(R₁₃)(R₁₄);

R₁₁ is hydrogen, halo, cyano, C₁₋₆ alkyl, C₁₋₆ alkoxy, —N(R₁₃R₁₄), CF₃, —OCF₃, —S(=O)₂R₂₀, R₄ and R₁₁ taken together with the atoms to which they are attached join together to form a heteroaryl, or R₁₁ and R₁₂ taken together with the atoms to which they are attached join together to form a heteroaryl;

R₁₂ is hydrogen, halo, cyano, C₁₋₆ alkyl, C₁₋₆ alkoxy, —N(R₁₃R₁₄), CF₃, —OCF₃, —S(=O)₂R₂₀, or R₁₁ and R₁₂ taken together with the atoms to which they are attached join together to form a heteroaryl;

R₅, R₆, R₇, R₈, R₉, R₁₀, R₁₃, and R₁₄ are each independently H, C₁₋₆ alkyl, cycloalkyl, aryl, heterocyclyl, heteroaryl, alkylamino, or —N(R₁₅R₁₆); and R₁₅ and R₁₆ are each independently H, C₁₋₆ alkyl, cycloalkyl, aryl, heterocyclyl, heteroaryl, or alkylamino.

In some embodiments of treating or preventing a taxane-resistant tumor or cancer with compounds of Formula (IV), the compound is of the Formula (IV-Q), (IV-R), or (IV-S):

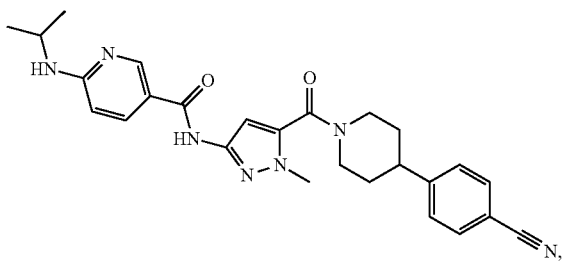

(IV-Q)

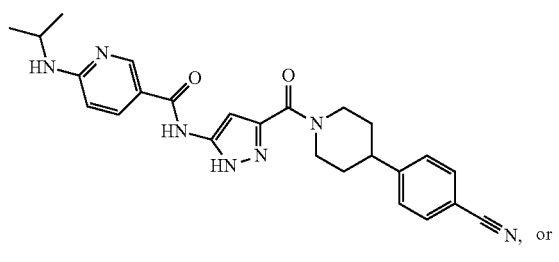

(IV-R)

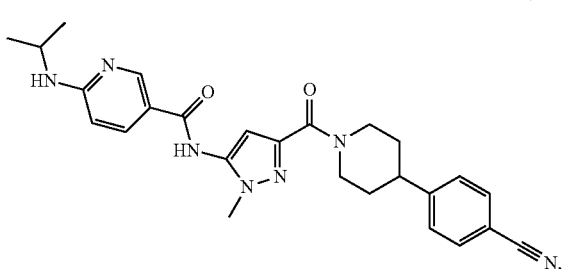

(IV-S)

or a pharmaceutically acceptable salt thereof.

In some embodiments of treating or preventing a taxane-resistant tumor or cancer with compounds of Formula (IV) having the following Formula (IV-T):

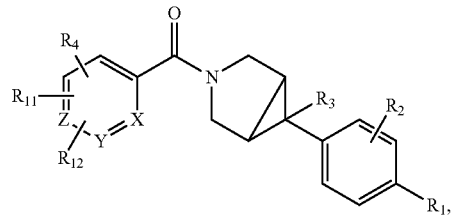

(IV-T)

or a pharmaceutically acceptable salt thereof,
wherein:

X, Y, and Z are each independently CR or NR', wherein R is H or C₁₋₆ alkyl and R' is H, C₁₋₆ alkyl, or absent;

R₁ is hydrogen, cyano, halo, C₁₋₆ alkyl, C₁₋₆ alkoxy, —C(=O)N(R₁₃)(R₁₄), —(CH₂)ₑC(=O)N(R₁₃)(R₁₄), CF₃, —OCF₃, or —S(O)₂R₂₀;

q is 0, 1, 2, 3, or 4;

R₂₀ is hydrogen or C₁₋₆ alkyl, C₁₋₆ alkoxy, or —N(R₁₃)(R₁₄);

R₂ is hydrogen, halo, C₁₋₆ alkoxy, C₁₋₆ alkyl, or R₂ and R₃ taken together with the atoms to which they are attached form a 5-membered heterocyclyl;

R₃ is hydrogen, hydroxyl, halo, C₁₋₆ alkyl, C₁₋₆ alkoxy, or R₂ and R₃ taken together with the atoms to which they are attached form a 5-membered heterocyclyl;

R₄ is hydrogen, heteroaryl, heterocyclyl, —C(=O)N(R₅R₆), —N(R₇)C(=O)R₈, —N(R₉R₁₀), C₁₋₆ alkyl, C₁₋₆ alkoxy, —S(=O)₂R₂₀, or R₄ and R₁₁ taken together with the atoms to which they are attached join together to form a heteroaryl;

R₁₁ is hydrogen, halo, cyano, C₁₋₆ alkyl, C₁₋₆ alkoxy, —N(R₁₃R₁₄), CF₃, —OCF₃, —S(=O)₂R₂₀, R₄ and R₁₁ taken together with the atoms to which they are attached join together to form a heteroaryl, or R₁₁ and R₁₂ taken together with the atoms to which they are attached join together to form a heteroaryl;

R₁₂ is hydrogen, halo, cyano, C₁₋₆ alkyl, C₁₋₆ alkoxy, —N(R₁₃R₁₄), CF₃, —OCF₃, —S(=O)₂R₂₀, or R₁₁ and R₁₂ taken together with the atoms to which they are attached join together to form a heteroaryl;

R₅, R₆, R₇, R₈, R₉, R₁₀, R₁₃, and R₁₄ are each independently H, C₁₋₆ alkyl, cycloalkyl, aryl, heterocyclyl, heteroaryl, alkylamino, or —N(R₁₅R₁₆); and R₁₅ and R₁₆ are each independently H, C₁₋₆ alkyl, cycloalkyl, aryl, heterocyclyl, heteroaryl, or alkylamino.

In some embodiments of treating or preventing a taxane-resistant tumor or cancer with compounds of Formula (IV), having the following Formula (IV-U):

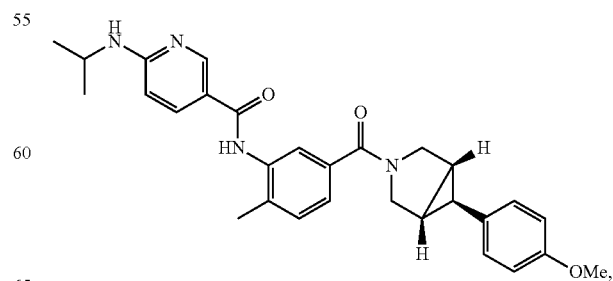

(IV-U)

or a pharmaceutically acceptable salt thereof.

In some embodiments of treating or preventing a taxane-resistant tumor or cancer with compounds of Formula (IV), the compound is of the Formula (IV-V):

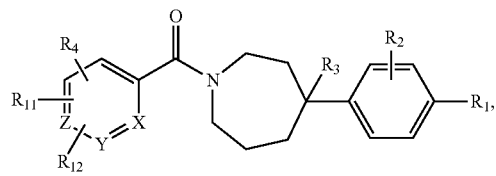

(IV-V)

or a pharmaceutically acceptable salt thereof,
wherein:

X, Y, and Z are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —CF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (IV), having the following Formula (IV-W):

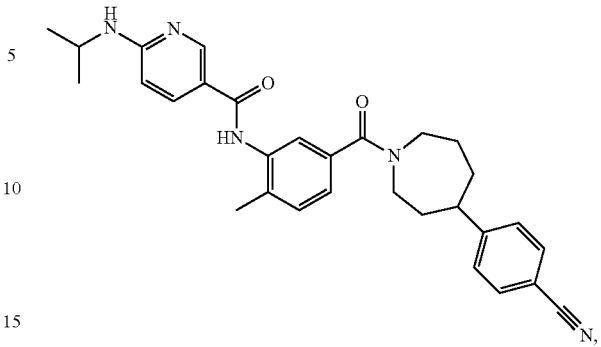

(IV-W)

or a pharmaceutically acceptable salt thereof.

In some embodiments of treating or preventing a taxane-resistant tumor or cancer with compounds of Formula (IV), the compound is of one the following Formula (IV-X), (IV-Y), (IV-Z), (IV-AA), (IV-AB, (IV-AC), (IV-AD), (IV-AF), (IV-AG), or (IV-AH):

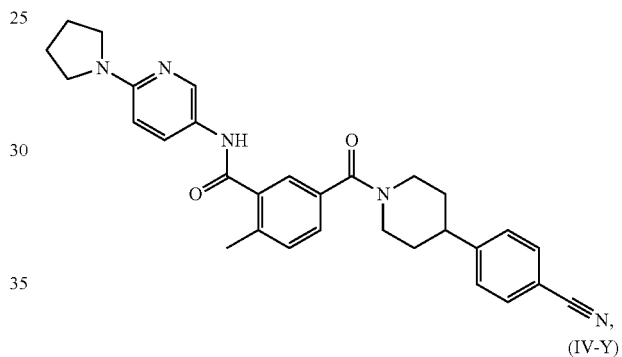

(IV-X)

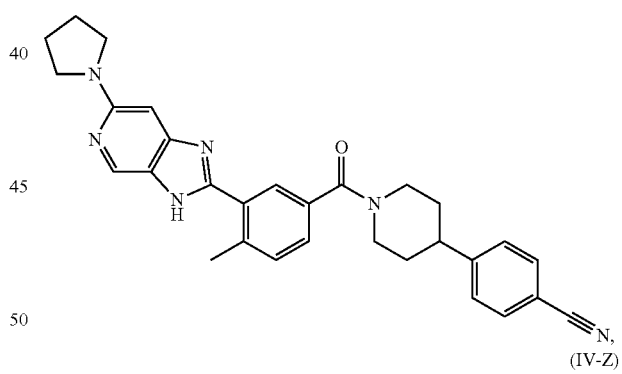

(IV-Y)

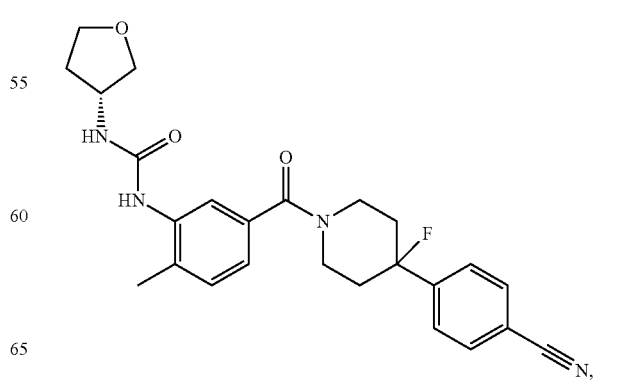

(IV-Z)

47

-continued (IV-AA)

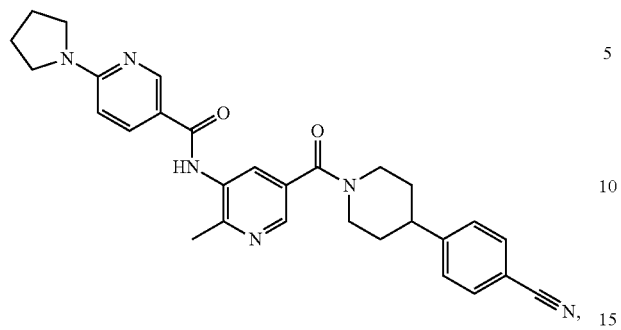

(IV-AB)

(IV-AC)

(IV-AD)

48

-continued (IV-AE)

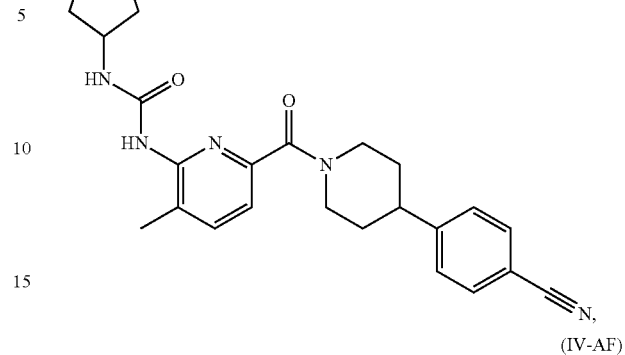

(IV-AF)

(IV-AG)

(IV-AH)

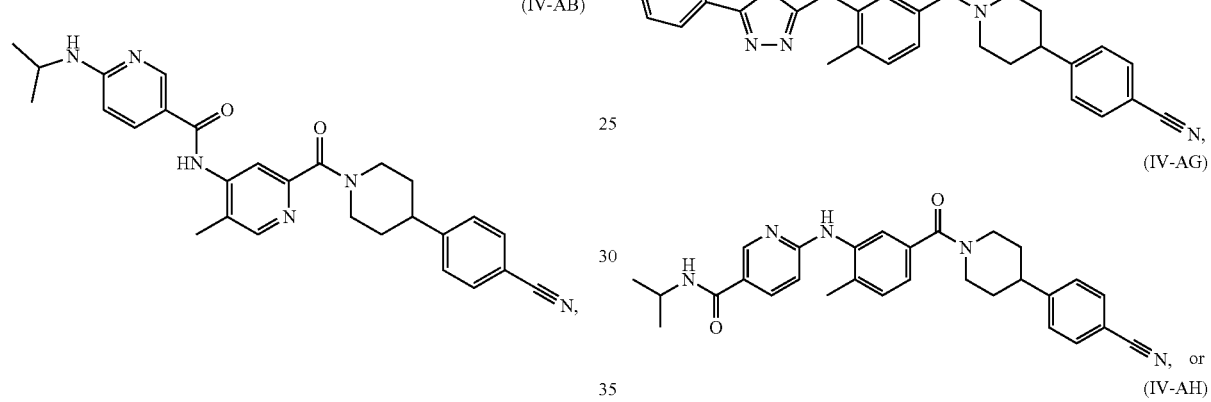

or a pharmaceutically acceptable salt thereof.

In some embodiments of treating or preventing a taxane-resistant tumor or cancer with compounds of Formula (V), having the following Formula (V-A):

(V-A)

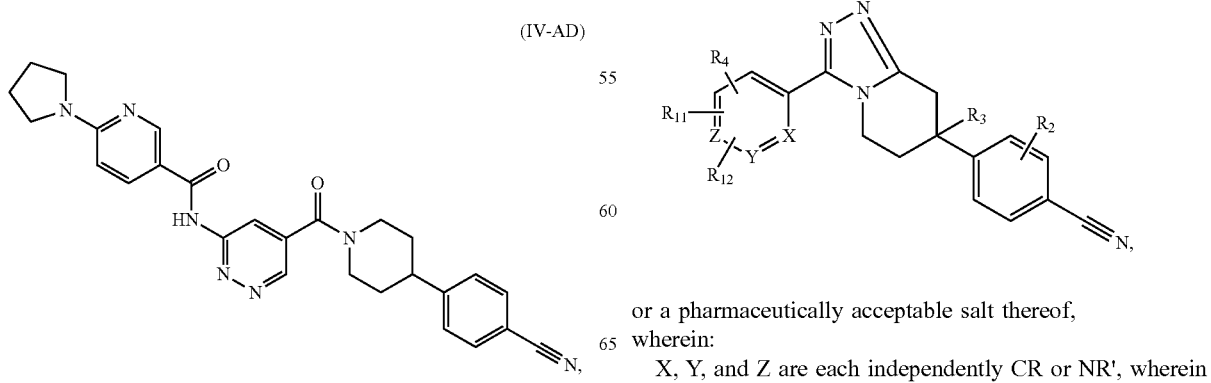

or a pharmaceutically acceptable salt thereof,
wherein:
X, Y, and Z are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-4}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (V), having the following Formula (V-B):

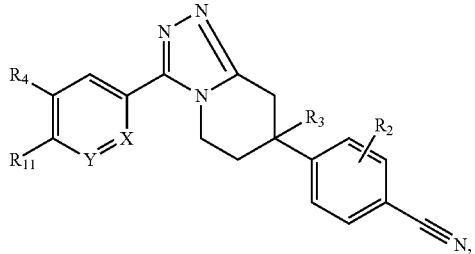

(V-B)

or a pharmaceutically acceptable salt thereof,
wherein:

X and Y are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (V), the compound is of the Formula (V-C), (V-D), or (V-E):

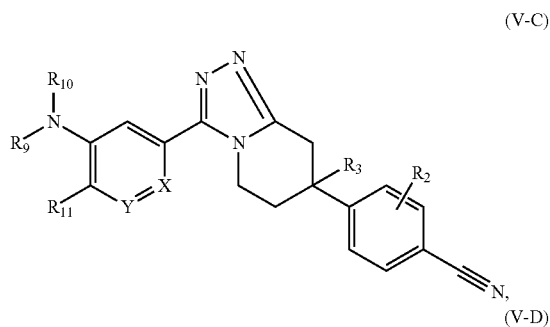

(V-C)

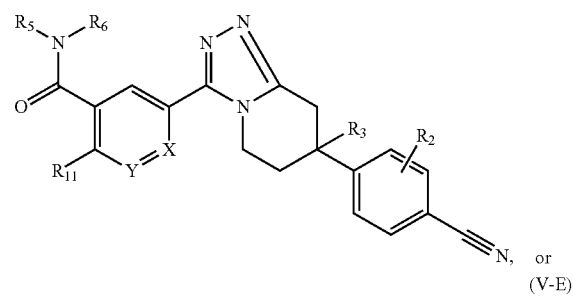

(V-D)

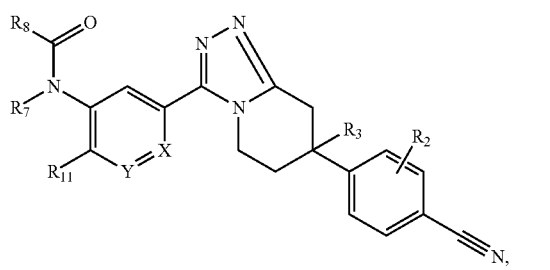

(V-E)

or a pharmaceutically acceptable salt thereof,
wherein:

X and Y are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_{11}$ is hydrogen, halo, cyano, $C_{1-6}$ alkyl, $C_{1-6}$ alkoxy, —N($R_{13}R_{14}$), $CF_3$, —$OCF_3$, or —S(=O)$_2R_{20}$;

$R_{20}$ is hydrogen or $C_{1-6}$ alkyl, $C_{1-6}$ alkoxy, or —N($R_{13}$)($R_{14}$);

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$) and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (V), having the following Structure (V-F):

(V-F)

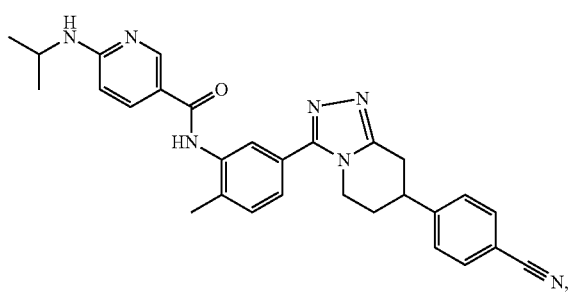

or a pharmaceutically acceptable salt thereof.

In some embodiments of treating or preventing a taxane-resistant tumor or cancer with compounds of Formula (VI), the compound is of the Formula (VI-A), (VI-B), or (VI-C):

(VI-A)

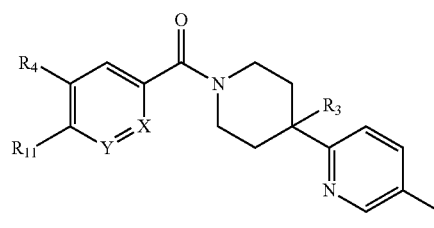

(VI-B)

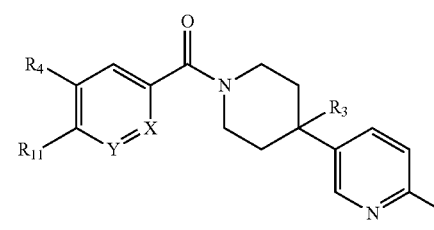

or (VI-C)

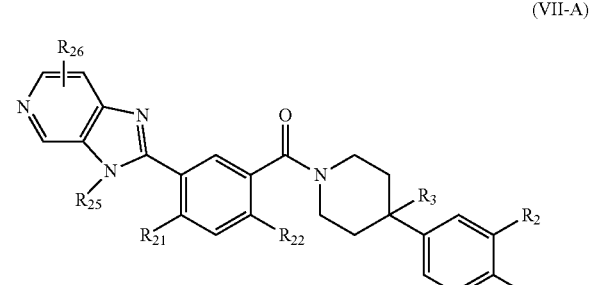

or a pharmaceutically acceptable salt thereof, wherein:

X and Y are each independently CR or NR', wherein R is H or $C_{1-6}$ alkyl and R' is H, $C_{1-6}$ alkyl, or absent;

$R_3$ is hydrogen, hydroxyl, halo, $C_{1-6}$ alkyl, or $C_{1-6}$ alkoxy;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In some embodiments of treating or preventing a taxane-resistant tumor or cancer with compounds of Formula (VI), the compound is of the Formula (VI-D), (VI-E), or (VI-F):

(VI-D)

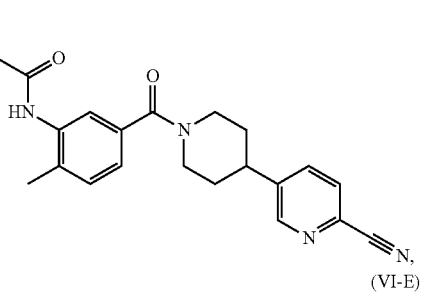

(VI-E)

[Structure image]

or (VI-F)

[Structure image]

or a pharmaceutically acceptable salt thereof.

In some embodiments of treating or preventing a taxane-resistant tumor or cancer with compounds of Formula (VII), (VIII) or (IX), the compound is of the Formula (VII-A) or (VII-B):

(VII-A)

[Structure image]

or

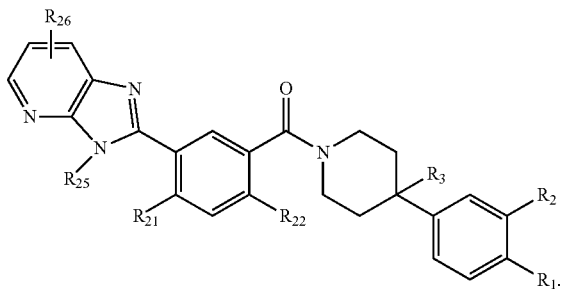
(VII-B)

or a pharmaceutically acceptable salt thereof
wherein:
R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;
q is 0, 1, 2, 3, or 4;
R$_{20}$ is hydrogen or C$_{1-6}$ alkyl, C$_{1-6}$ alkoxy, or —N(R$_{13}$)(R$_{14}$);
R$_2$ is hydrogen, halo, C$_{1-6}$ alkoxy, or C$_{1-6}$ alkyl;
R$_3$ is hydrogen, hydroxyl, halo, C$_{1-6}$ alkyl, or C$_{1-6}$ alkoxy;
R$_{21}$ and R$_{22}$ are each independently hydrogen, halo, cyano, C$_{1-6}$ alkyl, C$_{1-6}$ alkoxy, CF$_3$, —OCF$_3$, or —S(=O)$_2$R$_{20}$;
R$_{26}$ is hydrogen, heteroaryl, heterocyclyl, —N(R$_{13}$)(R$_{14}$), or —S(=O)$_2$R$_{20}$;
R$_{13}$ and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;
R$_{25}$ is hydrogen, C$_{1-6}$ alkyl, or C$_{1-6}$ alkoxy; and
R$_{15}$ and R$_{16}$ are each independently hydrogen, C$_{1-6}$ alkyl, C$_{1-6}$ alkoxy, cycloalkyl, aryl, heterocyclyl, heteroaryl, hydroxyalkyl, or alkylamino.

In some embodiments of treating or preventing a taxane-resistant tumor or cancer with compounds of Formula (VII), (VIII) or (IX), the compound is of the Formula (VII-C) or (VII-D):

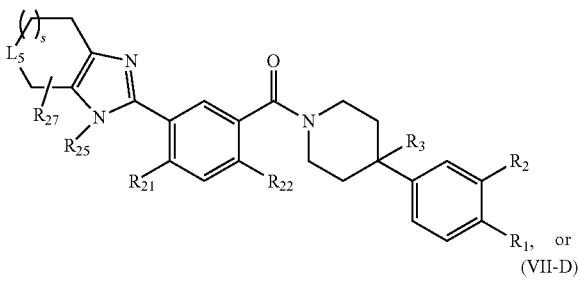
(VII-C)

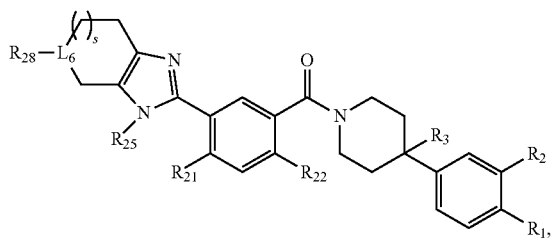
(VII-D)

or a pharmaceutically acceptable salt thereof,
wherein:
R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;
q is 0, 1, 2, 3, or 4;
R$_{20}$ is hydrogen or C$_{1-6}$ alkyl, C$_{1-6}$ alkoxy, or —N(R$_{13}$)(R$_{14}$);
R$_2$ is hydrogen, halo, C$_{1-6}$ alkoxy, or C$_{1-6}$ alkyl;
R$_3$ is hydrogen, hydroxyl, halo, C$_{1-6}$ alkyl, or C$_{1-6}$ alkoxy;
R$_{21}$ and R$_{22}$ are each independently hydrogen, halo, cyano, C$_{1-6}$ alkyl, C$_{1-6}$alkoxy, CF$_3$, —OCF$_3$, or —S(=O)$_2$R$_{20}$;
R$_{13}$ and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;
R$_{25}$ is hydrogen, C$_{1-6}$ alkyl, or C$_{1-6}$ alkoxy;
R$_{15}$ and R$_{16}$ are each independently hydrogen, C$_{1-6}$ alkyl, C$_1$-6 alkoxy, cycloalkyl, aryl, heterocyclyl, heteroaryl, hydroxyalkyl, or alkylamino;
s is 0, 1, or 2;
L$_5$ is CH$_2$, NH, S, or O;
L$_6$ is CH or N;
R$_{27}$ is hydrogen, —C(=O)R", —S(=O)$_2$R$_{20}$;
R$_{28}$ is hydrogen, —C(=O)R", —S(=O)$_2$R$_{20}$, or is absent if L$_6$ is O; and
R" is hydrogen, C$_{1-6}$ alkyl, C$_{1-6}$ alkoxy, —C(=O)N(R$_{13}$)(R$_{14}$), or —N(R$_{13}$)(R$_{14}$).

In some embodiments of treating or preventing a taxane-resistant tumor or cancer with compounds of Formula (VII), (VIII) or (IX), R$_1$ is hydrogen, cyano, C$_{1-6}$ alkyl, C$_{1-6}$ alkoxy, or —C(=O)N(R$_{13}$)(R$_{14}$).

In some embodiments of treating or preventing a taxane-resistant tumor or cancer with compounds of Formula (VII), (VIII) or (IX), R$_1$ is cyano.

In some embodiments of treating or preventing a taxane-resistant tumor or cancer with compounds of Formula (VII), (VIII) or (IX), R$_2$ is hydrogen or halo; R$_2$ is hydrogen.

In some embodiments of treating or preventing a taxane-resistant tumor or cancer with compounds of Formula (VII), (VIII) or (IX), R$_3$ is hydrogen.

In some embodiments of treating or preventing a taxane-resistant tumor or cancer with compounds of Formula (VII), (VIII) or (IX), R$_{21}$ and R$_{22}$ are each independently hydrogen or C$_{1-6}$ alkyl.

In some embodiments of treating or preventing a taxane-resistant tumor or cancer with compounds of Formula (VII), (VIII) or (IX), R$_{21}$ and R$_{22}$ are each independently C$_{1-6}$ alkyl.

In some embodiments of treating or preventing a taxane-resistant tumor or cancer with compounds of Formula (VII), (VIII) or (IX), R$_{25}$ is hydrogen.

In some embodiments of treating or preventing a taxane-resistant tumor or cancer with compounds of Formula (VII), (VIII) or (IX), L$_2$ is N.

In some embodiments of treating or preventing a taxane-resistant tumor or cancer with compounds of Formula (VII), (VIII) or (IX), L$_1$ is CH.

In some embodiments of treating or preventing a taxane-resistant tumor or cancer with compounds of Formula (VII), (VIII) or (IX), L$_3$ is CH.

In some embodiments of treating or preventing a taxane-resistant tumor or cancer with compounds of Formula (VII), (VIII) or (IX), L$_4$ is CH.

In some embodiments of treating or preventing a taxane-resistant tumor or cancer with compounds of Formula (VII), (VIII) or (IX), A is N.

In some embodiments of treating or preventing a taxane-resistant tumor or cancer with compounds of Formula (VII), (VIII) or (IX), A is CH.

In some embodiments of treating or preventing a taxane-resistant tumor or cancer with compounds of Formula (VII), (VIII) or (IX), $R_{26}$ is heterocyclyl.

In some embodiments of treating or preventing a taxane-resistant tumor or cancer with compounds of Formula (VII), (VIII) or (IX), $R_{24}$ is —N($R_{13}$)($R_{14}$).

In some embodiments of treating or preventing a taxane-resistant tumor or cancer with compounds of Formula (VII), (VIII) or (IX), $L_5$ and $L_6$ are each independently N.

In some embodiments of treating or preventing a taxane-resistant tumor or cancer with compounds of Formula (VII), (VIII) or (IX), s is 1.

In some embodiments of treating or preventing a taxane-resistant tumor or cancer with compounds of Formula (VII), (VIII) or (IX), s is 0.

In some embodiments of treating or preventing a taxane-resistant tumor or cancer with compounds of Formula (VII), (VIII) or (IX), one of the following Formula (VII-E), (VII-F), (VII-G), (VII-H), (VII-I), (VII-J), (VII-K), or (VII-L):

(VII-E)

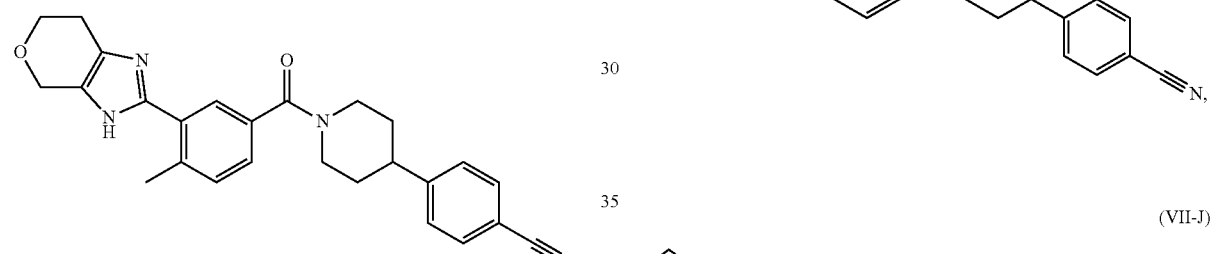

(VII-F)

(VII-G)

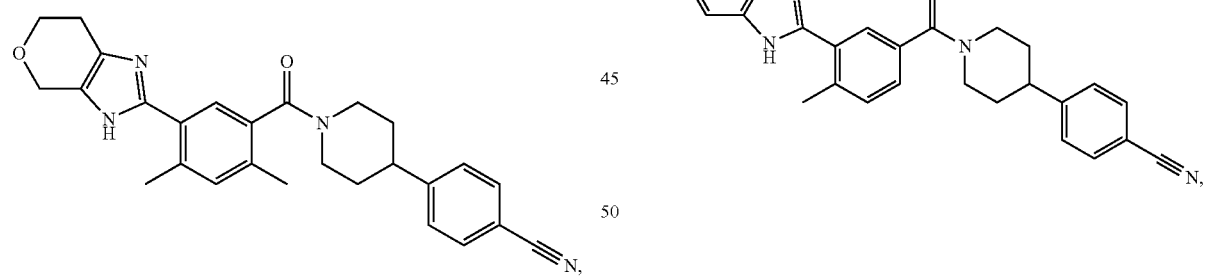

-continued (VII-H)

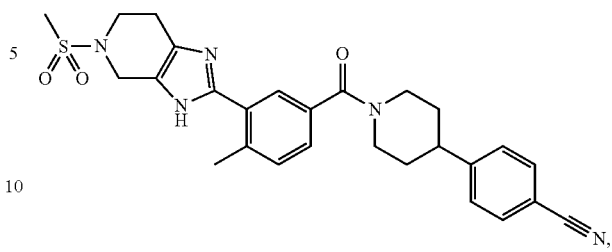

(VII-I)

(VII-J)

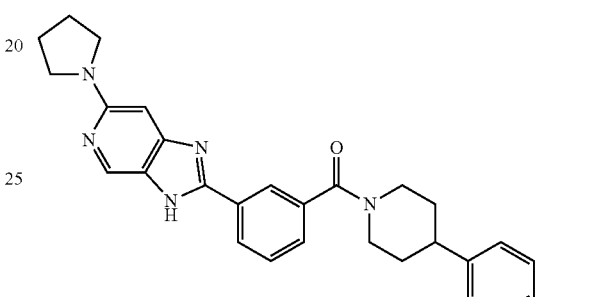

(VII-K)

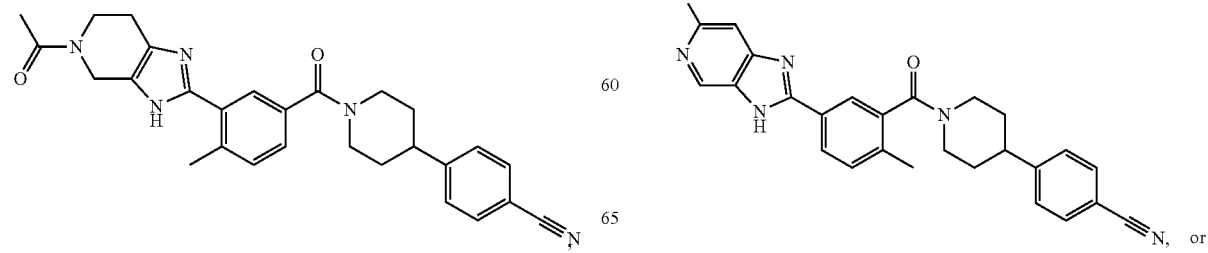

or (VII-L)

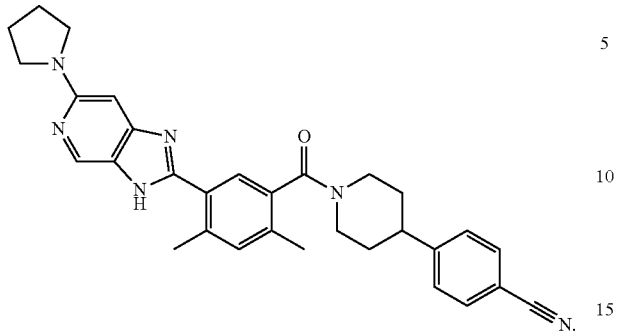

or a pharmaceutically acceptable salt thereof.

In some embodiments of treating or preventing a taxane-resistant tumor or cancer with compounds of Formula (X), the compound is of the Formula (X-A), (X-B), (X-C), or (X-D):

(X-A)

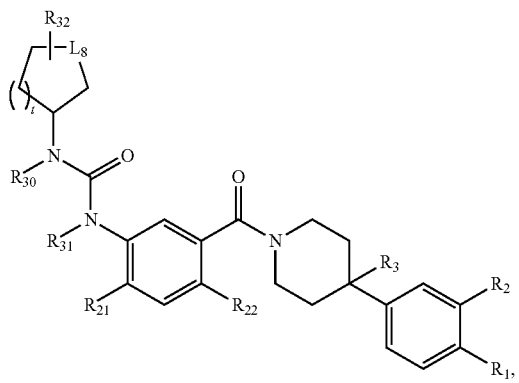

(X-B)

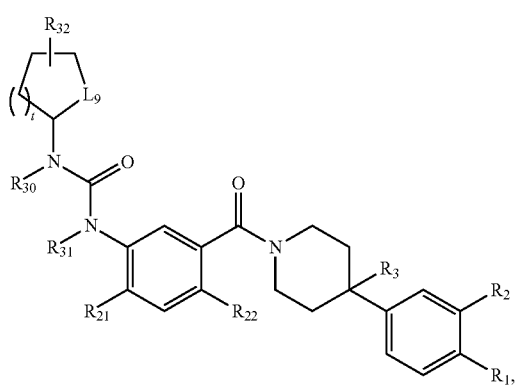

(X-C)

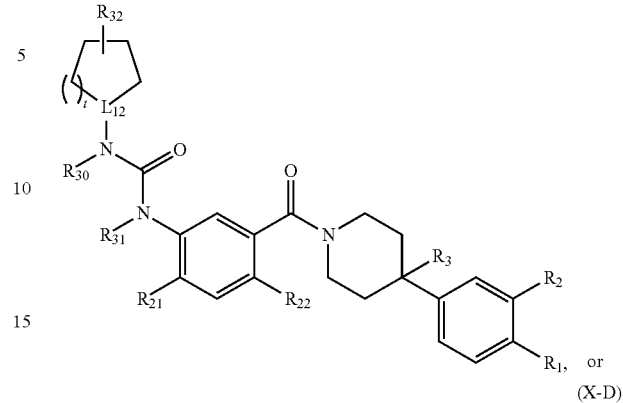

or a pharmaceutically acceptable salt thereof,
wherein:
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{30}$ is hydrogen, $C_{1-6}$ alkyl, $C_{1-6}$ alkoxy, hydroxyalkyl, heteroaryl, heterocyclyl, —N($R_{15}R_{16}$), —C(=O)R$_{46}$, or —R$_{48}$C(=O)R$_{47}$, wherein $R_{30}$ is absent if $L_7$ is O;
$R_{46}$ and $R_{47}$ are each independently hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;
$R_{48}$ is alkyl or is absent;
$R_{31}$ is hydrogen, $C_{1-6}$ alkyl, or $C_{1-6}$ alkoxy;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{15}$ and $R_{16}$ are each independently hydrogen, $C_{1-6}$ alkyl, cycloalkyl, aryl, heterocyclyl, heteroaryl, hydroxyalkyl, or alkylamino;
$L_8$, $L_9$, and $L_{10}$ are each independently CH$_2$, NH, or O;
$L_{11}$ and $L_{12}$ are each independently CH or N;
$R_{32}$ and $R_{33}$ are each independently hydrogen, $C_{1-6}$ alkyl, $C_{1-6}$ alkoxy, —S(=O)$_2$R$_{20}$, —C(=O)R$_{46}$, hydroxyalkyl, hydroxyl, or are absent;
u is 0, 1, or 2; and
t is 0, 1, or 2.

In some embodiments of treating or preventing a taxane-resistant tumor or cancer with compounds of Formula (X), $L_7$ is N.

In some embodiments of treating or preventing a taxane-resistant tumor or cancer with compounds of Formula (X), $L_7$ is O.

In some embodiments of treating or preventing a taxane-resistant tumor or cancer with compounds of Formula (X), A is N.

In some embodiments of treating or preventing a taxane-resistant tumor or cancer with compounds of Formula (X), A is CH.

In some embodiments of treating or preventing a taxane-resistant tumor or cancer with compounds of Formula (X), $R_1$ is hydrogen, cyano, $C_{1-6}$ alkyl, $C_{1-6}$ alkoxy, or —C(=O)N($R_{13}$)($R_{14}$).

In some embodiments of treating or preventing a taxane-resistant tumor or cancer with compounds of Formula (X), $R_1$ is cyano.

In some embodiments of treating or preventing a taxane-resistant tumor or cancer with compounds of Formula (X), $R_2$ is hydrogen or halo.

In some embodiments of treating or preventing a taxane-resistant tumor or cancer with compounds of Formula (X), $R_2$ is hydrogen.

In some embodiments of treating or preventing a taxane-resistant tumor or cancer with compounds of Formula (X), $R_3$ is fluorine.

In some embodiments of treating or preventing a taxane-resistant tumor or cancer with compounds of Formula (X), $R_{21}$ and $R_{22}$ are each independently hydrogen or $C_{1-6}$ alkyl.

In some embodiments of treating or preventing a taxane-resistant tumor or cancer with compounds of Formula (X), $R_{21}$ and $R_{22}$ are each independently $C_{1-6}$ alkyl.

In some embodiments of treating or preventing a taxane-resistant tumor or cancer with compounds of Formula (X), $R_{31}$ is hydrogen.

In some embodiments of treating or preventing a taxane-resistant tumor or cancer with compounds of Formula (X), $R_{30}$ is hydrogen.

In some embodiments of treating or preventing a taxane-resistant tumor or cancer with compounds of Formula (X), $L_8$ is O.

In some embodiments of treating or preventing a taxane-resistant tumor or cancer with compounds of Formula (X), $L_9$ is O.

In some embodiments of treating or preventing a taxane-resistant tumor or cancer with compounds of Formula (X), $L_{10}$ is O and $L_{11}$ is N.

In some embodiments of treating or preventing a taxane-resistant tumor or cancer with compounds of Formula (X), $L_{12}$ is N.

In some embodiments of treating or preventing a taxane-resistant tumor or cancer with compounds of Formula (X), $R_{32}$ and $R_{33}$ are each independently hydrogen.

In some embodiments of treating or preventing a taxane-resistant tumor or cancer with compounds of Formula (X), the compound is of Formula (X-I), (X-J), (X-K), (X-L), (X-M), (X-N), or (X-O):

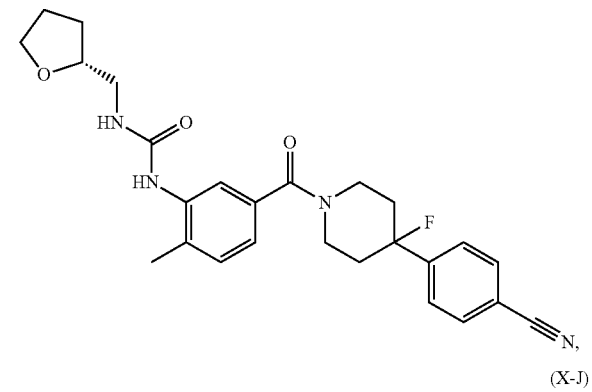
(X-I)

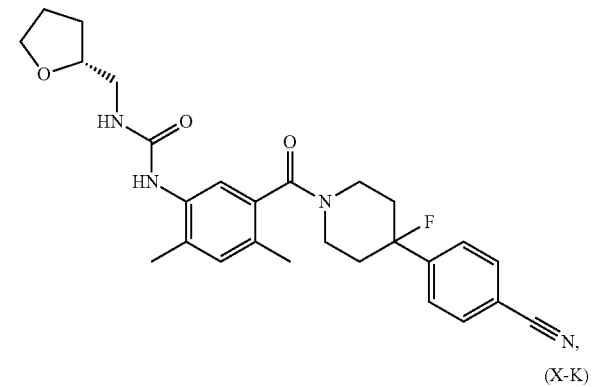
(X-J)

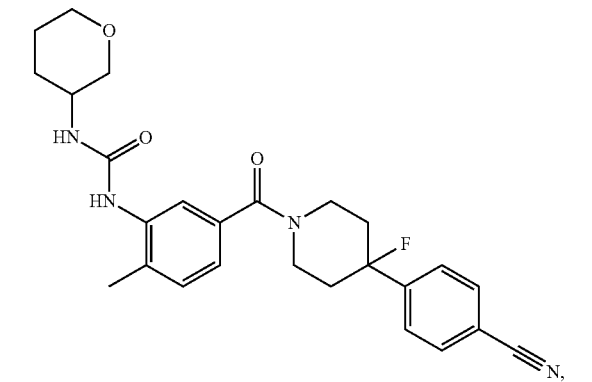
(X-K)

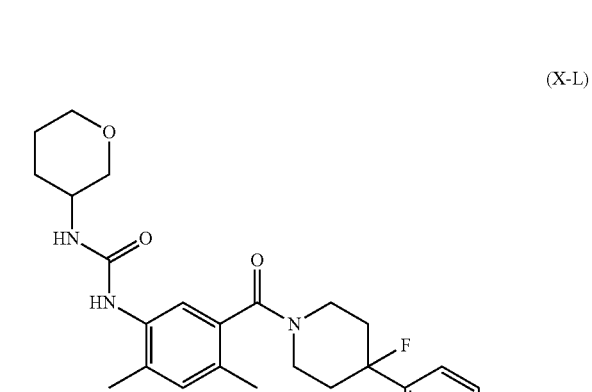
(X-L)

-continued (X-M)

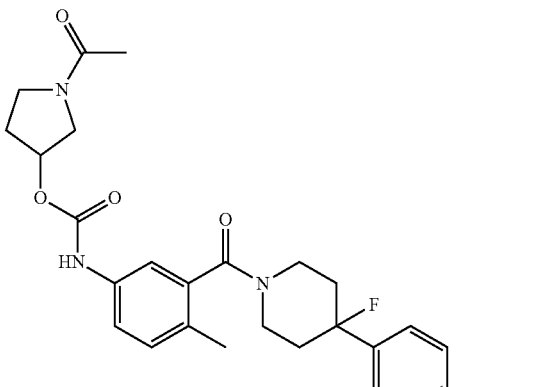

(X-N)

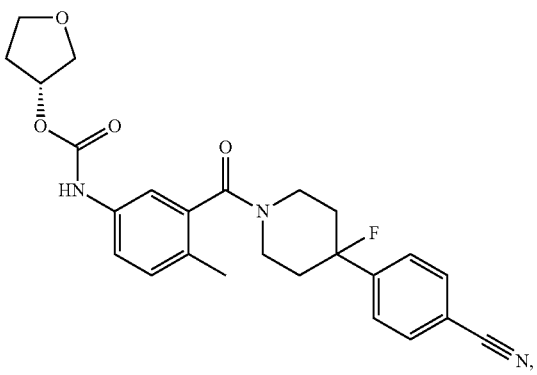

(V-O)

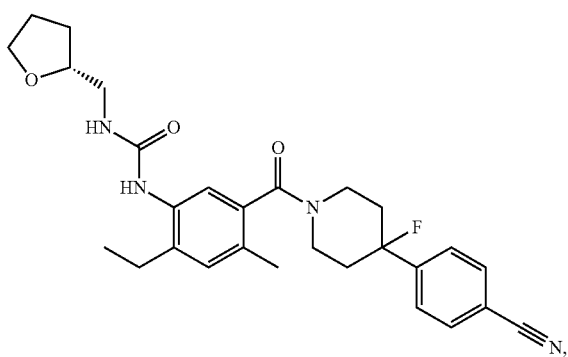

or a pharmaceutically acceptable salt thereof.

In some embodiments of treating or preventing a taxane-resistant tumor or cancer with compounds of Formula (XI) or (XII), the compound is of the Formula (XI-C) or (XI-D):

(XI-C)

![XI-C structure]

(XI-D)

![XI-D structure]

or a pharmaceutically acceptable salt thereof,
wherein:
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{35}$ is hydrogen, $C_{1-6}$ alkyl, or $C_{1-6}$ alkoxy;
$R_{36}$ is hydrogen, $C_{1-6}$ alkyl, $C_{1-6}$ alkoxy, —N($R_{15}R_{16}$), heterocyclyl, or heteroaryl;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino; and
$R_{37}$ and $R_{38}$ are each independently hydrogen, $C_{1-6}$ alkyl, $C_{1-6}$ alkoxy, hydroxyalkyl, heteroaryl, heterocyclyl, or $R_{37}$ and $R_{38}$ taken together with the atoms to which they are attached join together to form a heteroaryl or heterocyclyl.

In some embodiments of treating or preventing a taxane-resistant tumor or cancer with compounds of Formula (XI) or (XII), $R_1$ is hydrogen, cyano, $C_{1-6}$ alkyl, $C_{1-6}$ alkoxy, or —C(=O)N($R_{13}$)($R_{14}$).

In some embodiments of treating or preventing a taxane-resistant tumor or cancer with compounds of Formula (XI) or (XII), $R_1$ is cyano.

In some embodiments of treating or preventing a taxane-resistant tumor or cancer with compounds of Formula (XI) or (XII), $R_2$ is hydrogen or halo.

In some embodiments of treating or preventing a taxane-resistant tumor or cancer with compounds of Formula (XI) or (XII), $R_2$ is hydrogen.

In some embodiments of treating or preventing a taxane-resistant tumor or cancer with compounds of Formula (XI) or (XII), $R_3$ is fluorine.

In some embodiments of treating or preventing a taxane-resistant tumor or cancer with compounds of Formula (XI) or (XII), $R_{21}$ and $R_{22}$ are each independently hydrogen or $C_{1-6}$ alkyl.

In some embodiments of treating or preventing a taxane-resistant tumor or cancer with compounds of Formula (XI) or (XII), $R_{21}$ and $R_{22}$ are each independently $C_{1-6}$ alkyl.

In some embodiments of treating or preventing a taxane-resistant tumor or cancer with compounds of Formula (XI) or (XII), $R_{35}$ is hydrogen.

In some embodiments of treating or preventing a taxane-resistant tumor or cancer with compounds of Formula (XI) or (XII), $R_{34}$ is heteroaryl.

In some embodiments of treating or preventing a taxane-resistant tumor or cancer with compounds of Formula (XI) or (XII), $R_{34}$ is thienyl, pyrrole, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, or benzothiadiazolyl.

In some embodiments of treating or preventing a taxane-resistant tumor or cancer with compounds of Formula (XI) or (XII), $L_{13}$ is N.

In some embodiments of treating or preventing a taxane-resistant tumor or cancer with compounds of Formula (XI) or (XII), $L_{14}$ and $L_{15}$ are each independently CH.

In some embodiments of treating or preventing a taxane-resistant tumor or cancer with compounds of Formula (XI) or (XII), A is N.

In some embodiments of treating or preventing a taxane-resistant tumor or cancer with compounds of Formula (XI) or (XII), A is CH.

In some embodiments of treating or preventing a taxane-resistant tumor or cancer with compounds of Formula (XI) or (XII), the compound is of the Formula (XI-E), (XI-F), (XI-G), (XI-H), or (XI-I):

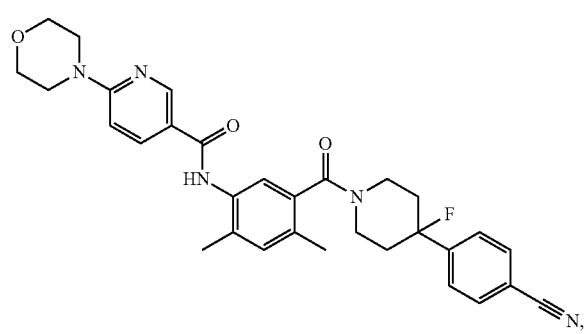

(XI-E)

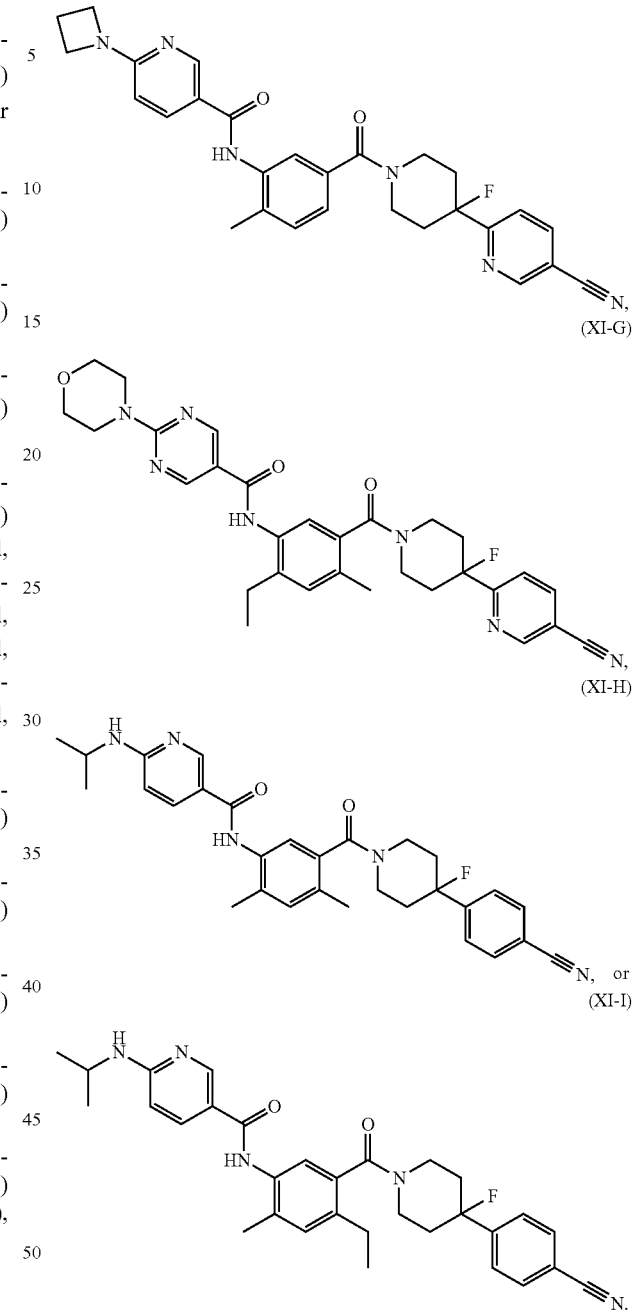

or a pharmaceutically acceptable salt thereof.

In some embodiments of treating or preventing a taxane-resistant tumor or cancer with compounds of Formula (XIII), $R^3$ is H or halogen.

In some embodiments of treating or preventing a taxane-resistant tumor or cancer with compounds of Formula (XIII), $R^1$ is halogen, —CN or $C_1$-$C_2$ haloalkyl.

In some embodiments of treating or preventing a taxane-resistant tumor or cancer with compounds of Formula (XIII), $R^{22}$ is $C_1$-$C_2$ alkyl.

In some embodiments of treating or preventing a taxane-resistant tumor or cancer with compounds of Formula (XIII), $R^{21}$ is cyclobutyl and $R^{22}$ is $C_1$-$C_2$ alkyl.

In some embodiments of treating or preventing a taxane-resistant tumor or cancer with compounds of Formula (XIII), $R^{21}$ is cyclobutyl.

In some embodiments of treating or preventing a taxane-resistant tumor or cancer with compounds of Formula (XIII), $R^3$ is H or F.

In some embodiments of treating or preventing a taxane-resistant tumor or cancer with compounds of Formula (XIII), $R^1$ is —CN.

In some embodiments of treating or preventing a taxane-resistant tumor or cancer with compounds of Formula (XIII), $R^1$ is —CF$_3$.

In some embodiments of treating or preventing a taxane-resistant tumor or cancer with compounds of Formula (XIII), $R^{22}$ is H, methyl or ethyl.

In some embodiments of treating or preventing a taxane-resistant tumor or cancer with compounds of Formula (XIII), $R^{22}$ is H.

In some embodiments of treating or preventing a taxane-resistant tumor or cancer with compounds of Formula (XIII), $R^{22}$ is methyl.

In some embodiments of treating or preventing a taxane-resistant tumor or cancer with compounds of Formula (XIII), $R^{35}$ is —C(O)—NHR$^{351}$.

In some embodiments of treating or preventing a taxane-resistant tumor or cancer with compounds of Formula (XIII), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl or (S)-tetrahydro-2H-pyran-3-yl $R^{351}$ is (R)-(tetrahydrofuran-2-yl)methyl or (S)-(tetrahydrofuran-2-yl)methyl.

$R^1$ is —CN, each $R^2$ is hydrogen, $R^3$ is H or F, $R^{21}$ is $C_3$-$C_4$ cycloalkyl, $R^{22}$ is H, $R^{22}$ is —C(O)—NHR$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some embodiments of treating or preventing a taxane-resistant tumor or cancer with compounds of Formula (XIII), $R^{35}$ is —C(O)—O—R$^{351}$.

In some embodiments of treating or preventing a taxane-resistant tumor or cancer with compounds of Formula (XIII), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some embodiments of treating or preventing a taxane-resistant tumor or cancer with compounds of Formula (XIII), $R^1$ is —CN, each $R^2$ is H, $R^3$ is H or F, $R^{21}$ is $C_3$-$C_4$ cycloalkyl, $R^{22}$ is H, $R^{35}$ is —C(O)—O—R$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some embodiments of treating or preventing a taxane-resistant tumor or cancer with compounds of Formula (XIII), $R^{351}$ is (R)-3-tetrahydrofuranyl or (S)-3-tetrahydrofuranyl.

In some embodiments of treating or preventing a taxane-resistant tumor or cancer with compounds of Formula (XIII), compounds have a structure selected from the group consisting of:

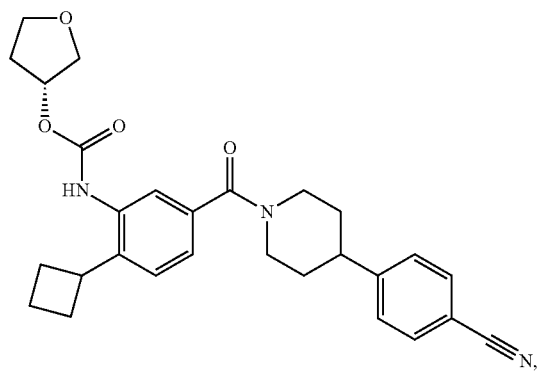

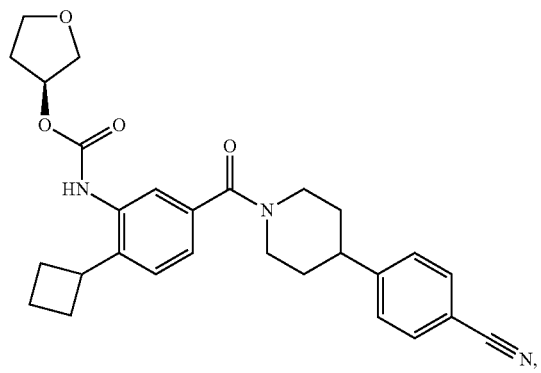

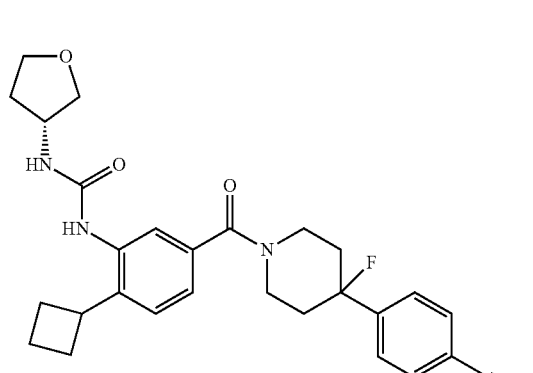

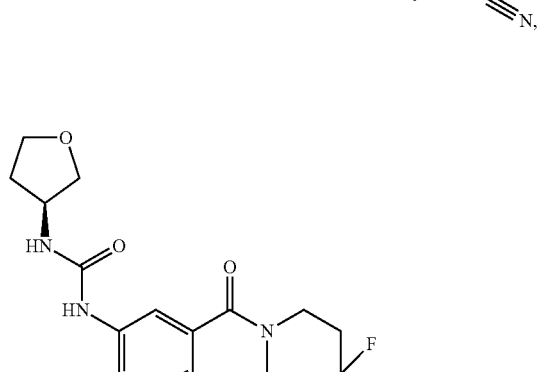

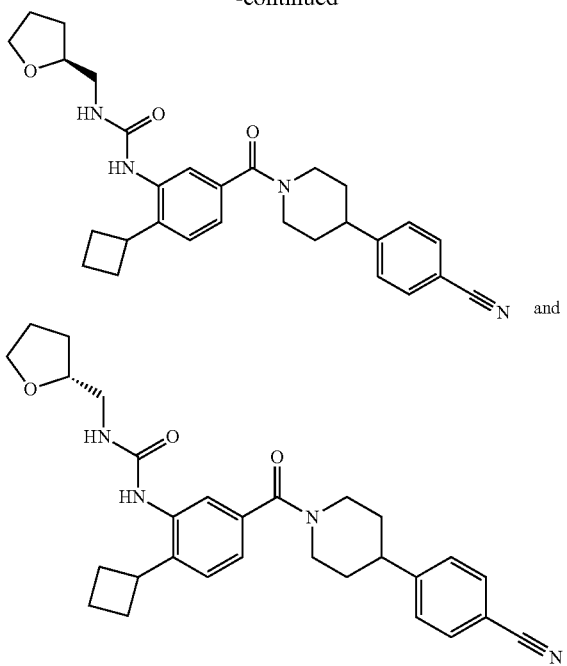

In some embodiments of treating or preventing a taxane-resistant tumor or cancer with compounds of Formula (XIV) or (XV), $R_1$ is hydrogen, cyano $C_{1-6}$ alkyl, $C_{1-6}$ alkoxy, or —C(=O)N($R_{13}$)($R_{14}$).

In some embodiments of treating or preventing a taxane-resistant tumor or cancer with compounds of Formula (XIV) or (XV), $R_1$ is cyano.

In some embodiments of treating or preventing a taxane-resistant tumor or cancer with compounds of Formula (XIV) or (XV), $R_2$ is hydrogen or halo.

In some embodiments of treating or preventing a taxane-resistant tumor or cancer with compounds of Formula (XIV) or (XV), $R_2$ is hydrogen.

In some embodiments of treating or preventing a taxane-resistant tumor or cancer with compounds of Formula (XIV) or (XV), $R_3$ is hydrogen.

In some embodiments of treating or preventing a taxane-resistant tumor or cancer with compounds of Formula (XIV) or (XV), $R_{21}$ and $R_{22}$ are each independently hydrogen or $C_{1-6}$ alkyl.

In some embodiments of treating or preventing a taxane-resistant tumor or cancer with compounds of Formula (XIV) or (XV), $R_{21}$ and $R_{22}$ are each independently $C_{1-6}$ alkyl.

In some embodiments of treating or preventing a taxane-resistant tumor or cancer with compounds of Formula (XIV) or (XV), $R_{39}$ is hydrogen.

In some embodiments of treating or preventing a taxane-resistant tumor or cancer with compounds of Formula (XIV) or (XV), $R_{40}$ is hydrogen.

In some embodiments of treating or preventing a taxane-resistant tumor or cancer with compounds of Formula (XIV) or (XV), $L_{16}$ is N.

In some embodiments of treating or preventing a taxane-resistant tumor or cancer with compounds of Formula (XIV) or (XV), $L_{17}$ is N.

In some embodiments of treating or preventing a taxane-resistant tumor or cancer with compounds of Formula (XIV) or (XV), $L_{18}$ is CH.

In some embodiments of treating or preventing a taxane-resistant tumor or cancer with compounds of Formula (XIV) or (XV), $L_{18}$ is N.

In some embodiments of treating or preventing a taxane-resistant tumor or cancer with compounds of Formula (XIV) or (XV), A is N.

In some embodiments of treating or preventing a taxane-resistant tumor or cancer with compounds of Formula (XIV) or (XV), A is CH.

In some embodiments of treating or preventing a taxane-resistant tumor or cancer with compounds of Formula (XIV) or (XV), $R_{42}$ is $C_{1-6}$ alkyl.

In some embodiments of treating or preventing a taxane-resistant tumor or cancer with compounds of Formula (XIV) or (XV), $R_{41}$ is $C_{1-6}$ alkyl.

In some embodiments of treating or preventing a taxane-resistant tumor or cancer with compounds of Formula (XIV) or (XV), the compound is of the Formula (XIV-C) or (XIV-D):

(XIV-C)

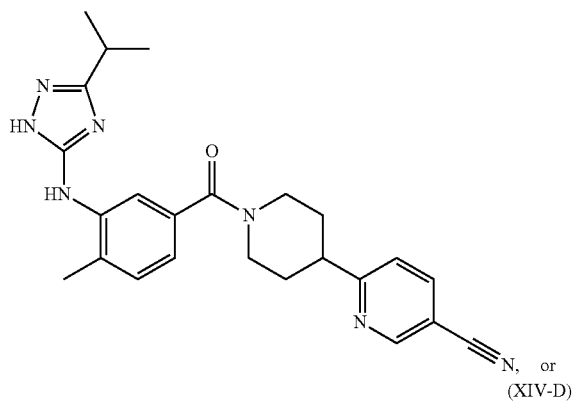

, or (XIV-D)

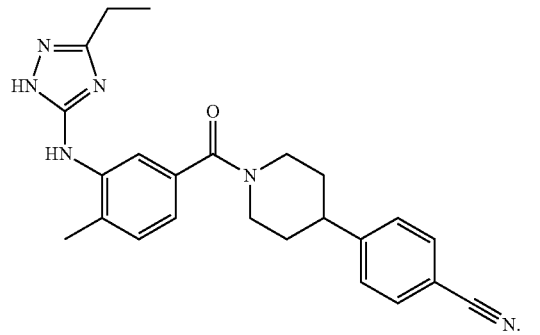

or a pharmaceutically acceptable salt thereof.

In some embodiments of treating or preventing a taxane-resistant tumor or cancer with compounds of Formula (XVI), (XVII), or (XVIII), $R_1$ is hydrogen, cyano. $C_{1-6}$ alkyl, $C_{1-6}$ alkoxy, or —C(=O)NN($R_{13}$)($R_{14}$).

In some embodiments of treating or preventing a taxane-resistant tumor or cancer with compounds of Formula (XVI), (XVII), or (XVIII), $R_1$ is cyano.

In some embodiments of treating or preventing a taxane-resistant tumor or cancer with compounds of Formula (XVI), (XVII), or (XVIII), $R_2$ is hydrogen or halo.

In some embodiments of treating or preventing a taxane-resistant tumor or cancer with compounds of Formula (XVI), (XVII), or (XVIII), $R_2$ is hydrogen.

In some embodiments of treating or preventing a taxane-resistant tumor or cancer with compounds of Formula (XVI), (XVII), or (XVIII), $R_3$ is hydrogen.

In some embodiments of treating or preventing a taxane-resistant tumor or cancer with compounds of Formula (XVI), (XVII), or (XVIII), $R_{21}$ and $R_{22}$ are each independently hydrogen or $C_{1-6}$ alkyl.

In some embodiments of treating or preventing a taxane-resistant tumor or cancer with compounds of Formula (XVI), (XVII), or (XVIII), $R_{21}$ and $R_{22}$ are each independently $C_{1-6}$ alkyl.

In some embodiments of treating or preventing a taxane-resistant tumor or cancer with compounds of Formula (XVI), (XVII), or (XVIII), $R_{39}$ is hydrogen.

In some embodiments of treating or preventing a taxane-resistant tumor or cancer with compounds of Formula (XVI), (XVII), or (XVIII), $L_{19}$ is N.

In some embodiments of treating or preventing a taxane-resistant tumor or cancer with compounds of Formula (XVI), (XVII), or (XVIII), A is N.

In some embodiments of treating or preventing a taxane-resistant tumor or cancer with compounds of Formula (XVI), (XVII), or (XVIII), A is CH.

In some embodiments of treating or preventing a taxane-resistant tumor or cancer with compounds of Formula (XVI), (XVII), or (XVIII), having the following Structure (XVII-D):

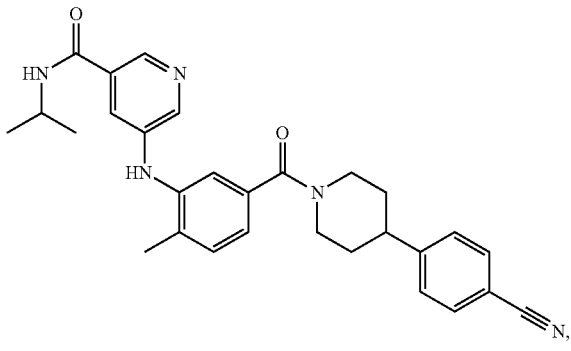

(XVII-D)

or a pharmaceutically acceptable salt thereof.

In some embodiments of treating or preventing a taxane-resistant tumor or cancer with compounds of Formula (XIX), $R^{21}$ is halogen, $C_1$-$C_4$ straight or branched alkyl or $C_3$-$C_5$ cycloalkyl.

In some embodiments of treating or preventing a taxane-resistant tumor or cancer with compounds of Formula (XIX), $R^3$ is H or halogen.

In some embodiments of treating or preventing a taxane-resistant tumor or cancer with compounds of Formula (XIX), $R^1$ is —CN or $C_1$-$C_2$ haloalkyl.

In some embodiments of treating or preventing a taxane-resistant tumor or cancer with compounds of Formula (XIX), $R^3$ is H or F.

In some embodiments of treating or preventing a taxane-resistant tumor or cancer with compounds of Formula (XIX), $R^1$ is —CN.

In some embodiments of treating or preventing a taxane-resistant tumor or cancer with compounds of Formula (XIX), $R^1$ is —CF$_3$.

In some embodiments of treating or preventing a taxane-resistant tumor or cancer with compounds of Formula (XIX), n is 1.

In some embodiments of treating or preventing a taxane-resistant tumor or cancer with compounds of Formula (XIX), n is 2.

In some embodiments of treating or preventing a taxane-resistant tumor or cancer with compounds of Formula (XIX), m is 1.

In some embodiments of treating or preventing a taxane-resistant tumor or cancer with compounds of Formula (XIX), m is 2.

In some embodiments of treating or preventing a taxane-resistant tumor or cancer with compounds of Formula (XIX), $R^{21}$ is $C_1$-$C_2$ alkyl or $C_3$-$C_5$ cycloalkyl and $R^{22}$ is $C_1$-$C_2$ alkyl.

In some embodiments of treating or preventing a taxane-resistant tumor or cancer with compounds of Formula (XIX), $R^{21}$ is $C_3$-$C_5$ cycloalkyl and $R^{22}$ is $C_1$-$C_2$ alkyl.

In some embodiments of treating or preventing a taxane-resistant tumor or cancer with compounds of Formula (XIX), n is 2, m is 1, and $L^3$ is —N—C(O)—O—($C_1$-$C_2$ alkyl).

In some embodiments of treating or preventing a taxane-resistant tumor or cancer with compounds of Formula (XIX), $L^3$ is NR$^{50}$; R$^{50}$ is $C_1$-$C_2$ alkyl; R$^{21}$ is cyclobutyl; R$^{22}$ is H or methyl; R$^3$ is H; R$^1$ is —CN; m is 2 and n is 1 or 2.

In some embodiments of treating or preventing a taxane-resistant tumor or cancer with compounds of Formula (XIX), n is 2, m is 1, $L^3$ is O and s is 0.

In some embodiments of treating or preventing a taxane-resistant tumor or cancer with compounds of Formula (XIX), $R^{22}$ is H, methyl or ethyl.

In some embodiments of treating or preventing a taxane-resistant tumor or cancer with compounds of Formula (XIX), $R^{22}$ is methyl.

In some embodiments of treating or preventing a taxane-resistant tumor or cancer with compounds of Formula (XIX), $R^{22}$ is H.

In some embodiments of treating or preventing a taxane-resistant tumor or cancer with compounds of Formula (XIX), $R^1$ is —CN, each $R^2$ is H, $R^3$ is H or F, $R^{21}$ is $C_3$-$C_4$ cycloalkyl, $R^{22}$ is methyl, n is 2 and $L^3$ is NR$^{50}$ where R$^{50}$ is methyl or ethyl.

In some embodiments of treating or preventing a taxane-resistant tumor or cancer with compounds of Formula (XIX), $R^1$ is —CN, each $R^2$ is H, $R^3$ is H or F, $R^{21}$ is $C_3$-$C_4$ cycloalkyl, $R^{22}$ is methyl, n is 2 and $L^3$ is O.

In some embodiments of treating or preventing a taxane-resistant tumor or cancer with compounds of Formula (XIX), the compound has a structure selected from the group consisting of:

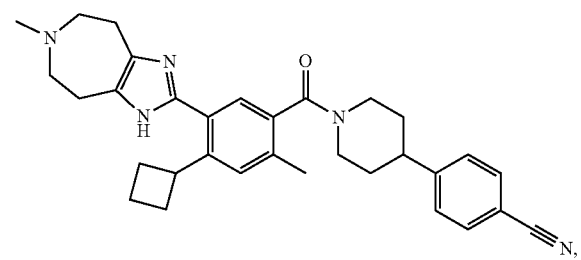

-continued

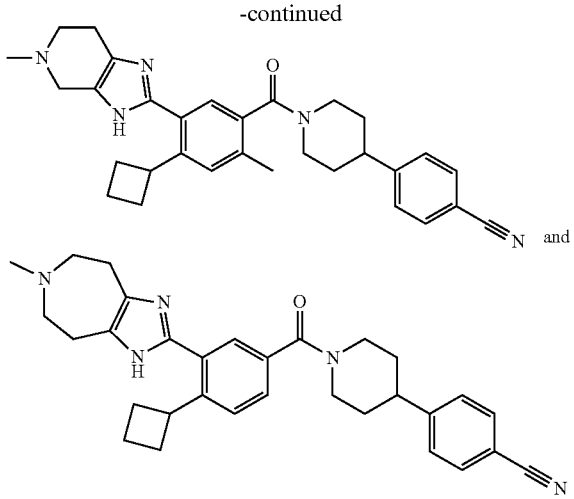

and

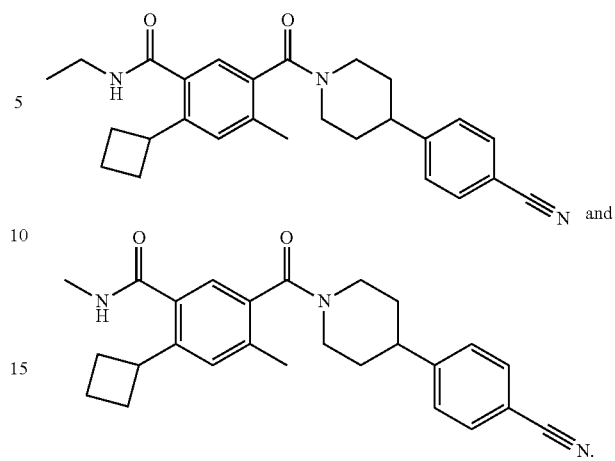

and

In some embodiments of treating or preventing a taxane-resistant tumor or cancer with compounds of Formula (XX), $R^3$ is H or halogen.

In some embodiments of treating or preventing a taxane-resistant tumor or cancer with compounds of Formula (XX), $R^1$ is halogen, —CN or $C_1$-$C_2$ haloalkyl.

In some embodiments of treating or preventing a taxane-resistant tumor or cancer with compounds of Formula (XX), $R^{21}$ is $C_3$-$C_4$ cycloalkyl and $R^{22}$ is $C_1$-$C_2$ alkyl.

In some embodiments of treating or preventing a taxane-resistant tumor or cancer with compounds of Formula (XX), $R^{21}$ is cyclobutyl and $R^{22}$ is $C_1$-$C_2$ alkyl.

In some embodiments of treating or preventing a taxane-resistant tumor or cancer with compounds of Formula (XX), $R^{21}$ is cyclobutyl.

In some embodiments of treating or preventing a taxane-resistant tumor or cancer with compounds of Formula (XX), $R^3$ is H or F.

In some embodiments of treating or preventing a taxane-resistant tumor or cancer with compounds of Formula (XX), $R^1$ is —CN.

In some embodiments of treating or preventing a taxane-resistant tumor or cancer with compounds of Formula (XX), $R^1$ is —$CF_3$.

In some embodiments of treating or preventing a taxane-resistant tumor or cancer with compounds of Formula (XX), $R^{22}$ is H, methyl or ethyl.

In some embodiments of treating or preventing a taxane-resistant tumor or cancer with compounds of Formula (XX), $R^{22}$ is H.

In some embodiments of treating or preventing a taxane-resistant tumor or cancer with compounds of Formula (XX), $R^{22}$ is methyl.

In some embodiments of treating or preventing a taxane-resistant tumor or cancer with compounds of Formula (XX), $R^1$ is —CN, each $R^2$ is H, $R^3$ is H or F, $R^{21}$ is cyclobutyl, $R^{22}$ is methyl and $R^{351}$ is methyl or ethyl.

In some embodiments of treating or preventing a taxane-resistant tumor or cancer with compounds of Formula (XX), the compound has a structure selected from the group consisting of:

In some embodiments of treating or preventing a taxane-resistant tumor or cancer with compounds of Formula (XXI), L-Ar is

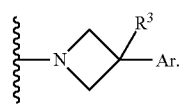

In some embodiments of treating or preventing a taxane-resistant tumor or cancer with compounds of Formula (XXI), L-Ar is

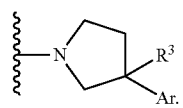

In some embodiments of treating or preventing a taxane-resistant tumor or cancer with compounds of Formula (XXI), L-Ar is

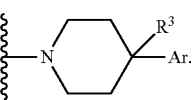

In some embodiments of treating or preventing a taxane-resistant tumor or cancer with compounds of Formula (XXI), $R^3$ is H.

In some embodiments of treating or preventing a taxane-resistant tumor or cancer with compounds of Formula (XXI), $R^1$ is —CN or —O—($C_1$-$C_4$ alkyl), wherein when $R^1$ is not —CN, $R^1$ is optionally substituted with one or more halogen.

In some embodiments of treating or preventing a taxane-resistant tumor or cancer with compounds of Formula (XXI), $R^1$ is —CN.

In some embodiments of treating or preventing a taxane-resistant tumor or cancer with compounds of Formula (XXI), $R^1$ is —O—($C_1$-$C_4$ alkyl) optionally substituted with one or more halogen.

In some embodiments of treating or preventing a taxane-resistant tumor or cancer with compounds of Formula (XXI), $R^2$ is hydrogen.

In some embodiments of treating or preventing a taxane-resistant tumor or cancer with compounds of Formula (XXI), R²¹ is C₁-C₄ alkyl.

In some embodiments of treating or preventing a taxane-resistant tumor or cancer with compounds of Formula (XXI), R²² is H or C₁-C₂ alkyl.

In some embodiments of treating or preventing a taxane-resistant tumor or cancer with compounds of Formula (XXI), R²⁴ is —O—(C₁-C₄ alkyl) optionally substituted with one or more hydroxyl or halogen.

In some embodiments of treating or preventing a taxane-resistant tumor or cancer with compounds of Formula (XXI), R²⁴ is —O—(C₁-C₄ alkyl) optionally substituted with one or more hydroxyl.

In some embodiments of treating or preventing a taxane-resistant tumor or cancer with compounds of Formula (XXI), R²⁵ is —CH₃.

In some embodiments of treating or preventing a taxane-resistant tumor or cancer with compounds of Formula (XXI), the compound has a structure selected from the group consisting of:

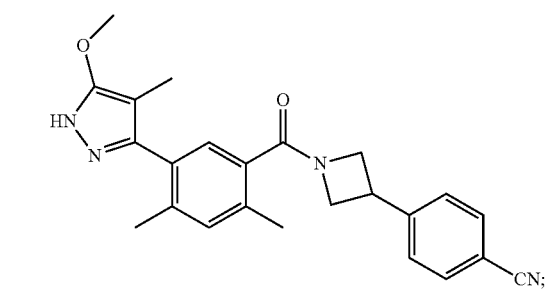

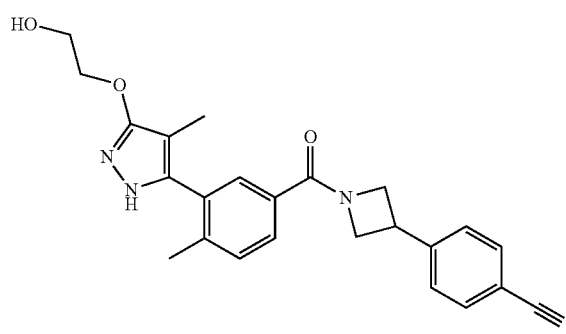

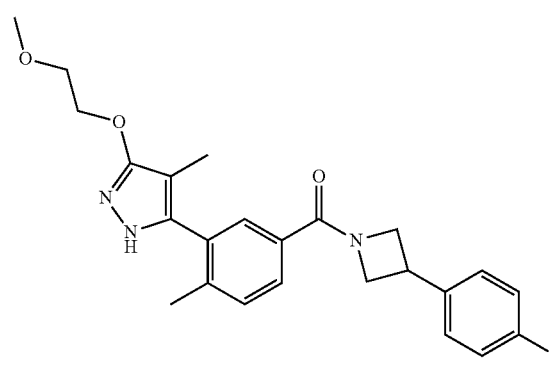

-continued

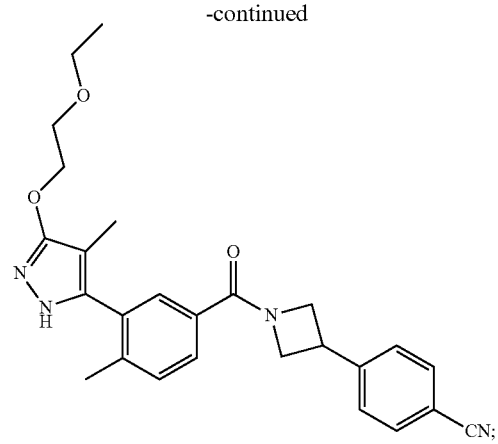

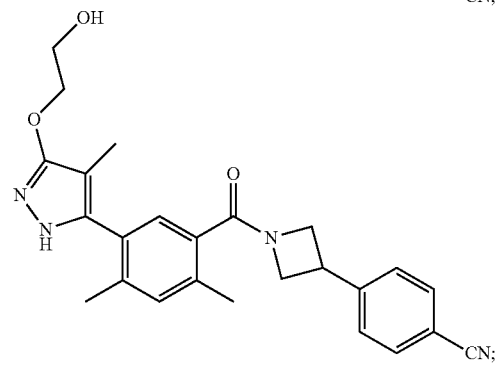

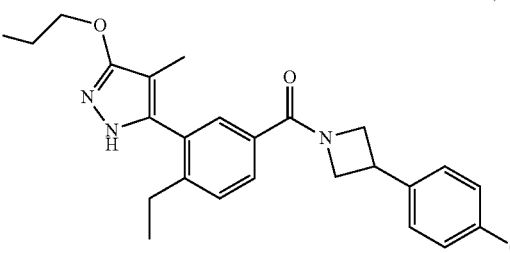

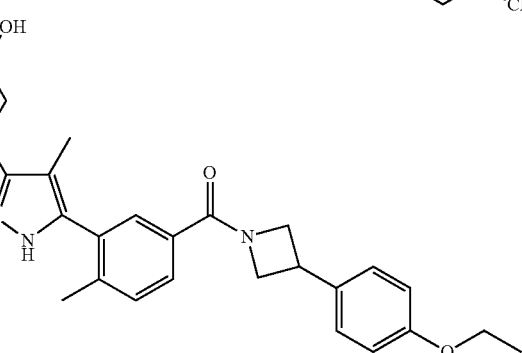

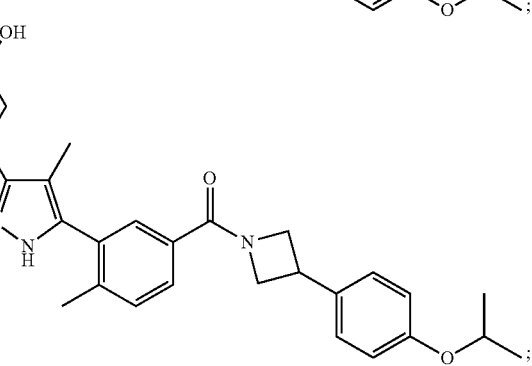

75
-continued
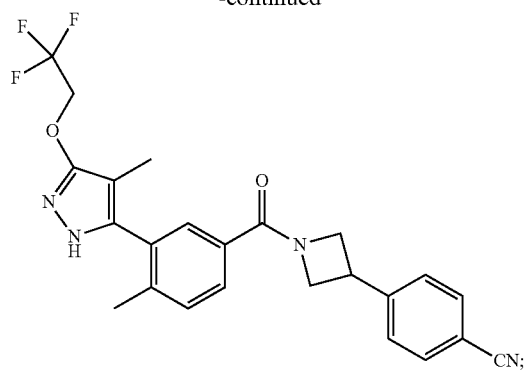
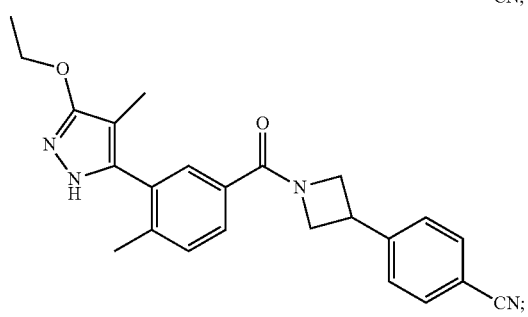
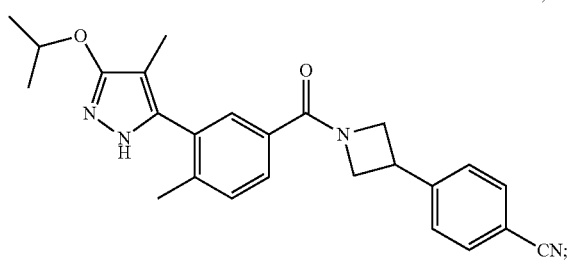
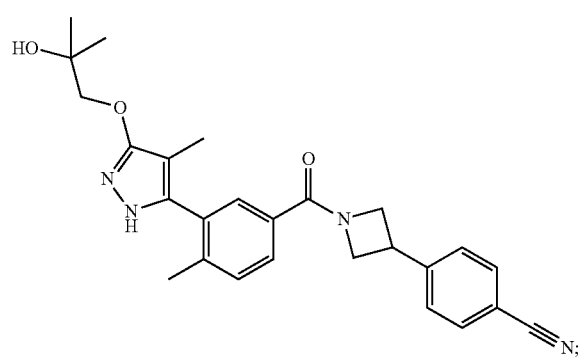
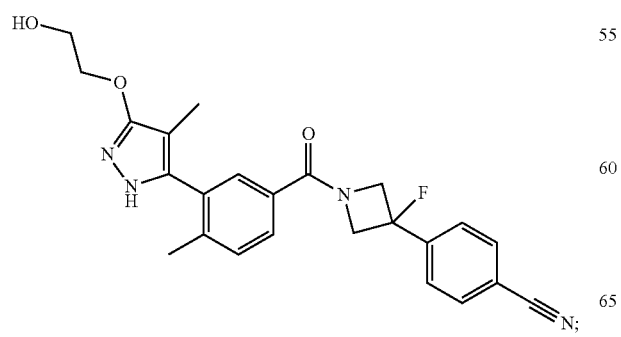
76
-continued
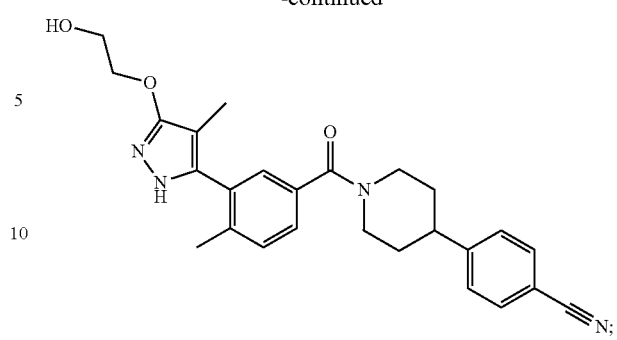
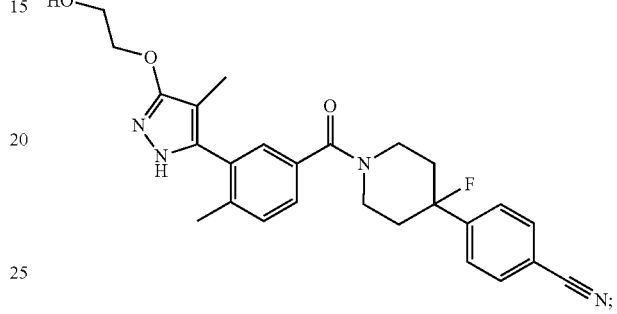
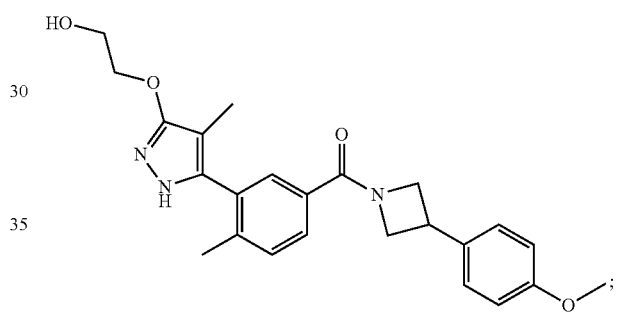
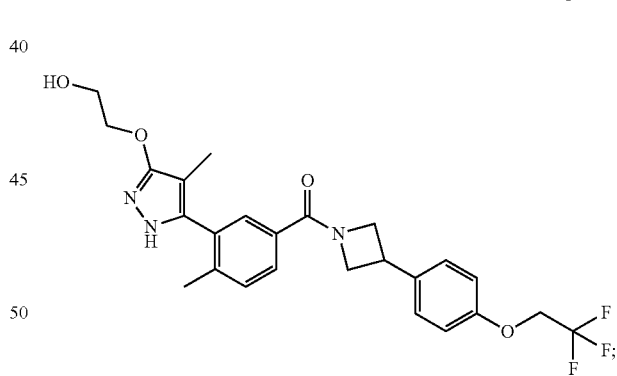
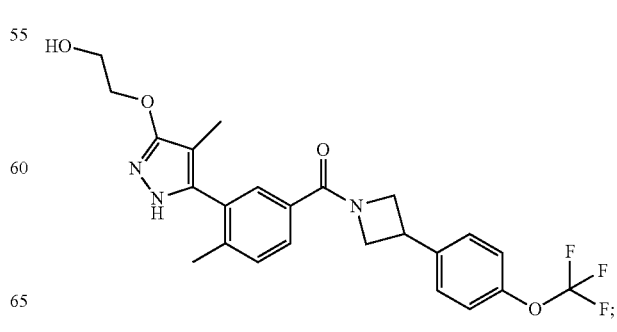

-continued

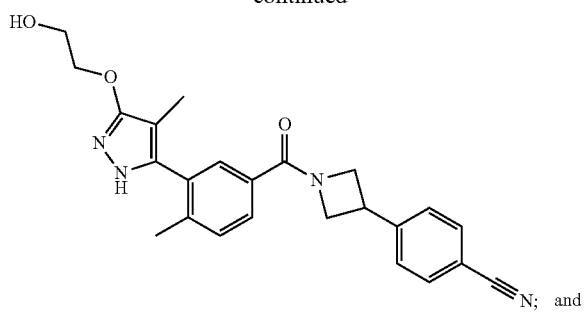
and

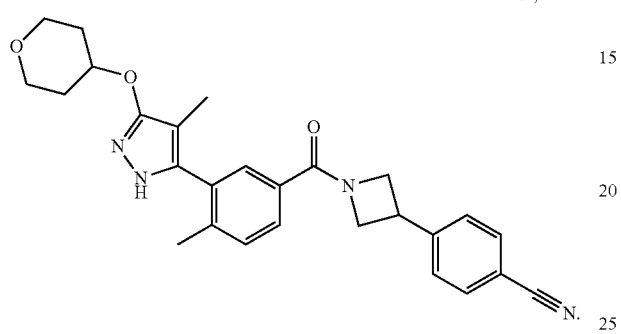

In some embodiments of treating or preventing a taxane-resistant tumor or cancer with compounds of Formula (XXII), $L^3$ is —CH$_2$—, CHR$^{50}$, —O—, —NR$^{50}$—, —NC(O)R$^{50}$— or —NC(O)OR$^{50}$—, wherein R$^{50}$ is optionally substituted C$_1$-C$_6$ alkyl, optionally substituted C$_3$-C$_5$ cycloalkyl or optionally substituted 4- to 6-membered heterocycle;

n is 1, 2 or 3;

m is 1 or 2 with the proviso that n+m≥3;

L-Ar is

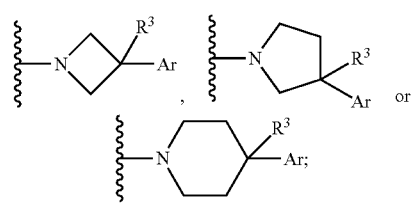

Ar is

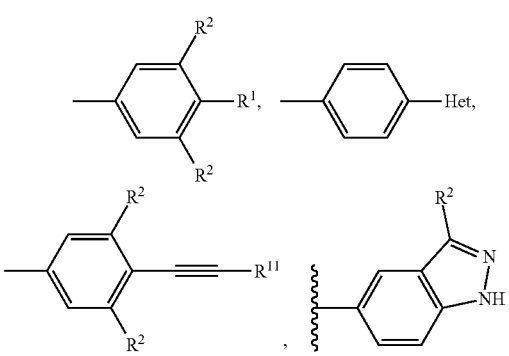

-continued

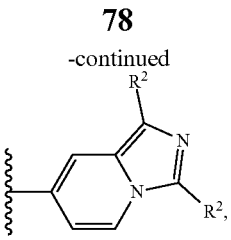

with the proviso that when L-Ar is

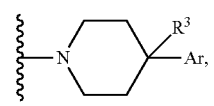

Ar is not

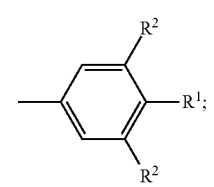

Het is a optionally substituted 5- to 6-membered heteroaryl;

R$^1$ is H, —CN, halogen, optionally substituted C$_1$-C$_4$ alkyl, —O-(optionally substituted C$_3$-C$_5$ cycloalkyl), —O-(optionally substituted 4- to 6-membered heterocycle) or —O-(optionally substituted C$_1$-C$_4$ alkyl), wherein when R$^1$ is not H, —CN or halogen, R$^1$ is optionally substituted with one or more halogens;

each R$^2$ is independently hydrogen, halogen or optionally substituted C$_1$-C$_4$ alkyl;

R$^3$ is H or F;

R$^{11}$ is H or —CH$_3$;

R$^{21}$ is H, halogen, optionally substituted C$_1$-C$_4$ alkyl, optionally substituted C$_3$-C$_5$ cycloalkyl or an optionally substituted 4- to 6-membered heterocycle; and R$^{22}$ is H, halogen or optionally substituted C$_1$-C$_2$ alkyl.

In some embodiments of treating or preventing a taxane-resistant tumor or cancer with compounds of Formula (XXII), L-Ar is

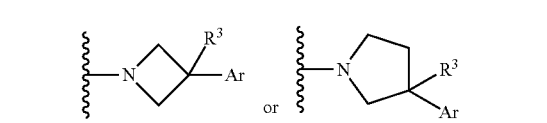

and Ar is

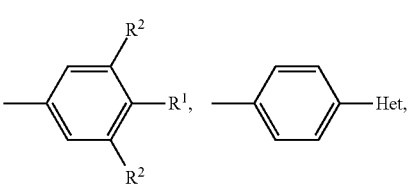

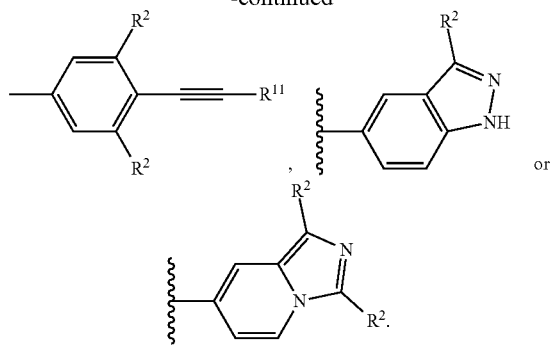

In some embodiments of treating or preventing a taxane-resistant tumor or cancer with compounds of Formula (XXII), L-Ar is

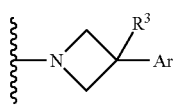

and Ar is

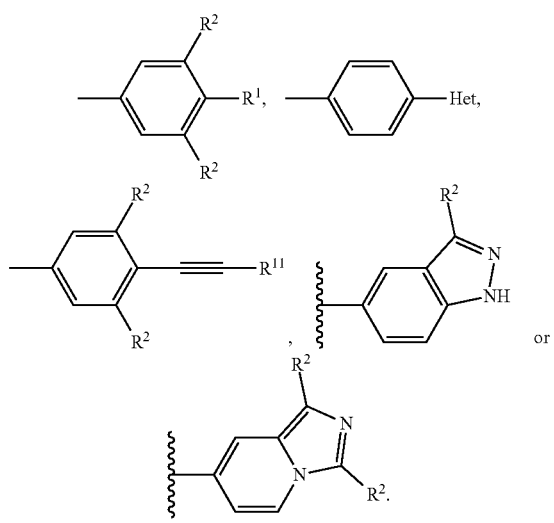

In some embodiments of treating or preventing a taxane-resistant tumor or cancer with compounds of Formula (XXII), $R^1$ is H, —CN, —$C_1$-$C_4$ alkyl, —O—($C_3$-$C_5$ cycloalkyl), —O-(4- to 6-membered heterocycle) or —O—($C_1$-$C_4$ alkyl) wherein when $R^1$ is not H or —CN, $R^1$ is optionally substituted with one or more halogens.

In some embodiments of treating or preventing a taxane-resistant tumor or cancer with compounds of Formula (XXII), $R^1$ is halogen, —CN or $C_1$-$C_2$ haloalkyl.

In some embodiments of treating or preventing a taxane-resistant tumor or cancer with compounds of Formula (XXII), $R^1$ is —CN or $C_1$-$C_2$ haloalkyl.

In some embodiments of treating or preventing a taxane-resistant tumor or cancer with compounds of Formula (XXII), $R^1$ is —CN.

In some embodiments of treating or preventing a taxane-resistant tumor or cancer with compounds of Formula (XXII), $R^1$ is —Cl.

In some embodiments of treating or preventing a taxane-resistant tumor or cancer with compounds of Formula (XXII), $R^2$ is H.

In some embodiments of treating or preventing a taxane-resistant tumor or cancer with compounds of Formula (XXII), $R^{21}$ is halogen, $C_1$-$C_4$ alkyl, $C_3$-$C_5$ cycloalkyl or 4- to 6-membered heterocycle.

In some embodiments of treating or preventing a taxane-resistant tumor or cancer with compounds of Formula (XXII), $R^{21}$ is $C_1$-$C_2$ alkyl or $C_3$-$C_5$ cycloalkyl.

In some embodiments of treating or preventing a taxane-resistant tumor or cancer with compounds of Formula (XXII), $R^{21}$ is $C_3$-$C_5$ cycloalkyl.

In some embodiments of treating or preventing a taxane-resistant tumor or cancer with compounds of Formula (XXII), $R^{22}$ is H or $C_1$-$C_2$ alkyl.

In some embodiments of treating or preventing a taxane-resistant tumor or cancer with compounds of Formula (XXII), $R^{22}$ is H.

In some embodiments of treating or preventing a taxane-resistant tumor or cancer with compounds of Formula (XXII), $R^{22}$ is $C_1$-$C_2$ alkyl.

In some embodiments of treating or preventing a taxane-resistant tumor or cancer with compounds of Formula (XXII), $R^{22}$ is —$CH_3$.

In some embodiments of treating or preventing a taxane-resistant tumor or cancer with compounds of Formula (XXII), $L^3$ is —N($CH_3$)—.

In some embodiments of treating or preventing a taxane-resistant tumor or cancer with compounds of Formula (XXII), n is 2 and m is 2.

In some embodiments of treating or preventing a taxane-resistant tumor or cancer with compounds of Formula (XXII), n is 1 or 2.

In some embodiments of treating or preventing a taxane-resistant tumor or cancer with compounds of Formula (XXII), n is 1 and m is 2.

In some embodiments of treating or preventing a taxane-resistant tumor or cancer with compounds of Formula (XXII), $R^{21}$ is $C_1$-$C_2$ alkyl or $C_3$-$C_5$ cycloalkyl and $R^{22}$ is $C_1$-$C_2$ alkyl.

In some embodiments of treating or preventing a taxane-resistant tumor or cancer with compounds of Formula (XXII), $R^{21}$ is $C_1$-$C_2$ alkyl or $C_3$-$C_5$ cycloalkyl and $R^{22}$ is H or $C_1$-$C_2$ alkyl.

In some embodiments of treating or preventing a taxane-resistant tumor or cancer with compounds of Formula (XXII), $R^{21}$ is $C_3$-$C_5$ cycloalkyl and $R^{22}$ is H or $C_1$-$C_2$ alkyl.

In some embodiments of treating or preventing a taxane-resistant tumor or cancer with compounds of Formula (XXII), $R^{21}$ is $C_3$-$C_5$ cycloalkyl and $R^{22}$ is H or —$CH_3$.

In some embodiments of treating or preventing a taxane-resistant tumor or cancer with compounds of Formula (XXIII), L-Ar is

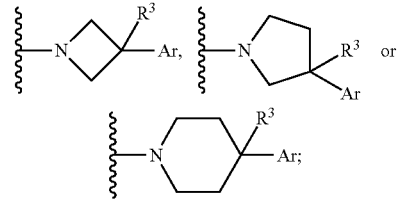

Ar is

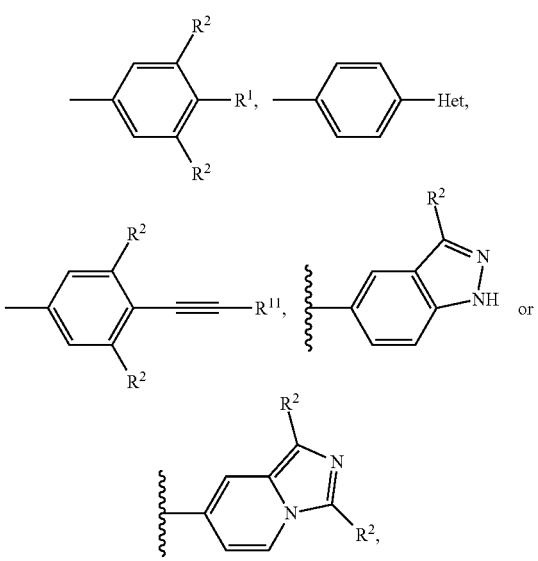

with the proviso that when L-Ar is

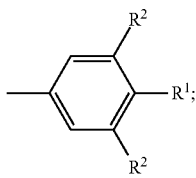

Ar is not

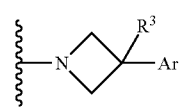

Het is an optionally substituted 5- to 6-membered heteroaryl;

R¹ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when R¹ is not H, —CN or halogen, R¹ is optionally substituted with one or more halogens;

each R² is independently hydrogen, halogen or optionally substituted $C_1$-$C_4$ alkyl;

R³ is H or F;

R¹¹ is H or —CH₃;

R²¹ is H, halogen, optionally substituted $C_1$-$C_4$ alkyl, optionally substituted $C_3$-$C_5$ cycloalkyl or optionally substituted 4- to 6-membered heterocycle;

R²² is H, halogen or optionally substituted $C_1$-$C_2$ alkyl; and

R²⁴ is H, optionally substituted $C_1$-$C_4$ alkyl, -(optionally substituted $C_1$-$C_4$ alkyl)-OH, -(optionally substituted $C_1$-$C_4$ alkyl)-N(R²⁴¹)₂, -(optionally substituted $C_1$-$C_4$ alkyl)$_t$-O$_t$-(optionally substituted $C_3$-$C_5$ cycloalkyl), -(optionally substituted $C_1$-$C_4$ alkyl)$_t$-O$_t$-(optionally substituted 4- to 6-membered heterocycle) or -(optionally substituted $C_1$-$C_4$ alkyl)$_t$-O-(optionally substituted $C_1$-$C_4$ alkyl), wherein:

t is 0 or 1; and

R²⁴¹ is H or optionally substituted $C_1$-$C_2$ alkyl.

In some embodiments of treating or preventing a taxane-resistant tumor or cancer with compounds of Formula (XXIII), L-Ar is

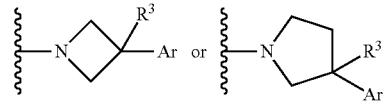

and Ar is

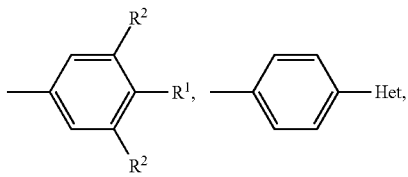

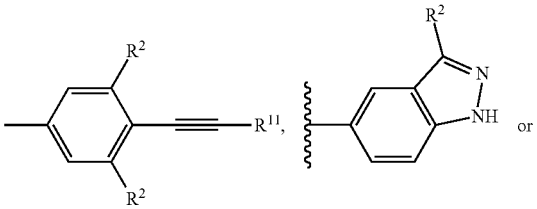

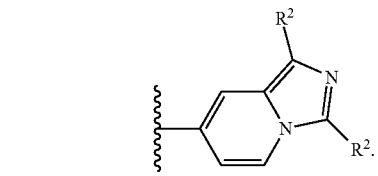

In some embodiments of treating or preventing a taxane-resistant tumor or cancer with compounds of Formula (XXIII), L-Ar is

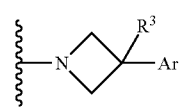

and Ar is

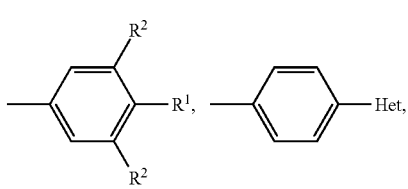

-continued

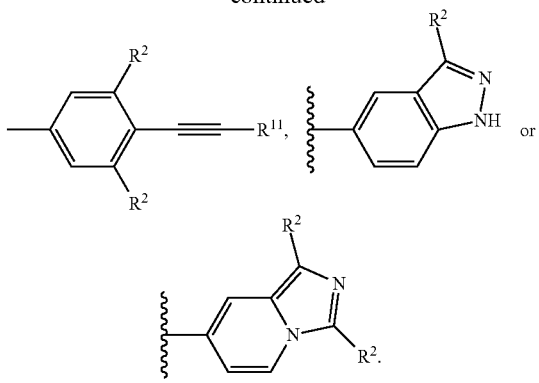

In some embodiments of treating or preventing a taxane-resistant tumor or cancer with compounds of Formula (XXIII), Ar is

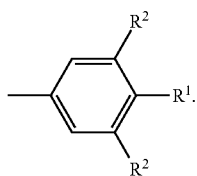

In some embodiments of treating or preventing a taxane-resistant tumor or cancer with compounds of Formula (XXIII), $R^1$ is halogen, —CN or $C_1$-$C_2$ haloalkyl.

In some embodiments of treating or preventing a taxane-resistant tumor or cancer with compounds of Formula (XXIII), $R^1$ is —CN.

In some embodiments of treating or preventing a taxane-resistant tumor or cancer with compounds of Formula (XXIII), $R^2$ is H.

In some embodiments of treating or preventing a taxane-resistant tumor or cancer with compounds of Formula (XXIII), $R^{21}$ is halogen, $C_1$-$C_4$ alkyl, $C_3$-$C_5$ cycloalkyl or 4- to 6-membered heterocycle.

In some embodiments of treating or preventing a taxane-resistant tumor or cancer with compounds of Formula (XXIII), $R^{21}$ is H, $C_1$-$C_4$ alkyl, $C_3$-$C_5$ cycloalkyl or 4- to 6-membered heterocycle.

In some embodiments of treating or preventing a taxane-resistant tumor or cancer with compounds of Formula (XXIII), $R^{21}$ is $C_1$-$C_2$ alkyl or $C_3$-$C_5$ cycloalkyl.

In some embodiments of treating or preventing a taxane-resistant tumor or cancer with compounds of Formula (XXIII), $R^{21}$ is $C_1$-$C_2$ alkyl.

In some embodiments of treating or preventing a taxane-resistant tumor or cancer with compounds of Formula (XXIII), $R^{21}$ is $C_3$-$C_5$ cycloalkyl.

In some embodiments of treating or preventing a taxane-resistant tumor or cancer with compounds of Formula (XXIII), $R^{22}$ is H or $C_1$-$C_2$ alkyl.

In some embodiments of treating or preventing a taxane-resistant tumor or cancer with compounds of Formula (XXIII), $R^{22}$ is H.

In some embodiments of treating or preventing a taxane-resistant tumor or cancer with compounds of Formula (XXIII), $R^{22}$ is $C_1$-$C_2$ alkyl.

In some embodiments of treating or preventing a taxane-resistant tumor or cancer with compounds of Formula (XXIII), $R^{22}$ is —CH$_3$.

In some embodiments of treating or preventing a taxane-resistant tumor or cancer with compounds of Formula (XXIII), $R^{24}$ is $C_1$-$C_4$ alkyl or —($C_1$-$C_4$ alkyl)$_t$-O—($C_1$-$C_4$ alkyl).

In some embodiments of treating or preventing a taxane-resistant tumor or cancer with compounds of Formula (XXIII), $R^{24}$ is —($C_1$-$C_2$ alkyl)$_t$-O—($C_1$-$C_2$ alkyl).

In some embodiments of treating or preventing a taxane-resistant tumor or cancer with compounds of Formula (XXIII), $R^{24}$ is $C_1$-$C_4$ alkyl or —($C_1$-$C_4$ alkyl)$_t$-O—($C_1$-$C_4$ alkyl) wherein t is 0 or 1.

In some embodiments of treating or preventing a taxane-resistant tumor or cancer with compounds of Formula (XXIII), $R^{21}$ is $C_1$-$C_2$ alkyl or $C_3$-$C_5$ cycloalkyl and $R^{22}$ is H or $C_1$-$C_2$ alkyl.

In some embodiments of treating or preventing a taxane-resistant tumor or cancer with compounds of Formula (XXIII), $R^{21}$ is $C_1$-$C_2$ alkyl or $C_3$-$C_5$ cycloalkyl and $R^{22}$ is $C_1$-$C_2$ alkyl.

In some embodiments of treating or preventing a taxane-resistant tumor or cancer with compounds of Formula (XXIII), $R^{21}$ is $C_1$-$C_2$ alkyl or $C_3$-$C_5$ cycloalkyl and $R^{22}$ is —CH$_3$.

In some embodiments of treating or preventing a taxane-resistant tumor or cancer with compounds of Formula (XXIII), $R^{21}$ is $C_1$-$C_2$ alkyl or $C_3$-$C_5$ cycloalkyl and $R^{22}$ is H.

In some embodiments of treating or preventing a taxane-resistant tumor or cancer with compounds of Formula (XXIII), $R^{21}$ is $C_3$-$C_5$ cycloalkyl and $R^{22}$ is H or $C_1$-$C_2$ alkyl.

In some embodiments of treating or preventing a taxane-resistant tumor or cancer with compounds of Formula (XXIII), $R^{21}$ is $C_3$-$C_5$ cycloalkyl and $R^{22}$ is H or —CH$_3$.

In some embodiments of treating or preventing a taxane-resistant tumor or cancer with compounds of Formula (XXIII), $R^{21}$ is $C_3$-$C_5$ cycloalkyl and $R^{22}$ is $C_1$-$C_2$ alkyl.

In some embodiments of treating or preventing a taxane-resistant tumor or cancer with compounds of Formula (XXIII), $R^{21}$ is $C_3$-$C_5$ cycloalkyl and $R^{22}$ is —CH$_3$.

In some embodiments of treating or preventing a taxane-resistant tumor or cancer with compounds of Formula (XXIII), $R^{21}$ is $C_3$-$C_5$ cycloalkyl and $R^{22}$ is H.

In some embodiments of treating or preventing a taxane-resistant tumor or cancer with compounds of Formula (XXIII), $R^{24}$ is —($C_1$-$C_2$ alkyl)$_t$-O—($C_1$-$C_2$ alkyl) and wherein t is 0 or 1.

In some embodiments of treating or preventing a taxane-resistant tumor or cancer with compounds of Formula (XXIII), $R^1$ is —CN and $R^2$ is H.

In some embodiments of treating or preventing a taxane-resistant tumor or cancer with compounds of Formula (XXIV), L-Ar is

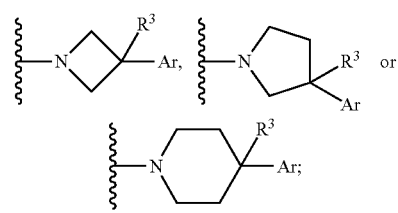

Ar is

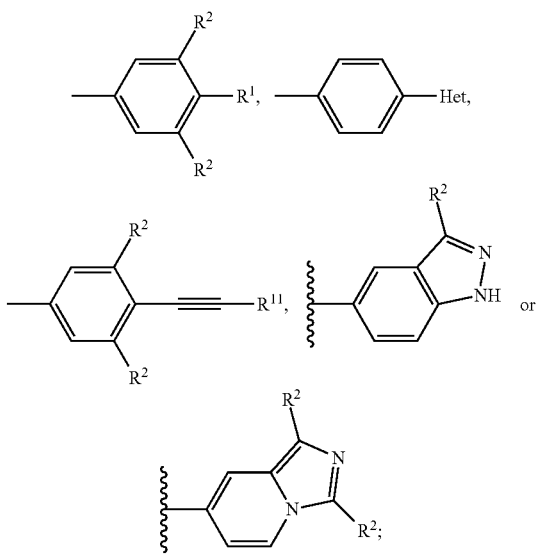

Het is an optionally substituted 5- to 6-membered heteroaryl;

$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens;

each $R^2$ is independently hydrogen, halogen or optionally substituted $C_1$-$C_4$ alkyl;

$R^3$ is H or F:

$R^{11}$ is H or —$CH_3$;

$R^{21}$ is H, halogen, optionally substituted $C_1$-$C_4$ alkyl, optionally substituted $C_3$-$C_5$ cycloalkyl or optionally substituted 4- to 6-membered heterocycle;

$R^{22}$ is H, halogen or optionally substituted $C_1$-$C_2$ alkyl;

$R^{24}$ is H, —CN, -(optionally substituted $C_1$-$C_4$ alkyl)-CN, optionally substituted $C_1$-$C_4$ alkyl, -(optionally substituted $C_1$-$C_4$ alkyl)-OH.

-(optionally substituted $C_1$-$C_4$ alkyl)-N($R^{241}$)$_2$,
-(optionally substituted $C_1$-$C_4$ alkyl)$_t$-O$_u$-(optionally substituted $C_3$-$C_6$ cycloalkyl),
-(optionally substituted $C_1$-$C_4$ alkyl)$_t$-O$_u$-(optionally substituted 4- to 6-membered heterocycle) or
-(optionally substituted $C_1$-$C_4$ alkyl)-O-(optionally substituted $C_1$-$C_4$ alkyl), wherein:
  t is 0 or 1;
  u is 0 or 1;
  with the proviso that when u is 1, t is 1; and
  $R^{241}$ is H or optionally substituted $C_1$-$C_2$ alkyl; and $R^{25}$ is halogen, —CN, -(optionally substituted $C_1$-$C_4$ alkyl)-CN, optionally substituted methyl, optionally substituted ethyl or optionally substituted cyclopropyl.

In some embodiments of treating or preventing a taxane-resistant tumor or cancer with compounds of Formula (XXIV), L-Ar is

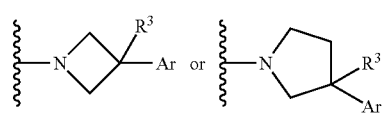

and Ar is

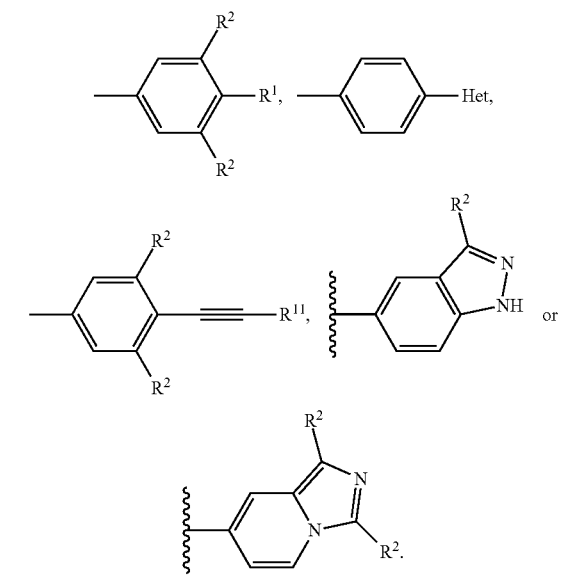

In some embodiments of treating or preventing a taxane-resistant tumor or cancer with compounds of Formula (XXIV), L-Ar is

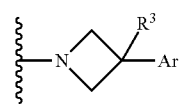

an Ar is

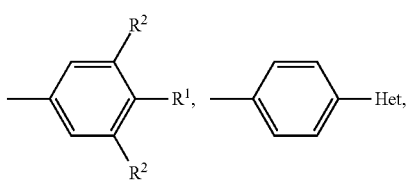

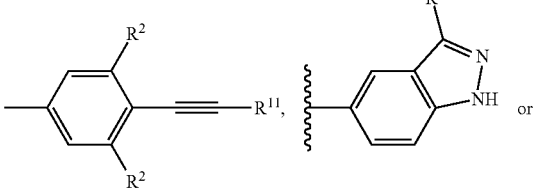

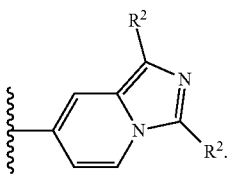

In some embodiments of treating or preventing a taxane-resistant tumor or cancer with compounds of Formula (XXIV), Ar is

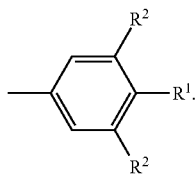

In some embodiments of treating or preventing a taxane-resistant tumor or cancer with compounds of Formula (XXIV), $R^1$ is halogen, —CN or $C_1$-$C_2$ haloalkyl.

In some embodiments of treating or preventing a taxane-resistant tumor or cancer with compounds of Formula (XXIV), $R^1$ is —CN.

In some embodiments of treating or preventing a taxane-resistant tumor or cancer with compounds of Formula (XXIV), $R^2$ is H.

In some embodiments of treating or preventing a taxane-resistant tumor or cancer with compounds of Formula (XXIV), $R^{21}$ is halogen, $C_1$-$C_4$ alkyl or $C_3$-$C_5$ cycloalkyl.

In some embodiments of treating or preventing a taxane-resistant tumor or cancer with compounds of Formula (XXIV), $R^{21}$ is $C_1$-$C_4$ alkyl or $C_3$-$C_5$ cycloalkyl.

In some embodiments of treating or preventing a taxane-resistant tumor or cancer with compounds of Formula (XXIV), $R^{21}$ is $C_1$-$C_2$ alkyl or $C_3$-$C_5$ cycloalkyl.

In some embodiments of treating or preventing a taxane-resistant tumor or cancer with compounds of Formula (XXIV), $R^{21}$ is $C_1$-$C_2$ alkyl.

In some embodiments of treating or preventing a taxane-resistant tumor or cancer with compounds of Formula (XXIV), $R^{21}$ is —$CH_3$.

In some embodiments of treating or preventing a taxane-resistant tumor or cancer with compounds of Formula (XXIV), $R^{22}$ is H or $C_1$-$C_2$ alkyl.

In some embodiments of treating or preventing a taxane-resistant tumor or cancer with compounds of Formula (XXIV), $R^{22}$ is H or —$CH_3$.

In some embodiments of treating or preventing a taxane-resistant tumor or cancer with compounds of Formula (XXIV), $R^{22}$ is —$CH_3$.

In some embodiments of treating or preventing a taxane-resistant tumor or cancer with compounds of Formula (XXIV), $R^{24}$ is H, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)-O—($C_3$-$C_6$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl).

In some embodiments of treating or preventing a taxane-resistant tumor or cancer with compounds of Formula (XXIV), $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_6$ cycloalkyl), —($C_1$-$C_4$ alkyl)$_t$-$O_u$—(4- to 6-membered heterocycle) or —($C_1$-$C_4$ alkyl)-O—($C_1$-$C_4$ alkyl).

In some embodiments of treating or preventing a taxane-resistant tumor or cancer with compounds of Formula (XXIV), $R^{24}$ is $C_1$-$C_4$ alkyl or —($C_1$-$C_4$ alkyl)-O—($C_1$-$C_4$ alkyl).

In some embodiments of treating or preventing a taxane-resistant tumor or cancer with compounds of Formula (XXIV), $R^{24}$ is —($C_1$-$C_2$ alkyl)-O—($C_1$-$C_2$ alkyl).

In some embodiments of treating or preventing a taxane-resistant tumor or cancer with compounds of Formula (XXIV), $R^{24}$ is —$CH_2$—O—$CH_3$.

In some embodiments of treating or preventing a taxane-resistant tumor or cancer with compounds of Formula (XXIV), $R^{24}$ is $C_1$-$C_2$ alkyl.

In some embodiments of treating or preventing a taxane-resistant tumor or cancer with compounds of Formula (XXIV), $R^{24}$ is —$CH_3$.

In some embodiments of treating or preventing a taxane-resistant tumor or cancer with compounds of Formula (XXIV), $R^{24}$ is $C_3$-$C_6$ cycloalkyl.

In some embodiments of treating or preventing a taxane-resistant tumor or cancer with compounds of Formula (XXIV), $R^{24}$ is $C_3$-$C_5$ cycloalkyl.

In some embodiments of treating or preventing a taxane-resistant tumor or cancer with compounds of Formula (XXIV), $R^{24}$ is —CN or —($C_1$-$C_2$ alkyl)-CN.

In some embodiments of treating or preventing a taxane-resistant tumor or cancer with compounds of Formula (XXIV), $R^{24}$ is —CN.

In some embodiments of treating or preventing a taxane-resistant tumor or cancer with compounds of Formula (XXIV), $R^{24}$ is —($C_1$-$C_2$ alkyl)-CN.

In some embodiments of treating or preventing a taxane-resistant tumor or cancer with compounds of Formula (XXIV), $R^{24}$ is H, —$CH_3$, —$CH_2OH$, —$CH_2OCH_3$, —($CH_2$)$_2$OH, —($CH_2$)$_2$OCH$_3$ or —($CH_2$)$_2$N($CH_3$)$_2$.

In some embodiments of treating or preventing a taxane-resistant tumor or cancer with compounds of Formula (XXIV), $R^{24}$ is methyl, isopropyl, cyclopropyl, —CN, or —($C_1$-$C_2$ alkyl)-CN.

In some embodiments of treating or preventing a taxane-resistant tumor or cancer with compounds of Formula (XXIV), $R^{24}$ is substituted with one or more substituents selected from $C_1$-$C_2$ alkyl, oxo, —CN, halogen, alkanoyl, alkoxycarbonyl, —OH and $C_1$-$C_2$ alkoxy.

In some embodiments of treating or preventing a taxane-resistant tumor or cancer with compounds of Formula (XXIV), $R^{24}$ is substituted with one or more substituents selected from methyl, —F, methoxy, —C(=O)CH$_3$ and —C(=O)—OCH$_3$.

In some embodiments of treating or preventing a taxane-resistant tumor or cancer with compounds of Formula (XXIV), $R^{24}$ is substituted with two substituents that are the same or different.

In some embodiments of treating or preventing a taxane-resistant tumor or cancer with compounds of Formula (XXIV), $R^{24}$ is substituted with three substituents that are the same or different.

In some embodiments of treating or preventing a taxane-resistant tumor or cancer with compounds of Formula (XXIV), $R^{25}$ is halogen, —CN, $C_1$-$C_2$ alkyl or cyclopropyl.

In some embodiments of treating or preventing a taxane-resistant tumor or cancer with compounds of Formula (XXIV), $R^{25}$ is halogen, $C_1$-$C_2$ alkyl or cyclopropyl.

In some embodiments of treating or preventing a taxane-resistant tumor or cancer with compounds of Formula (XXIV), $R^{25}$ is —CN, —Cl or —CH$_3$.

In some embodiments of treating or preventing a taxane-resistant tumor or cancer with compounds of Formula (XXIV), $R^{25}$ is —Cl.

In some embodiments of treating or preventing a taxane-resistant tumor or cancer with compounds of Formula (XXIV), $R^{25}$ is —CH$_3$.

In some embodiments of treating or preventing a taxane-resistant tumor or cancer with compounds of Formula (XXIV), $R^{25}$ is substituted with one or more substituents selected from —OH, halogen, $C_1$-$C_2$ alkyl and alkylcarbonyloxy.

In some embodiments of treating or preventing a taxane-resistant tumor or cancer with compounds of Formula (XXIV), $R^{25}$ is substituted with one or more substituents selected from —F, methyl and —O—C(=O)—CH$_3$.

In some embodiments of treating or preventing a taxane-resistant tumor or cancer with compounds of Formula (XXIV), $R^{25}$ is substituted with two substituents that are the same or different.

In some embodiments of treating or preventing a taxane-resistant tumor or cancer with compounds of Formula (XXIV), $R^{25}$ is substituted with three substituents that are the same or different.

In some embodiments of treating or preventing a taxane-resistant tumor or cancer with compounds of Formula (XXIV), $R^{24}$ is C$_1$-C$_4$ alkyl, —(C$_1$-C$_4$ alkyl)-CN or —(C$_3$-C$_6$ cycloalkyl).

In some embodiments of treating or preventing a taxane-resistant tumor or cancer with compounds of Formula (XXIV), $R^{24}$ is —CN, —(C$_1$-C$_2$ alkyl)-CN, —(C$_3$-C$_6$ cycloalkyl) or methyl.

In some embodiments of treating or preventing a taxane-resistant tumor or cancer with compounds of Formula (XXIV), $R^{25}$ is halogen, methyl, ethyl or cyclopropyl.

In some embodiments of treating or preventing a taxane-resistant tumor or cancer with compounds of Formula (XXIV), $R^{25}$ is halogen, —CN, methyl, ethyl or cyclopropyl.

In some embodiments of treating or preventing a taxane-resistant tumor or cancer with compounds of Formula (XXIV), $R^{21}$ is C$_1$-C$_2$ alkyl or C$_3$-C$_6$ cycloalkyl and $R^{22}$ is H or —CH$_3$.

In some embodiments of treating or preventing a taxane-resistant tumor or cancer with compounds of Formula (XXIV), $R^{21}$ is C$_1$-C$_2$ alkyl or C$_3$-C$_6$ cycloalkyl, $R^{22}$ is H or —CH$_3$, $R^{24}$ is —CH$_2$—O—CH$_3$ and $R^{25}$ is —CH$_3$.

In some embodiments of treating or preventing a taxane-resistant tumor or cancer with compounds of Formula (XXIV), $R^{21}$ is —CH$_3$ and $R^{22}$ is H.

In some embodiments of treating or preventing a taxane-resistant tumor or cancer with compounds of Formula (XXIV), $R^1$ is —CN and $R^2$ is H In some embodiments of treating or preventing a taxane-resistant tumor or cancer with compounds of Formula (XXIV), $R^{21}$ is C$_1$-C$_2$ alkyl or C$_3$-C$_6$ cycloalkyl and $R^{22}$ is H or C$_1$-C$_2$ alkyl.

In some embodiments of treating or preventing a taxane-resistant tumor or cancer with compounds of Formula (XXIV), $R^{21}$ is C$_1$-C$_2$ alkyl or C$_3$-C$_6$ cycloalkyl, $R^{22}$ is H or C$_1$-C$_2$ alkyl, $R^{24}$ is —CH$_2$—O—CH$_3$ and $R^{25}$ is —CH$_3$.

In some embodiments of treating or preventing a taxane-resistant tumor or cancer with compounds of Formula (XXIV), $R^{21}$ is C$_1$-C$_2$ alkyl and $R^{22}$ is H.

In some embodiments of treating or preventing a taxane-resistant tumor or cancer with compounds of Formula (XXV), L-Ar is

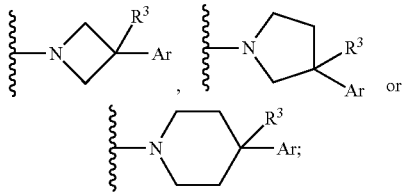

Ar is

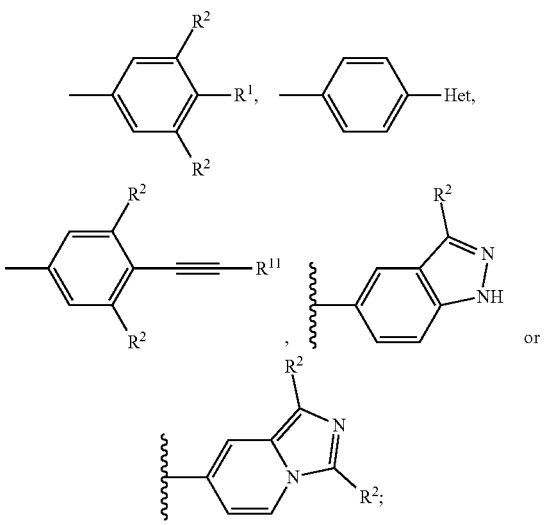

Het is an optionally substituted 5- to 6-membered heteroaryl;

$R^1$ is H, —CN, halogen, optionally substituted C$_1$-C$_4$ alkyl, —O-(optionally substituted C$_3$-C$_5$ cycloalkyl), —O-(optionally substituted 4- to 6-membered heterocycle) or —O-(optionally substituted C$_1$-C$_4$ alkyl), wherein when $R^1$ is not H, —CN or halogen, $R^1$ is optionally substituted with one or more halogens:

each $R^2$ is independently hydrogen, halogen or optionally substituted C$_1$-C$_4$ alkyl;

$R^3$ is H or F;

$R^{11}$ is H or —CH;

$R^{21}$ is H, halogen, optionally substituted C$_1$-C$_4$ alkyl, optionally substituted C$_3$-C$_5$ cycloalkyl or optionally substituted 4- to 6-membered heterocycle;

$R^{22}$ is H, halogen or optionally substituted C$_1$-C$_2$ alkyl; and each $R^{24}$ and $R^{25}$ is independently H, halogen, —CN, -(optionally substituted C$_1$-C$_4$ alkyl)-CN, optionally substituted C$_1$-C$_4$ alkyl, -(optionally substituted C$_1$-C$_4$ alkyl)-OH, -(optionally substituted C$_1$-C$_4$ alkyl)-N(R$^{241}$)$_2$, -(optionally substituted C$_1$-C$_4$ alkyl)$_t$-O$_u$-(optionally substituted C$_3$-C$_5$ cycloalkyl), -(optionally substituted C$_1$-C$_4$ alkyl)$_t$-O$_u$-(optionally substituted 4- to 6-membered heterocycle) or -(optionally substituted C$_1$-C$_4$ alkyl)$_t$-O-(optionally substituted C$_1$-C$_4$ alkyl), wherein:

t is 0 or 1;

u is 0 or 1; and $R^{241}$ is H or optionally substituted C$_1$-C$_2$ alkyl, wherein the compound is not:

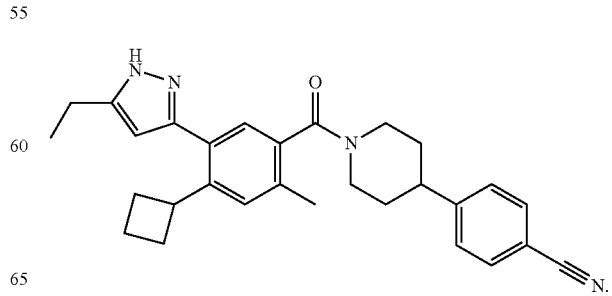

In some embodiments of treating or preventing a taxane-resistant tumor or cancer with compounds of Formula (XXV), L-Ar is

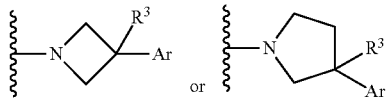

and Ar is

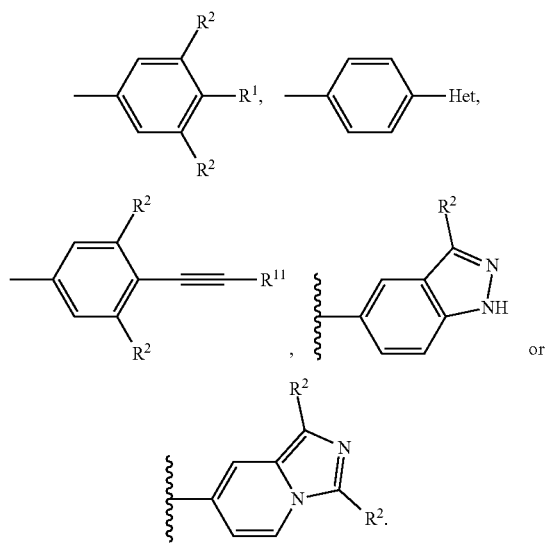

In some embodiments of treating or preventing a taxane-resistant tumor or cancer with compounds of Formula (XXV), L-Ar is

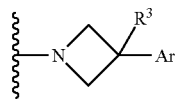

and Ar is

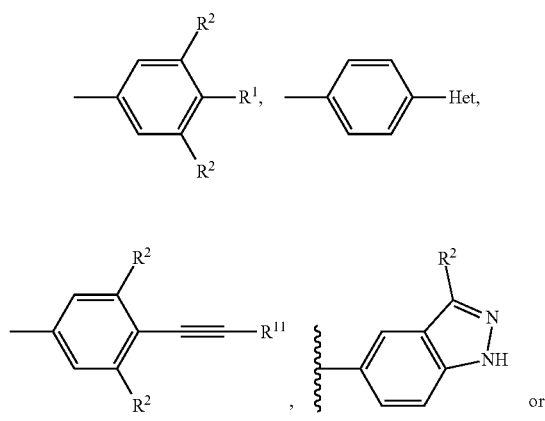

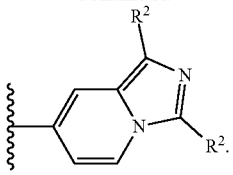

In some embodiments of treating or preventing a taxane-resistant tumor or cancer with compounds of Formula (XXV), Ar is

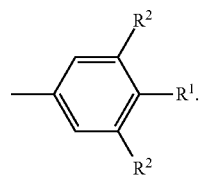

In some embodiments of treating or preventing a taxane-resistant tumor or cancer with compounds of Formula (XXV), $R^1$ is halogen, —CN or $C_1$-$C_2$ haloalkyl.

In some embodiments of treating or preventing a taxane-resistant tumor or cancer with compounds of Formula (XXV), $R^1$ is —CN.

In some embodiments of treating or preventing a taxane-resistant tumor or cancer with compounds of Formula (XXV), $R^2$ is H.

In some embodiments of treating or preventing a taxane-resistant tumor or cancer with compounds of Formula (XXV), $R^{21}$ is halogen, $C_1$-$C_4$ alkyl, $C_3$-$C_5$ cycloalkyl or 4- to 6-membered heterocycle.

In some embodiments of treating or preventing a taxane-resistant tumor or cancer with compounds of Formula (XXV), $R^{21}$ is $C_1$-$C_4$ alkyl, $C_3$-$C_5$ cycloalkyl or 4- to 6-membered heterocycle.

In some embodiments of treating or preventing a taxane-resistant tumor or cancer with compounds of Formula (XXV), $R^{21}$ is $C_1$-$C_2$ alkyl or $C_3$-$C_5$ cycloalkyl.

In some embodiments of treating or preventing a taxane-resistant tumor or cancer with compounds of Formula (XXV), $R^{21}$ is $C_1$-$C_2$ alkyl.

In some embodiments of treating or preventing a taxane-resistant tumor or cancer with compounds of Formula (XXV), $R^{21}$ is —$CH_3$.

In some embodiments of treating or preventing a taxane-resistant tumor or cancer with compounds of Formula (XXV), $R^{22}$ is H or $C_1$-$C_2$ alkyl.

In some embodiments of treating or preventing a taxane-resistant tumor or cancer with compounds of Formula (XXV), $R^{22}$ is H or —$CH_3$.

In some embodiments of treating or preventing a taxane-resistant tumor or cancer with compounds of Formula (XXV), $R^{22}$ is —$CH_3$.

In some embodiments of treating or preventing a taxane-resistant tumor or cancer with compounds of Formula (XXV), each $R^{24}$ and $R^{25}$ is independently H, —CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl).

In some embodiments of treating or preventing a taxane-resistant tumor or cancer with compounds of Formula (XXV), each $R^{24}$ and $R^{25}$ is independently H, $C_1$-$C_4$ alkyl, —($C_1$-$C_4$ alkyl)$_t$-$O_u$-(4- to 6-membered heterocycle) or —($C_1$-$C_4$ alkyl)-O—($C_1$-$C_4$ alkyl).

In some embodiments of treating or preventing a taxane-resistant tumor or cancer with compounds of Formula (XXV), $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl).

In some embodiments of treating or preventing a taxane-resistant tumor or cancer with compounds of Formula (XXV), $R^{24}$ is —CN, —Cl, $C_1$-$C_4$ alkyl or —($C_1$-$C_4$ alkyl)-O—($C_1$-$C_4$ alkyl).

In some embodiments of treating or preventing a taxane-resistant tumor or cancer with compounds of Formula (XXV), $R^{24}$ is $C_1$-$C_4$ alkyl or —($C_1$-$C_4$ alkyl)-O—($C_1$-$C_4$ alkyl).

In some embodiments of treating or preventing a taxane-resistant tumor or cancer with compounds of Formula (XXV), $R^{24}$ is —($C_1$-$C_2$ alkyl)-O—($C_1$-$C_2$ alkyl).

In some embodiments of treating or preventing a taxane-resistant tumor or cancer with compounds of Formula (XXV), $R^{24}$ is $C_1$-$C_4$ alkyl.

In some embodiments of treating or preventing a taxane-resistant tumor or cancer with compounds of Formula (XXV), $R^{24}$ is —$CH_3$.

In some embodiments of treating or preventing a taxane-resistant tumor or cancer with compounds of Formula (XXV), $R^{24}$ is hydrogen.

In some embodiments of treating or preventing a taxane-resistant tumor or cancer with compounds of Formula (XXV), $R^{24}$ is substituted with one or more substituents selected from halogen, $C_3$-$C_5$ cycloalkyl and $C_1$-$C_2$ alkoxy.

In some embodiments of treating or preventing a taxane-resistant tumor or cancer with compounds of Formula (XXV), $R^{24}$ is substituted with one or more substituents selected from —F, cyclopropyl and —$OCH_3$.

In some embodiments of treating or preventing a taxane-resistant tumor or cancer with compounds of Formula (XXV), $R^{24}$ is substituted with two substituents that are the same or different.

In some embodiments of treating or preventing a taxane-resistant tumor or cancer with compounds of Formula (XXV), $R^{24}$ is substituted with three substituents that are the same or different.

In some embodiments of treating or preventing a taxane-resistant tumor or cancer with compounds of Formula (XXV), $R^{25}$ is halogen, methyl, ethyl or cyclopropyl.

In some embodiments of treating or preventing a taxane-resistant tumor or cancer with compounds of Formula (XXV), $R^{25}$ is —CN, —Cl, $C_1$-$C_4$ alkyl, —($C_1$-$C_4$ alkyl)$_t$-O—($C_3$-$C_5$ cycloalkyl) or —($C_1$-$C_4$ alkyl)$_t$-O—($C_1$-$C_4$ alkyl).

In some embodiments of treating or preventing a taxane-resistant tumor or cancer with compounds of Formula (XXV), $R^{25}$ is —CN, —Cl, —$CH_3$, —O—($C_3$-$C_5$ cycloalkyl) or —O—($C_1$-$C_2$ alkyl).

In some embodiments of treating or preventing a taxane-resistant tumor or cancer with compounds of Formula (XXV), $R^{25}$ is —CN, —Cl or $C_1$-$C_4$ alkyl.

In some embodiments of treating or preventing a taxane-resistant tumor or cancer with compounds of Formula (XXV), $R^{25}$ is —CH.

In some embodiments of treating or preventing a taxane-resistant tumor or cancer with compounds of Formula (XXV), $R^{25}$ is —Cl.

In some embodiments of treating or preventing a taxane-resistant tumor or cancer with compounds of Formula (XXV), $R^{25}$ is substituted with one or more halogen.

In some embodiments of treating or preventing a taxane-resistant tumor or cancer with compounds of Formula (XXV), $R^{25}$ is substituted with one or more —F.

In some embodiments of treating or preventing a taxane-resistant tumor or cancer with compounds of Formula (XXV), $R^{25}$ is substituted by two substituents.

In some embodiments of treating or preventing a taxane-resistant tumor or cancer with compounds of Formula (XXV), $R^{25}$ is substituted by three substituents.

In some embodiments of treating or preventing a taxane-resistant tumor or cancer with compounds of Formula (XXV), $R^{21}$ is —$CH_3$ and $R^{22}$ is H or methyl.

In some embodiments of treating or preventing a taxane-resistant tumor or cancer with compounds of Formula (XXV), $R^{21}$ is $C_1$-$C_2$ alkyl or $C_3$-$C_5$ cycloalkyl and $R^{22}$ is H or —$CH_3$.

In some embodiments of treating or preventing a taxane-resistant tumor or cancer with compounds of Formula (XXV), $R^{21}$ is —$CH_3$ and $R^{22}$ is H.

In some embodiments of treating or preventing a taxane-resistant tumor or cancer with compounds of Formula (XXV), $R^{24}$ is H or —$CH_3$ and $R^{25}$ is —Cl.

In some embodiments of treating or preventing a taxane-resistant tumor or cancer with compounds of Formula (XXV), $R^1$ is —CN and $R^2$ is H.

In some embodiments of treating or preventing a taxane-resistant tumor or cancer with compounds of Formula (XXV), $R^{21}$ is $C_1$-$C_2$ alkyl or $C_3$-$C_5$ cycloalkyl and $R^{22}$ is $C_1$-$C_2$ alkyl.

In some embodiments of treating or preventing a taxane-resistant tumor or cancer with compounds of Formula (XXV), $R^{21}$ is $C_1$-$C_2$ alkyl or $C_3$-$C_5$ cycloalkyl and $R^{22}$ is H or $C_1$-$C_2$ alkyl.

In some embodiments of treating or preventing a taxane-resistant tumor or cancer with compounds of Formula (XXV), $R^{21}$ is $C_1$-$C_2$ alkyl and $R^{22}$ is H or —$CH_3$.

In some embodiments of treating or preventing a taxane-resistant tumor or cancer with compounds of Formula (XXV), $R^{21}$ is $C_1$-$C_2$ alkyl and $R^{22}$ is H.

In some embodiments of treating or preventing a taxane-resistant tumor or cancer with compounds of Formula (XXVI), L-Ar is

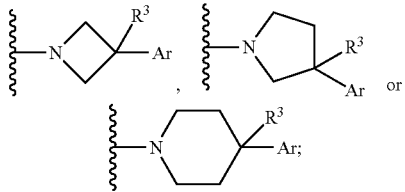

Ar is

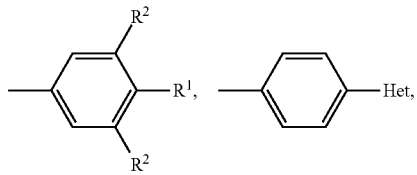

-continued

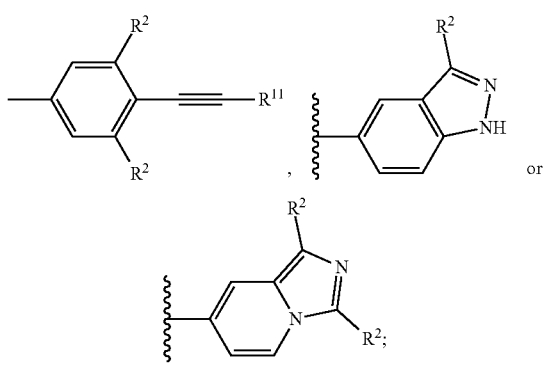

Het is an optionally substituted 5- to 6-membered heteroaryl;

$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens:

each $R^2$ is independently hydrogen, halogen or optionally substituted $C_1$-$C_4$ alkyl;

$R^3$ is H or F;

$R^{11}$ is H or —CH$_3$;

$R^{21}$ is H, halogen, optionally substituted $C_1$-$C_4$ alkyl, optionally substituted $C_3$-$C_5$ cycloalkyl or optionally substituted 4- to 6-membered heterocycle;

$R^{22}$ is H, halogen or optionally substituted $C_1$-$C_2$ alkyl; and each of $R^{24}$ and $R^{25}$ is independently H, optionally substituted $C_1$-$C_4$ alkyl, or halogen.

In some embodiments of treating or preventing a taxane-resistant tumor or cancer with compounds of Formula (XXVI), L-Ar is

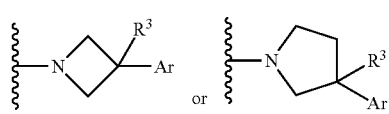

and Ar is

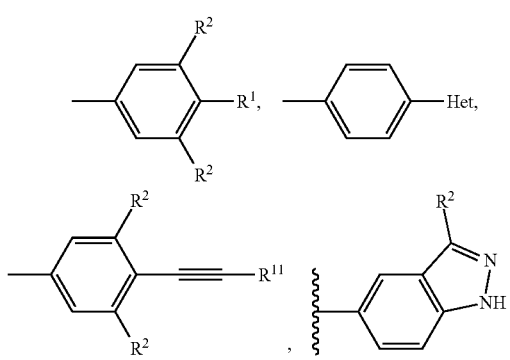

-continued

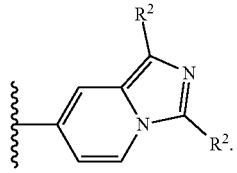

In some embodiments of treating or preventing a taxane-resistant tumor or cancer with compounds of Formula (XXVI), L-Ar is

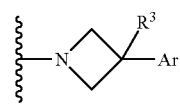

and Ar is

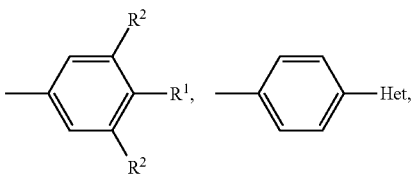

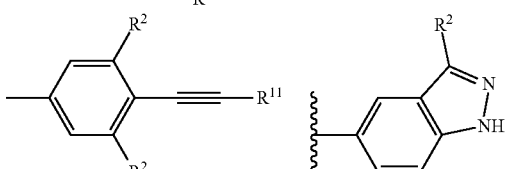

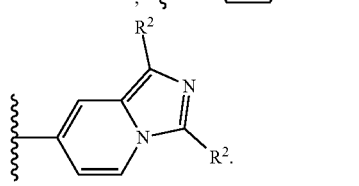

In some embodiments of treating or preventing a taxane-resistant tumor or cancer with compounds of Formula (XXVI), $R^1$ is halogen, —CN or $C_1$-$C_2$ haloalkyl.

In some embodiments of treating or preventing a taxane-resistant tumor or cancer with compounds of Formula (XXVI), $R^{21}$ is halogen, $C_1$-$C_4$ alkyl, $C_3$-$C_5$ cycloalkyl or 4- to 6-membered heterocycle.

In some embodiments of treating or preventing a taxane-resistant tumor or cancer with compounds of Formula (XXVI), $R^{21}$ is —CH$_3$.

In some embodiments of treating or preventing a taxane-resistant tumor or cancer with compounds of Formula (XXVI), $R^{22}$ is H.

In some embodiments of treating or preventing a taxane-resistant tumor or cancer with compounds of Formula (XXVI), $R^{21}$ is methyl, $R^{22}$ is H and L-Ar is

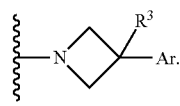

In some embodiments of treating or preventing a taxane-resistant tumor or cancer with compounds of Formula (XXVII),
L-Ar is

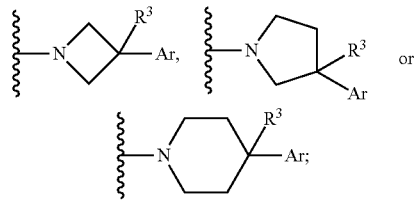

Ar is

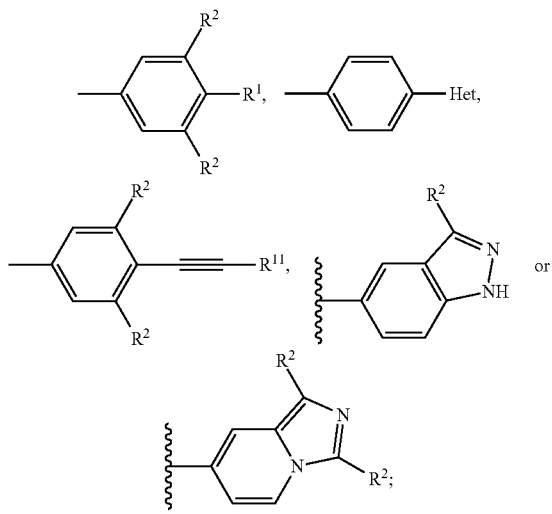

Het is an optionally substituted 5- to 6-membered heteroaryl;
$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, then $R^1$ is optionally substituted with one or more halogens;
each $R^2$ is independently hydrogen, halogen or optionally substituted $C_1$-$C_4$ alkyl;
$R^3$ is H or F;
$R^{11}$ is H or —CH$_3$;
$R^{21}$ is H, halogen, optionally substituted $C_1$-$C_4$ alkyl, optionally substituted $C_3$-$C_5$ cycloalkyl or optionally substituted 4- to 6-membered heterocycle;
$R^{22}$ is H, halogen or optionally substituted $C_1$-$C_2$ alkyl;
$R^{24}$ is H, optionally substituted $C_1$-$C_4$ alkyl, -(optionally substituted $C_1$-$C_4$ alkyl)-OH, -(optionally substituted $C_1$-$C_4$ alkyl)-N($R^{241}$)$_2$, -(optionally substituted $C_1$-$C_4$ alkyl)$_t$-O$_u$-(optionally substituted $C_3$-$C_5$ cycloalkyl), -(optionally substituted $C_1$-$C_4$ alkyl)$_t$-O$_u$-(optionally substituted 4- to 6-membered heterocycle) or -(optionally substituted $C_1$-$C_4$ alkyl)-O-(optionally substituted $C_1$-$C_4$ alkyl), wherein:
t is 0 or 1;
u is 0 or 1;
with the proviso that when u is 1, t is 1; and
$R^{241}$ is H or optionally substituted $C_1$-$C_2$ alkyl.

In some embodiments of treating or preventing a taxane-resistant tumor or cancer with compounds of Formula (XXVII), L-Ar is

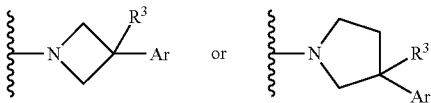

and Ar is

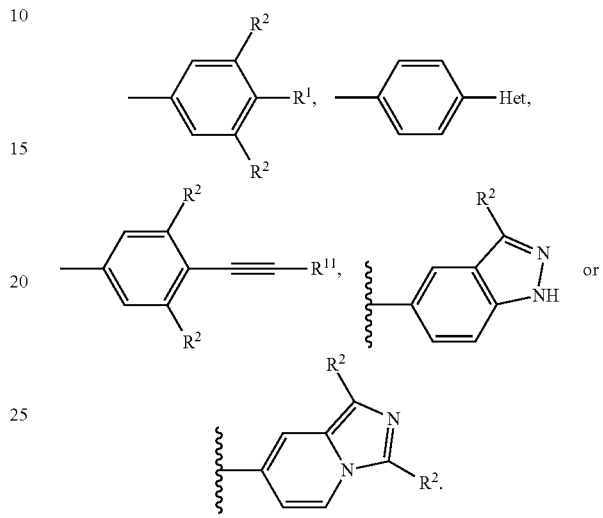

In some embodiments of treating or preventing a taxane-resistant tumor or cancer with compounds of Formula (XXVII), $R^1$ is halogen, —CN or $C_1$-$C_2$ haloalkyl.

In some embodiments of treating or preventing a taxane-resistant tumor or cancer with compounds of Formula (XXVII), $R^1$ is —CN.

In some embodiments of treating or preventing a taxane-resistant tumor or cancer with compounds of Formula (XXVII), $R^2$ is H.

In some embodiments of treating or preventing a taxane-resistant tumor or cancer with compounds of Formula (XXVII), $R^{21}$ is halogen, $C_1$-$C_4$ alkyl, $C_3$-$C_5$ cycloalkyl or 4- to 6-membered heterocycle.

In some embodiments of treating or preventing a taxane-resistant tumor or cancer with compounds of Formula (XXVII), $R^{21}$ is $C_1$-$C_2$ alkyl or $C_3$-$C_5$ cycloalkyl.

In some embodiments of treating or preventing a taxane-resistant tumor or cancer with compounds of Formula (XXVII), $R^{21}$ is $C_1$-$C_2$ alkyl.

In some embodiments of treating or preventing a taxane-resistant tumor or cancer with compounds of Formula (XXVII), $R^{21}$ is $C_3$-$C_5$ cycloalkyl.

In some embodiments of treating or preventing a taxane-resistant tumor or cancer with compounds of Formula (XXVII), $R^{22}$ is H or $C_1$-$C_2$ alkyl.

In some embodiments of treating or preventing a taxane-resistant tumor or cancer with compounds of Formula (XXVII), $R^{22}$ is H.

In some embodiments of treating or preventing a taxane-resistant tumor or cancer with compounds of Formula (XXVII), $R^{22}$ is $C_1$-$C_2$ alkyl.

In some embodiments of treating or preventing a taxane-resistant tumor or cancer with compounds of Formula (XXVII), $R^{22}$ is —CH$_3$.

In some embodiments of treating or preventing a taxane-resistant tumor or cancer with compounds of Formula (XXVII), $R^{24}$ is $C_1$-$C_4$ alkyl or —($C_1$-$C_4$ alkyl)-O—($C_1$-$C_4$ alkyl).

In some embodiments of treating or preventing a taxane-resistant tumor or cancer with compounds of Formula (XXVII), $R^{24}$ is —($C_1$-$C_2$ alkyl)-O—($C_1$-$C_2$ alkyl).

In some embodiments of treating or preventing a taxane-resistant tumor or cancer with compounds of Formula (XXVII), $R^{21}$ is $C_1$-$C_2$ alkyl or $C_3$-$C_5$ cycloalkyl and $R^{22}$ is $C_1$-$C_2$ alkyl.

In some embodiments of treating or preventing a taxane-resistant tumor or cancer with compounds of Formula (XXVII), $R^{21}$ is $C_3$-$C_5$ cycloalkyl and $R^{22}$ is H or $C_1$-$C_2$ alkyl.

In some embodiments of treating or preventing a taxane-resistant tumor or cancer with compounds of Formula (XXVII), $R^{21}$ is $C_3$-$C_5$ cycloalkyl and $R^{22}$ is H or —$CH_3$.

In some embodiments of treating or preventing a taxane-resistant tumor or cancer with compounds of Formula (XXVII), $R^{21}$ is $C_3$-$C_5$ cycloalkyl and $R^{22}$ is H or —$CH_3$.

In some embodiments of treating or preventing a taxane-resistant tumor or cancer with compounds of Formula (XXVII), $R^1$ is —CN and $R^2$ is H.

In some embodiments of treating or preventing a taxane-resistant tumor or cancer with compounds of Formula (XXVIII), L-Ar is

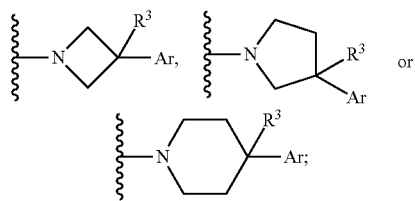

Ar is

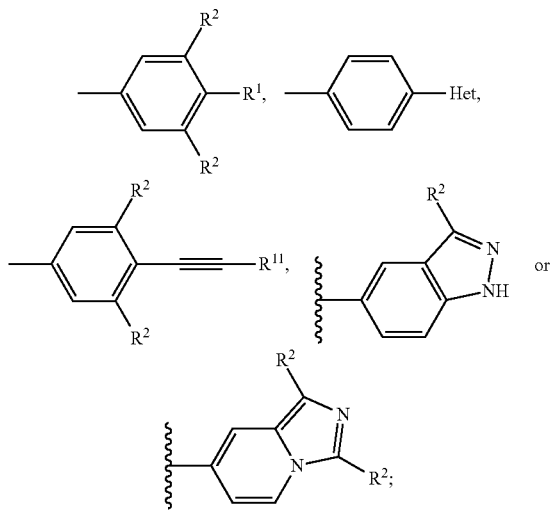

with the proviso that when L-Ar is

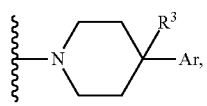

Ar is not

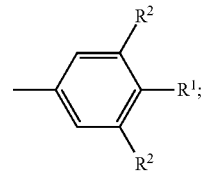

$L^2$ is —$NHR^{35}$ or —$C(O)NHR^{351}$, wherein $R^{351}$ is optionally substituted $C_1$-$C_6$ alkyl, optionally substituted $C_3$-$C_5$ cycloalkyl, optionally substituted 4- to 6-membered heterocycle, optionally substituted aryl or optionally substituted heteroaryl;

Het is an optionally substituted 5- to 6-membered heteroaryl;

$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens:

each $R^2$ is independently hydrogen, halogen or optionally substituted $C_1$-$C_4$ alkyl;

$R^3$ is H or F;

$R^{11}$ is H or —$CH_3$;

$R^{21}$ is H, halogen, optionally substituted $C_1$-$C_4$ alkyl, optionally substituted $C_3$-$C_5$ cycloalkyl or optionally substituted 4- to 6-membered heterocycle:

$R^{22}$ is H, halogen, or optionally substituted $C_1$-$C_2$ alkyl; and $R^{35}$ is —$C(O)R^{351}$, —$C(O)NHR^{351}$, —$C(O)OR^{351}$ or —$S(O)_2R^{351}$, wherein $R^{351}$ is optionally substituted $C_1$-$C_6$ alkyl, optionally substituted $C_3$-$C_5$ cycloalkyl, optionally substituted 4- to 6-membered heterocycle, optionally substituted aryl or optionally substituted heteroaryl.

In some embodiments of treating or preventing a taxane-resistant tumor or cancer with compounds of Formula (XXVIII), $L^2$ is —$NHR^{35}$.

In some embodiments of treating or preventing a taxane-resistant tumor or cancer with compounds of Formula (XXVIII), $L^2$ is —$C(O)NHR^{351}$.

In some embodiments of treating or preventing a taxane-resistant tumor or cancer with compounds of Formula (XXIX), each W, X, Y and Z is independently —N— or —$CR^{26}$— with the proviso that not more than 2 of W, X, Y and Z are —N—;

$R^{26}$ is H, optionally substituted $C_1$-$C_4$ alkyl, —O-(optionally substituted $C_1$-$C_4$ alkyl), —$N(R^{27})_2$, —$S(O)_2$-(optionally substituted $C_1$-$C_4$ alkyl) or —C(O)-(optionally substituted $C_1$-$C_4$ alkyl);

each $R^{27}$ is independently H or optionally substituted $C_1$-$C_4$ alkyl or both $R^{27}$ are optionally substituted $C_1$-$C_4$ alkyl and join to form an optionally substituted 3- to 6-membered ring together with the N to which they are attached and wherein the ring optionally includes one oxygen atom as one of the members of the ring;

Ar is

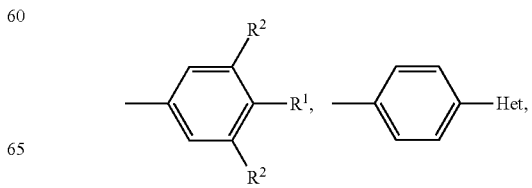

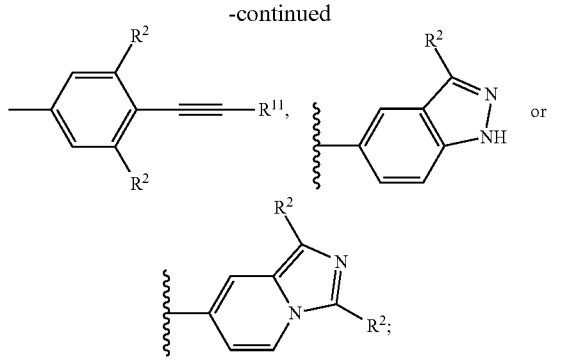

Het is an optionally substituted 5- to 6-membered heteroaryl;

$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens:

each $R^2$ is independently hydrogen, halogen or optionally substituted $C_1$-$C_4$ alkyl;

$R^3$ is H or F;

$R^{11}$ is H or —$CH_3$;

$R^{21}$ is H, halogen, optionally substituted $C_1$-$C_4$ alkyl, optionally substituted $C_3$-$C_5$ cycloalkyl or an optionally substituted 4- to 6-membered heterocycle; and $R^{22}$ is H, halogen or optionally substituted $C_1$-$C_2$ alkyl.

In some embodiments of treating or preventing a taxane-resistant tumor or cancer with compounds of Formula (XXIX), Ar is

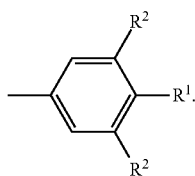

In some embodiments of treating or preventing a taxane-resistant tumor or cancer with compounds of Formula (XXIX), Y is —$CR^{26}$— wherein $R^{26}$ is —$N(R^{27})_2$.

In some embodiments of treating or preventing a taxane-resistant tumor or cancer with compounds of Formula (XXIX), X is —N—.

In some embodiments of treating or preventing a taxane-resistant tumor or cancer in a subject in need thereof, the taxane-resistant tumor is selected from paclitaxel-resistant tumor, Nab-paclitaxel-resistant tumor, docetaxel-resistant tumor, and cabazitaxel-resistant tumor.

In other embodiments of the method for treating or preventing a taxane-resistant tumor or cancer in a subject, the fatty acid synthase inhibitor is a compound having the structure of Formula (I), (II), (III), (IV), (VII), (IX), (XIX), (XXI), (XXIII), (XXIV), (XXV), (XXVI), (XXVII), or (XXIX). In other embodiments of the method for treating a taxane-resistant tumor or cancer in a subject, the fatty acid synthase inhibitor is a compound having the structure of any one of the compounds of Formula (I), (II), (III), (XIX), or (XXI). In particular embodiments of the method for treating a taxane-resistant tumor or cancer in a subject, the fatty acid synthase inhibitor is a compound having the structure of any one of the compounds of Formula (I), (II), or (III).

In other embodiments of treating or preventing a taxane-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating or preventing a taxane-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating or preventing a taxane-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a taxane-resistant tumor in a subject, the fatty acid synthase inhibitor is a compound having the structure of any one of the compounds of Formula (I), (II), (III), (XIX), or (XXI). In particular embodiments of the method for treating or preventing a taxane-resistant tumor in a subject, the fatty acid synthase inhibitor is a compound having the structure of any one of the compounds of Formula (I), (II), or (III).

In other embodiments of treating or preventing a taxane-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating or preventing a taxane-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating or preventing a taxane-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a taxane-resistant cancer in a subject, the fatty acid synthase inhibitor is a compound having the structure of any one of the compounds of Formula (I), (II), (III), (XIX), or (XXI). In particular embodiments of the method for treating or preventing a taxane-resistant cancer in a subject, the fatty acid synthase inhibitor is a compound having the structure of any one of the compounds of Formula (I), (II), or (III).

In other embodiments of the method for treating or preventing a taxane-resistant cancer a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a taxane-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a taxane-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a taxane-resistant tumor or cancer in a subject, the fatty acid synthase inhibitor is a compound having the structure of any one of the compounds of Formula (I), (II), (III), (XIX), or (XXI). In particular embodiments of the method for treating a taxane-resistant tumor or cancer in a subject, the fatty acid synthase inhibitor is a compound having the structure of any one of the compounds of Formula (I), (II), or (II).

In other embodiments of the method for treating a taxane-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a taxane-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a taxane-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a taxane-resistant tumor in a subject, the fatty acid synthase inhibitor is a compound having the structure of any one of the compounds of Formula (I), (II), (III), (XIX), or (XXI). In particular embodiments of the method for treating a taxane-resistant tumor in a subject, the fatty acid synthase inhibitor is a compound having the structure of any one of the compounds of Formula (I), (II), or (III). In other embodiments of the method for treating a taxane-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a taxane-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a taxane-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a taxane-resistant cancer in a subject, the fatty acid synthase inhibitor is a compound having the structure of any one of the compounds of Formula (I), (II), (III), (XIX), or (XXI). In particular embodiments of the method for treating a taxane-resistant cancer in a subject, the fatty acid synthase inhibitor is a compound having the structure of any one of the compounds of Formula (I), (II), or (III).

In other embodiments of the method for treating a taxane-resistant cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a taxane-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a taxane-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a taxane-resistant tumor or cancer in a subject, the fatty acid synthase inhibitor is a compound having the structure of any one of the compounds of Formula (I), (II), (III), (XIX), or (XXI). In particular embodiments of the method for preventing a taxane-resistant tumor or cancer in a subject, the fatty acid synthase inhibitor is a compound having the structure of any one of the compounds of Formula (I), (II), or (III).

In other embodiments of the method for preventing a taxane-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a taxane-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a taxane-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a taxane-resistant tumor in a subject, the fatty acid synthase inhibitor is a compound having the structure of any one of the compounds of Formula (I), (II), (III), (XIX), or (XXI). In particular embodiments of the method for preventing a taxane-resistant tumor in a subject, the fatty acid synthase inhibitor is a compound having the structure of any one of the compounds of Formula (I), (II), or (III).

In other embodiments of the method for preventing a taxane-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a taxane-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a taxane-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVIII), or (XXIX). In other embodiments of the method for preventing a taxane-resistant cancer in a subject, the fatty acid synthase inhibitor is a compound having the structure of any one of the compounds of Formula (I), (II), (III), (XIX), or (XXI). In particular embodiments of the method for preventing a taxane-resistant cancer in a subject, the fatty acid synthase inhibitor is a compound having the structure of any one of the compounds of Formula (I), (II), or (III).

In other embodiments of the method for preventing a taxane-resistant cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

In particular embodiments of the method for treating or preventing taxane-resistant cancer in a subject, the fatty acid synthase inhibitor is one or more compounds, forms, and/or agents that act as an inhibitor of FASN gene expression or FASN protein activity. The choice of FASN inhibitor agents that can be co-administered with Nab-paclitaxel, paclitaxel, docetaxel, or cabazitaxel can depend, at least in part, on the cancer being treated. In certain embodiments, Nab-paclitaxel, paclitaxel, docetaxel, and cabazitaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for treating or preventing taxane-resistant cancer, the cancer is selected from the group consisting of lung cancer, breast cancer, ovarian cancer, prostate cancer, colon cancer, and pancreatic cancer. In further aspects, the tumor can be derived from thyroid, lymph node, kidney, ureter, bladder, ovary, teste, uterus, cervix, prostate, bone, skeletal muscle, bone marrow, blood, skin, stomach, head, neck, esophagus, small bowel, colon, rectum, pancreas, liver, bile duct, gallbladder, smooth muscle, brain, spinal cord, nerves, ear, eye, nasopharynx, oropharynx, salivary gland or heart tissue, or the cancer can be metastatic. In a particular embodiment, the taxane-resistant cancer is lung cancer. In a particular embodiment, the taxane-resistant cancer is breast cancer. In a particular embodiment, the taxane-resistant cancer is ovarian cancer. In a particular embodiment, the taxane-resistant cancer is prostate cancer. In a particular embodiment, the taxane-resistant cancer is colon cancer. In a particular embodiment, the taxane-resistant cancer is pancreatic cancer.

As described above, in some embodiments, the methods and compositions described herein are useful for treating or preventing a tumor or cancer in a subject who is taxane-resistant (or who has a taxane-resistant tumor or cancer), a subject who was previously administered or treated with a taxane (but not in combination with a compound of Formula (I), Formula (II), or Formula (III) as described herein), a subject who does not respond or has not responded favorably or adequately to taxane therapy, and/or a subject who failed therapy with a taxane. Taxane therapy should be understood to include treatment with any taxane, i.e., Nab-paclitaxel, paclitaxel, docetaxel, and cabazitaxel. In certain embodiments, the subject was previously treated with taxane monotherapy or was previously treated with a taxane combination therapy that did not include treatment with a compound of Formula (I), Formula (II), or Formula (III) as described herein. In certain embodiments, the taxane-resistant subject initially responded to taxane therapy, but the subject eventually exhibited decreased or no response to the taxane therapy. In certain embodiments, the taxane-resistant tumor or cancer in the subject initially responded to taxane therapy, but the tumor or cancer eventually exhibited decreased or no response to the taxane therapy. The term "taxane-resistant subject" is used generally herein to indicate a subject who is taxane-resistant or who has a taxane-resistant tumor or cancer. As used herein, the term "taxane-resistant" means that the tumor or cancer does not or may not respond or has not responded favorably or adequately to taxane therapy. In certain embodiments, a taxane-resistant subject may be a taxane treatment naïve subject, or the taxane-resistant subject may have previously been treated with taxane therapy, and did not respond favorably or adequately, either initially or after some time period. In certain embodiments, a diagnostic may be used before taxane therapy to determine if the subject is taxane-resistant, or has a taxane-resistant tumor or cancer, or if the present invention would enhance the activity of Nab-paclitaxel, paclitaxel, docetaxel, or cabazitaxel alone.

In particular embodiments of the method of treating or preventing a taxane-resistant tumor or cancer in a subject in need thereof, the fatty acid synthase inhibitor is administered simultaneously with Nab-paclitaxel, paclitaxel, docetaxel, or cabazitaxel. In particular embodiments, the fatty acid synthase inhibitor and Nab-paclitaxel, paclitaxel, docetaxel, or cabazitaxel are administered simultaneously as a single pharmaceutical composition. In particular embodiments, the fatty acid synthase inhibitor and Nab-paclitaxel, paclitaxel, docetaxel, or cabazitaxel are administered simultaneously as separate dosage forms. In particular embodiments of the method of treating or preventing a taxane-resistant tumor or cancer in a subject in need thereof, the fatty acid synthase inhibitor is administered before Nab-paclitaxel, paclitaxel, docetaxel, or cabazitaxel is administered. In particular embodiments of the method of treating or preventing a taxane-resistant tumor or cancer in a subject in need thereof, the fatty acid synthase inhibitor is administered after Nab-paclitaxel, paclitaxel, docetaxel, or cabazitaxel is administered.

In particular embodiments, a method for treating a taxane-resistant tumor or cancer in a subject is provided, the method comprising:

(a) determining that the subject is taxane-resistant, or has a taxane-resistant tumor or cancer, and (b) administering to the subject in need thereof a therapeutically effective amount of a fatty acid synthase inhibitor.

In particular embodiments, Steps (a) and (b) can be performed in either order. That is, step (a) can be performed before step (b) or step (b) can be performed before step (a).

In particular embodiments of the method for treating a taxane-resistant tumor or cancer in a subject, the method further comprises administering to the subject in need thereof a therapeutically effective amount of Nab-paclitaxel, paclitaxel, docetaxel, or cabazitaxel.

In some embodiments of the method for treating a taxane-resistant tumor or cancer in a subject, the fatty acid synthase inhibitor is a compound having the structure of any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In particular embodiments of the method for treating a taxane-resistant tumor or cancer in a subject, the fatty acid synthase inhibitor is a compound having the structure of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In other embodiments of the method for treating a taxane-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a taxane-resistant tumor or cancer in a subject, the fatty acid synthase inhibitor is a compound having the structure of any one of the compounds of Formula (I), (II), (III), (XIX), or (XXI). In particular embodiments of the method for treating a taxane-resistant tumor or cancer in a subject, the fatty acid synthase inhibitor is a compound having the structure of any one of the compounds of Formula (I), (II), or (III).

In particular embodiments of the method for treating a taxane-resistant tumor or cancer in a subject, the fatty acid synthase inhibitor is one or more compounds, forms, and/or agents that act as an inhibitor of FASN gene expression or FASN protein activity. The choice of FASN inhibitor agents that can be co-administered with a taxane can depend, at least in part, on the cancer being treated. In certain embodiments, a taxane can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of any of the methods described herein for treating a taxane-resistant tumor or cancer, the taxane-resistant tumor or cancer is selected from the group consisting of lung cancer, breast cancer, ovarian cancer, prostate cancer, colon cancer, and pancreatic cancer. In a particular embodiment, the taxane-resistant tumor or cancer is lung cancer. In a particular embodiment, the taxane-resistant tumor or cancer is breast cancer. In a particular embodiment, the taxane-resistant tumor or cancer is ovarian cancer. In a particular embodiment, the taxane-resistant tumor or cancer is prostate cancer. In a particular embodiment, the taxane-resistant tumor or cancer is colon cancer. In a particular embodiment, the taxane-resistant tumor or cancer is pancreatic cancer.

In particular embodiments, a taxane-resistant tumor or cancer is determined by testing cells of the tumor or cancer for their responsiveness to a taxane, e.g., the effect of a taxane on the growth rate or amount of growth of the tumor or cancer cells. In one embodiment, testing the subject's cancer cells comprises contacting a sample of the subject's cancer cells with a taxane and contacting a different sample of the subject's cancer cells with a negative control, e.g., an unrelated compound or vehicle only. In one embodiment, testing the subject's cancer cells comprises contacting a sample of the subject's cancer cells with a taxane and contacting a different sample of the subject's cancer cells with a combination of a taxane and a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and comparing the response between the two groups of cancer cells. In certain embodiments, the cells are tested as described in the accompanying Example. In particular embodiments, the cells are tested in vitro. In certain embodiments, the response of the cells to either a taxane, negative control, or the combination of a taxane and the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) that is measured and compared is the growth rate of the cells, the growth amount of the cells, or the viability of the cells. In certain embodiments, a tumor sample is taxane-resistant if the growth rate of the tumor cells, the growth amount of the tumor cells, or the viability of the tumor cells is not significantly decreased upon treatment with a taxane as compared to treatment with the negative control. In certain embodiments, a tumor sample is taxane-resistant if the growth rate or the viability of the tumor cells is significantly decreased upon treatment with the combination of a taxane and a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), as compared to treatment with a taxane alone. In particular embodiments, a significant decrease is a decrease greater than or equal to 25%, greater than or equal to 50%, greater than or equal to 60%, greater than or equal to 70%, greater than or equal to 80%, greater than or equal to 90%, greater than or equal to 100%, greater than or equal to 150%, greater than or equal to 200%, or greater than or equal to 500% as compared to the relevant control.

In particular embodiments of the method of treating or preventing a taxane-resistant tumor or cancer in a subject in need thereof, wherein the subject has been determined to be taxane resistant or have a taxane-resistant tumor or cancer, the fatty acid synthase inhibitor is administered simultaneously with a taxane. In particular embodiments, the fatty acid synthase inhibitor and a taxane are administered simultaneously as a single pharmaceutical composition. In particular embodiments, the fatty acid synthase inhibitor and a taxane are administered simultaneously as separate dosage forms. In particular embodiments of the method of treating or preventing a taxane-resistant tumor or cancer in a subject in need thereof, wherein the subject has been determined to be taxane resistant or have a taxane-resistant tumor or cancer, the fatty acid synthase inhibitor is administered before a taxane is administered. In particular embodiments of the method of treating or preventing a taxane-resistant tumor or cancer in a subject in need thereof, wherein the subject has been determined to be taxane resistant or have a taxane-resistant tumor or cancer, the fatty acid synthase inhibitor is administered after a taxane is administered.

In particular embodiments, the methods and compositions described herein are useful for treating or preventing a tumor or cancer in a subject in need thereof, the method comprising administering to the subject in need thereof a therapeutically effective amount of a fatty acid synthase inhibitor. In particular embodiments, the method further comprises administering to the subject in need thereof a therapeutically effective amount of a taxane (i.e., Nab-paclitaxel, paclitaxel, docetaxel, and cabazitaxel). In particular embodiments of treating or preventing a tumor or cancer in a subject in need thereof, the fatty acid synthase inhibitor is a compound of Formula (I), (II), (III), (IV), (VII), (IX), (XIX), (XXI), (XXIII), (XXIV), (XXV), (XXVI), (XXVII), or (XXIX).

In particular embodiments of the method for treating cancer in a subject, the fatty acid synthase inhibitor is one or more compounds, forms, and/or agents that act as an inhibitor of FASN gene expression or FASN protein activity. The choice of FASN inhibitor agents that can be co-administered with a taxane can depend, at least in part, on the cancer being treated. In certain embodiments, a taxane can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for treating cancer, the cancer is selected from the group consisting of lung cancer, breast cancer, ovarian cancer, prostate cancer, colon cancer, and pancreatic cancer. In further aspects, the tumor can be derived from thyroid, lymph node, kidney, ureter, bladder, ovary, teste, uterus, cervix, prostate, bone, skeletal muscle, bone marrow, blood, skin, stomach, head, neck, esophagus, small bowel, colon, rectum, pancreas, liver, bile duct, gallbladder, smooth muscle, brain, spinal cord, nerves, ear, eye, nasopharynx, oropharynx, salivary gland or heart tissue, or the cancer can be metastatic. In a particular embodiment, the taxane-resistant cancer is lung cancer. In a particular embodiment, the taxane-resistant cancer is breast cancer. In a particular embodiment, the taxane-resistant cancer is ovarian cancer. In a particular embodiment, the taxane-resistant cancer is prostate cancer. In a particular embodiment, the taxane-resistant cancer is colon cancer. In a particular embodiment, the taxane-resistant cancer is pancreatic cancer.

In particular embodiments of the method of treating or preventing a tumor or cancer in a subject in need thereof, the fatty acid synthase inhibitor is administered simultaneously with a taxane. In particular embodiments, the fatty acid synthase inhibitor and a taxane are administered simultaneously as a single pharmaceutical composition. In particular embodiments, the fatty acid synthase inhibitor and a taxane are administered simultaneously as separate dosage forms. In particular embodiments of the method of treating or preventing a tumor or cancer in a subject in need thereof, the fatty acid synthase inhibitor is administered before a taxane is administered. In particular embodiments of the method of treating or preventing a tumor or cancer in a subject in need thereof, the fatty acid synthase inhibitor is administered after a taxane is administered.

As described above, in particular embodiments, the methods and compositions described herein are useful for enhancing the activity of a taxane in treating a tumor or a cancer, the method comprising administering to a subject in need thereof, a therapeutically effective amount of a taxane and a fatty acid synthase inhibitor.

In some embodiments of the method for enhancing the activity of a taxane in treating a tumor or a cancer, the fatty acid synthase inhibitor is a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In other embodiments of the method for enhancing the activity of a taxane in treating a tumor or a cancer, the fatty acid synthase inhibitor is a compound of Formula (I), (II), (III), (IV), (VII), (IX), (XIX), (XXI), (XXIII), (XXIV), (XXV), (XXVI), (XXVII), or (XXIX). In particular embodiments of the method for enhancing the activity of a taxane in treating a tumor or a cancer, the fatty acid synthase inhibitor is a compound of Formula (I), (II), or (III).

In particular embodiments of the method for enhancing the activity of a taxane in treating a tumor or a cancer, the fatty acid synthase inhibitor is one or more compounds, forms, and/or agents that act as an inhibitor of FASN gene expression or FASN protein activity. The choice of FASN inhibitor agents that can be co-administered with a taxane can depend, at least in part, on the cancer being treated. In certain embodiments, a taxane can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for enhancing the activity of a taxane in treating a tumor or a cancer, the cancer is selected from the group consisting of lung cancer, breast cancer, ovarian cancer, prostate cancer, colon cancer, and pancreatic cancer. In a particular embodiment, the cancer is lung cancer. In a particular embodiment, the cancer is breast cancer. In a particular embodiment, the cancer is ovarian cancer. In a particular embodiment, the cancer is prostate cancer. In a particular embodiment, the cancer is colon cancer. In a particular embodiment, the cancer is pancreatic cancer.

In particular embodiments of the method for enhancing the activity of a taxane in treating a tumor or a cancer, the tumor or cancer is taxane-resistant. In certain embodiments, the taxane-resistant cancer is selected from the group consisting of lung cancer, breast cancer, ovarian cancer, prostate cancer, colon cancer, and pancreatic cancer. In a particular embodiment, the taxane-resistant cancer is lung cancer. In a particular embodiment, the taxane-resistant cancer is breast cancer. In a particular embodiment, the taxane-resistant cancer is ovarian cancer. In a particular embodiment, the taxane-resistant cancer is prostate cancer. In a particular embodiment, the taxane-resistant cancer is colon cancer. In a particular embodiment, the taxane-resistant cancer is pancreatic cancer.

In particular embodiments of the method for enhancing the activity of a taxane in treating a tumor or a cancer, the fatty acid synthase inhibitor is administered simultaneously with a taxane. In particular embodiments, the fatty acid synthase inhibitor and a taxane are administered simultaneously as a single pharmaceutical composition. In particular embodiments, the fatty acid synthase inhibitor and a taxane are administered simultaneously as separate dosage forms. In particular embodiments for enhancing the activity of a taxane in treating a tumor or a cancer, the fatty acid synthase inhibitor is administered before a taxane is administered. In particular embodiments for enhancing the activity of a taxane in treating a tumor or a cancer, the fatty acid synthase inhibitor is administered after a taxane is administered.

As described above, in particular embodiments, the methods and compositions described herein are useful for increasing the sensitivity of a cancer cell to a taxane, the method comprising administering to a subject in need thereof, a therapeutically effective amount of a taxane and a fatty acid synthase inhibitor.

In some embodiments of the method for increasing the sensitivity of a cancer cell to a taxane, the fatty acid synthase inhibitor is a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In particular embodiments of the method for increasing the sensitivity of a cancer cell to a taxane, the fatty acid synthase inhibitor is a compound of Formula (I), (II), (III), (IV), (VII), (IX), (XIX), (XXI), (XXIII), (XXIV), (XXV), (XXVI), (XXVII), or (XXIX).

In particular embodiments of the method for increasing the sensitivity of a cancer cell to a taxane, the fatty acid synthase inhibitor is one or more compounds, forms, and/or agents that act as an inhibitor of FASN gene expression or FASN protein activity. The choice of FASN inhibitor agents that can be co-administered with a taxane can depend, at least in part, on the cancer being treated. In certain embodiments, a taxane can be administered, for example with cerulenin, C75, orlistat, C93 (FAS93). FAS31, C247, GSK837149A, platensimycin, EGCG, luteolin, taxifolin, kaempferol, quercetin, apigenin, catchin, soy protein, and oleic acid, or the like.

In particular embodiments of the method for increasing the sensitivity of a cancer cell to a taxane, the cancer cell is selected from the group consisting of a lung cancer cell, a breast cancer cell, an ovarian cancer cell, a prostate cancer cell, a colon cancer cell, and a pancreatic cancer cell. In a particular embodiment, the cancer cell is a lung cancer cell. In a particular embodiment, the cancer cell is a breast cancer cell. In a particular embodiment, the cancer cell is an ovarian cancer cell. In a particular embodiment, the cancer cell is a prostate cancer cell. In a particular embodiment, the cancer cell is a colon cancer cell. In a particular embodiment, the cancer cell is a pancreatic cancer cell.

In particular embodiments, the administration of a fatty acid synthase inhibitor increases the sensitivity of the cancer to a taxane by about 2 to 6 fold. In particular embodiments, the administration of a fatty acid synthase inhibitor increases the sensitivity of the cancer to a taxane by about 2 fold. In particular embodiments, the administration of a fatty acid synthase inhibitor increases the sensitivity of the cancer to a taxane by about 3 fold. In particular embodiments, the administration of a fatty acid synthase inhibitor increases the sensitivity of the cancer to a taxane by about 4 fold. In particular embodiments, the administration of a fatty acid synthase inhibitor increases the sensitivity of the cancer to a taxane by about 5 fold. In particular embodiments, the administration of a fatty acid synthase inhibitor increases the sensitivity of the cancer to a taxane by about 6 fold.

In some embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to a taxane by about 2 to 6 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to a taxane by about 2 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to a taxane by about 3 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to a taxane by about 4 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to a taxane by about 5 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to a taxane by about 6 fold.

In particular embodiments, the administration of a compound of Formula (I), (II), or (III) increases the sensitivity of the cancer to a taxane by about 2 to 6 fold. In particular embodiments, the administration of a compound of Formula (I), (II), or (III), increases the sensitivity of the cancer to a taxane by about 2 fold. In particular embodiments, the administration of a compound of Formula (I), (II), or (III) increases the sensitivity of the cancer to a taxane by about 3 fold. In particular embodiments, the administration of a compound of Formula (I), (II), or (III) increases the sensitivity of the cancer to a taxane by about 4 fold. In particular embodiments, the administration of a compound of Formula (I), (II), or (III) increases the sensitivity of the cancer to a taxane by about 5 fold. In particular embodiments, the administration of a compound of Formula (I), (II), or (III) increases the sensitivity of the cancer to a taxane by about 6 fold.

In particular embodiments of the method of the method for increasing the sensitivity of a cancer cell to a taxane, the fatty acid synthase inhibitor is administered simultaneously with a taxane. In particular embodiments, the fatty acid synthase inhibitor and a taxane are administered simultaneously as a single pharmaceutical composition. In particular embodiments, the fatty acid synthase inhibitor and a taxane are administered simultaneously as separate dosage forms of the method for increasing the sensitivity of a cancer cell to a taxane, the fatty acid synthase inhibitor is administered before a taxane is administered. In particular embodiments of the method for increasing the sensitivity of a cancer cell to a taxane, the fatty acid synthase inhibitor is administered after a taxane is administered.

The methods and compositions described herein are useful for treating or preventing a docetaxel-resistant tumor or cancer in a subject in need thereof, the method comprising administering to the subject in need thereof a therapeutically effective amount of a fatty acid synthase inhibitor. In particular embodiments, the method further comprises administering to the subject in need thereof a therapeutically effective amount of docetaxel.

Another aspect of the present invention relates to a method of treating or preventing a docetaxel-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating or preventing a docetaxel-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a docetaxel-resistant tumor or cancer in a subject, the fatty acid synthase inhibitor is a compound having the structure of any one of the compounds of Formula (I), (II), (III), (XIX), or (XXI). In particular embodiments of the method for treating or preventing a docetaxel-resistant tumor or cancer in a subject, the fatty acid synthase inhibitor is a compound having the structure of any one of the compounds of Formula (I), (II), or (III).

In other embodiments of the method for treating or preventing a docetaxel-resistant tumor or cancer a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating or preventing a docetaxel-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating or preventing a docetaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a docetaxel-resistant tumor in a subject, the fatty acid synthase inhibitor is a compound having the structure of any one of the compounds of Formula (I), (II), (III), (XIX), or (XXI). In particular embodiments of the method for treating or preventing a docetaxel-resistant tumor in a subject, the fatty acid synthase inhibitor is a compound having the structure of any one of the compounds of Formula (I), (II), or (III).

In other embodiments of the method for treating or preventing a docetaxel-resistant tumor a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating or preventing a docetaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating or preventing a docetaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a docetaxel-resistant cancer in a subject, the fatty acid synthase inhibitor is a compound having the structure of any one of the compounds of Formula (I), (II), (III), (XIX), or (XXI). In particular embodiments of the method for treating or preventing a docetaxel-resistant cancer in a subject, the fatty acid synthase inhibitor is a compound having the structure of any one of the compounds of Formula (I), (II), or (III).

In other embodiments of the method for treating or preventing a docetaxel-resistant cancer a subject in need thereof, the fatty acid synthase inhibitor is a pharmaceutical compositions comprising any one of the compounds of Formula (I), (II), (III), (IV), (V), (VI), (VII), (VII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a docetaxel-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating a docetaxel-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a docetaxel-resistant tumor or cancer in a subject, the fatty acid synthase inhibitor is a compound having the structure of any one of the compounds of Formula (I), (II), (III), (XIX), or (XXI). In particular embodiments of the method for treating a docetaxel-resistant tumor or cancer in a subject, the fatty acid synthase inhibitor is a compound having the structure of any one of the compounds of Formula (I), (II), or (III).

In other embodiments of the method for treating a docetaxel-resistant tumor or cancer a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a docetaxel-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating a docetaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a docetaxel-resistant tumor in a subject, the fatty acid synthase inhibitor is a compound having the structure of any one of the compounds of Formula (I), (II), (III), (XIX), or (XXI). In particular embodiments of the method for treating a docetaxel-resistant tumor in a subject, the fatty acid synthase inhibitor is a compound having the structure of any one of the compounds of Formula (I), (II), or (III).

In other embodiments of the method for treating a docetaxel-resistant tumor a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a docetaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating a docetaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a docetaxel-resistant cancer in a subject, the fatty acid synthase inhibitor is a compound having the structure of any one of the compounds of Formula (I), (II), (III), (XIX), or (XXI). In particular embodiments of the method for treating a docetaxel-resistant cancer in a subject, the fatty acid synthase inhibitor is a compound having the structure of any one of the compounds of Formula (I), (II), or (III).

In other embodiments of the method for treating a docetaxel-resistant cancer a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a docetaxel-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for preventing a docetaxel-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a docetaxel-resistant tumor or cancer in a subject, the fatty acid synthase inhibitor is a compound having the structure of any one of the compounds of Formula (I), (II), (III), (XIX), or (XXI). In particular embodiments of the method for preventing a docetaxel-resistant tumor or cancer in a subject, the fatty acid synthase inhibitor is a compound having the structure of any one of the compounds of Formula (I), (II), or (III).

In other embodiments of the method for preventing a docetaxel-resistant tumor or cancer a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a docetaxel-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for preventing a docetaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a docetaxel-resistant tumor in a subject, the fatty acid synthase inhibitor is a compound having the structure of any one of the compounds of Formula (I), (II), (III), (XIX), or (XXI). In particular embodiments of the method for preventing a docetaxel-resistant tumor in a subject, the fatty acid synthase inhibitor is a compound having the structure of any one of the compounds of Formula (I), (II), or (III).

In other embodiments of the method for preventing a docetaxel-resistant tumor a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a docetaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for preventing a docetaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a docetaxel-resistant cancer in a subject, the fatty acid synthase inhibitor is a compound having the structure of any one of the compounds of Formula (I), (II), (III), (XIX), or (XXI). In particular embodiments of the method for preventing a docetaxel-resistant cancer in a subject, the fatty acid synthase inhibitor is a compound having the structure of any one of the compounds of Formula (I), (II), or (III).

In other embodiments of the method for preventing a docetaxel-resistant cancer a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

In other embodiments, the methods and compositions described herein are useful for treating or preventing a docetaxel-resistant tumor or cancer in a subject in need thereof, the method comprising administering to the subject in need thereof a therapeutically effective amount of a fatty acid synthase inhibitor. In particular embodiments, the method further comprises administering to the subject in need thereof a therapeutically effective amount of docetaxel.

In particular embodiments of the method for treating docetaxel-resistant cancer in a subject, the fatty acid synthase inhibitor is one or more compounds, forms, and/or agents that act as an inhibitor of FASN gene expression or FASN protein activity. The choice of FASN inhibitor agents that can be co-administered with docetaxel can depend, at least in part, on the cancer being treated. In certain embodiments, docetaxel, can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for treating docetaxel-resistant cancer, the cancer is selected from the group consisting of lung cancer, breast cancer, ovarian cancer, prostate cancer, colon cancer, and pancreatic cancer. In further aspects, the tumor can be derived from thyroid, lymph node, kidney, ureter, bladder, ovary, teste, uterus, cervix, prostate, bone, skeletal muscle, bone marrow, blood, skin, stomach, head, neck, esophagus, small bowel, colon, rectum, pancreas, liver, bile duct, gallbladder, smooth muscle, brain, spinal cord, nerves, ear, eye, nasopharynx, oropharynx, salivary gland or heart tissue, or the cancer can be metastatic. In a particular embodiment, the docetaxel-resistant cancer is lung cancer. In a particular embodiment, the docetaxel-resistant cancer is breast cancer. In a particular embodiment, the docetaxel-resistant cancer is ovarian cancer. In a particular embodiment, the docetaxel-resistant cancer is prostate cancer. In a particular embodiment, the docetaxel-resistant cancer is colon cancer. In a particular embodiment, the docetaxel-resistant cancer is pancreatic cancer.

As described above, in some embodiments, the methods and compositions described herein are useful for treating or preventing a tumor or cancer in a subject who is docetaxel-resistant (or who has a docetaxel-resistant tumor or cancer), a subject who was previously administered or treated with a docetaxel (but not in combination with a compound of Formula (I), Formula (II), or Formula (III) as described herein), a subject who does not respond or has not responded favorably or adequately to docetaxel therapy, and/or a subject who failed therapy with docetaxel. Docetaxel therapy should be understood to include treatment with docetaxel. In certain embodiments, the subject was previously treated with docetaxel monotherapy or was previously treated with a docetaxel combination therapy that did not include treatment with a compound of Formula (I), Formula (II), or Formula (III) as described herein. In certain embodiments, the docetaxel-resistant subject initially responded to docetaxel therapy, but the subject eventually exhibited decreased or no response to the docetaxel therapy. In certain embodiments, the docetaxel-resistant tumor or cancer in the subject initially responded to docetaxel therapy, but the tumor or cancer eventually exhibited decreased or no response to the docetaxel therapy. The term "docetaxel-resistant subject" is used generally herein to indicate a subject who is docetaxel-resistant or who has a docetaxel-resistant tumor or cancer. As used herein, the term "docetaxel-resistant" means that the tumor or cancer does not or may not respond or has not responded favorably or adequately to docetaxel therapy. In certain embodiments, a docetaxel-resistant subject may be a docetaxel treatment naïve subject, or the docetaxel-resistant subject may have previously been treated with docetaxel therapy, and did not respond favorably or adequately, either initially or after some time period. In certain embodiments, a diagnostic may be used before docetaxel therapy to determine if the subject is docetaxel-resistant, or has a docetaxel-resistant tumor or cancer, or if the present invention would enhance the activity of docetaxel alone.

In particular embodiments of the method of treating or preventing a docetaxel-resistant tumor or cancer in a subject in need thereof, the fatty acid synthase inhibitor is administered simultaneously with docetaxel. In particular embodiments, the fatty acid synthase inhibitor and docetaxel are administered simultaneously as a single pharmaceutical composition. In particular embodiments, the fatty acid synthase inhibitor and docetaxel are administered simultaneously as separate dosage forms. In particular embodiments of the method of treating or preventing a docetaxel-resistant tumor or cancer in a subject in need thereof, the fatty acid synthase inhibitor is administered before docetaxel is administered. In particular embodiments of the method of treating or preventing a docetaxel-resistant tumor or cancer in a subject in need thereof, the fatty acid synthase inhibitor is administered after docetaxel is administered.

In particular embodiments, a method for treating a docetaxel-resistant tumor or cancer in a subject is provided, the method comprising:

(a) determining that the subject is docetaxel-resistant, or has a docetaxel-resistant tumor or cancer, and (b) administering to the subject in need thereof a therapeutically effective amount of a fatty acid synthase inhibitor.

In particular embodiments, Steps (a) and (b) can be performed in either order. That is, step (a) can be performed before step (b) or step (b) can be performed before step (a).

In particular embodiments of the method for treating a docetaxel-resistant tumor or cancer in a subject, the method further comprises administering to the subject in need thereof a therapeutically effective amount of docetaxel.

In particular embodiments of the method for treating a docetaxel-resistant tumor or cancer in a subject, the fatty acid synthase inhibitor is one or more compounds, forms, and/or agents that act as an inhibitor of FASN gene expression or FASN protein activity. The choice of FASN inhibitor agents that can be co-administered with docetaxel can depend, at least in part, on the cancer being treated. In certain embodiments, docetaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of any of the methods described herein for treating a docetaxel-resistant tumor or cancer, the docetaxel-resistant tumor or cancer is selected from the group consisting of lung cancer, breast cancer, ovarian cancer, prostate cancer, colon cancer, and pancreatic cancer. In a particular embodiment, the docetaxel-resistant tumor or cancer is lung cancer. In a particular embodiment, the docetaxel-resistant tumor or cancer is breast cancer. In a particular embodiment, the docetaxel-resistant tumor or cancer is ovarian cancer. In a particular embodiment, the docetaxel-resistant tumor or cancer is prostate cancer. In a particular embodiment, the docetaxel-resistant tumor or cancer is colon cancer. In a particular embodiment, the docetaxel-resistant tumor or cancer is pancreatic cancer.

In particular embodiments, a docetaxel-resistant tumor or cancer is determined by testing cells of the tumor or cancer for their responsiveness to docetaxel, e.g., the effect of docetaxel on the growth rate or amount of growth of the tumor or cancer cells. In one embodiment, testing the subject's cancer cells comprises contacting a sample of the subject's cancer cells with docetaxel and contacting a different sample of the subject's cancer cells with a negative control, e.g., an unrelated compound or vehicle only. In one embodiment, testing the subject's cancer cells comprises contacting a sample of the subject's cancer cells with docetaxel and contacting a different sample of the subject's cancer cells with a combination of docetaxel and a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and comparing the response between the two groups of cancer cells. In certain embodiments, the cells are tested as described in the accompanying Example. In particular embodiments, the cells are tested in vitro. In certain embodiments, the response of the cells to either docetaxel, negative control, or the combination of docetaxel and the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) that is measured and compared is the growth rate of the cells, the growth amount of the cells, or the viability of the cells. In certain embodiments, a tumor sample is docetaxel-resistant if the growth rate of the tumor cells, the growth amount of the tumor cells, or the viability of the tumor cells is not significantly decreased upon treatment with docetaxel as compared to treatment with the negative control. In certain embodiments, a tumor sample is docetaxel-resistant if the growth rate or the viability of the tumor cells is significantly decreased upon treatment with the combination of docetaxel and a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), as compared to treatment with docetaxel alone. In particular embodiments, a significant decrease is a decrease greater than or equal to 25%, greater than or equal to 50%, greater than or equal to 60%, greater than or equal to 70%, greater than or equal to 80%, greater than or equal to 90%, greater than or equal to 100%, greater than or equal to 150%, greater than or equal to 200%, or greater than or equal to 500% as compared to the relevant control.

In particular embodiments of the method of treating or preventing a docetaxel-resistant tumor or cancer in a subject in need thereof, wherein the subject has been determined to be docetaxel resistant or have a docetaxel-resistant tumor or cancer, the fatty acid synthase inhibitor is administered simultaneously with docetaxel. In particular embodiments, the fatty acid synthase inhibitor and docetaxel are administered simultaneously as a single pharmaceutical composition. In particular embodiments, the fatty acid synthase inhibitor and docetaxel are administered simultaneously as separate dosage forms. In particular embodiments of the method of treating or preventing a docetaxel-resistant tumor or cancer in a subject in need thereof, wherein the subject has been determined to be docetaxel resistant or have a docetaxel-resistant tumor or cancer, the fatty acid synthase inhibitor is administered before docetaxel is administered. In particular embodiments of the method of treating or preventing a docetaxel-resistant tumor or cancer in a subject in need thereof, wherein the subject has been determined to be docetaxel resistant or have a docetaxel-resistant tumor or cancer, the fatty acid synthase inhibitor is administered after docetaxel is administered.

As described above, in particular embodiments, the methods and compositions described herein are useful for treating or preventing a tumor or cancer in a subject in need thereof, the method comprising administering to the subject in need thereof a therapeutically effective amount of a fatty acid synthase inhibitor. In particular embodiments, the method further comprises administering to the subject in need thereof a therapeutically effective amount of docetaxel. In some embodiments of treating or preventing a tumor or cancer in a subject in need thereof, the fatty acid synthase inhibitor is a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In particular embodiments of treating or preventing a tumor or cancer in a subject in need thereof, the fatty acid synthase inhibitor is a compound of Formula (I), (II), (III), (IV), (VII), (IX), (XIX), (XXI), (XXIII), (XXIV), (XXV), (XXVI), (XXVII), or (XXIX).

In particular embodiments of the method for treating cancer in a subject, the fatty acid synthase inhibitor is one or more compounds, forms, and/or agents that act as an inhibitor of FASN gene expression or FASN protein activity. The choice of FASN inhibitor agents that can be co-administered with docetaxel can depend, at least in part, on the cancer being treated. In certain embodiments, docetaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for treating cancer, the cancer is selected from the group consisting of lung cancer, breast cancer, ovarian cancer, prostate cancer, colon cancer, and pancreatic cancer. In further aspects, the tumor can be derived from thyroid, lymph node, kidney, ureter, bladder, ovary, teste, uterus, cervix, prostate, bone, skeletal muscle, bone marrow, blood, skin, stomach, head, neck, esophagus, small bowel, colon, rectum, pancreas, liver, bile duct, gallbladder, smooth muscle, brain, spinal cord, nerves, ear, eye, nasopharynx, oropharynx, salivary gland or heart tissue, or the cancer can be metastatic. In a particular embodiment, the docetaxel-resistant cancer is lung cancer. In a particular embodiment, the docetaxel-resistant cancer is breast cancer. In a particular embodiment, the docetaxel-resistant cancer is ovarian cancer. In a particular embodiment, the docetaxel-resistant cancer is prostate cancer. In a particular embodiment, the docetaxel-resistant cancer is colon cancer. In a particular embodiment, the docetaxel-resistant cancer is pancreatic cancer.

In particular embodiments of the method of treating or preventing a tumor or cancer in a subject in need thereof, the fatty acid synthase inhibitor is administered simultaneously with docetaxel. In particular embodiments, the fatty acid synthase inhibitor and docetaxel are administered simultaneously as a single pharmaceutical composition. In particular embodiments, the fatty acid synthase inhibitor and docetaxel are administered simultaneously as separate dosage forms. In particular embodiments of the method of treating or preventing a tumor or cancer in a subject in need thereof, the fatty acid synthase inhibitor is administered before docetaxel is administered. In particular embodiments of the method of treating or preventing a tumor or cancer in a subject in need thereof, the fatty acid synthase inhibitor is administered after docetaxel is administered.

As described above, in particular embodiments, the methods and compositions described herein are useful for enhancing the activity of docetaxel in treating a tumor or a cancer, the method comprising administering to a subject in need thereof, a therapeutically effective amount of docetaxel and a fatty acid synthase inhibitor.

In some embodiments of the method for enhancing the activity of docetaxel in treating a tumor or a cancer, the fatty acid synthase inhibitor is a compound of Formula (I), (II), (III), (IV), (V), (VI), (VII), (VIII), (IX), (X) (XI), (XII), (XII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In particular embodiments of the method for enhancing the activity of docetaxel in treating a tumor or a cancer, the fatty acid synthase inhibitor is a compound of Formula (I), (II), (III), (IV), (VII), (IX), (XIX), (XXI), (XXIII), (XXIV), (XXV), (XXVI), (XXVII), or (XXIX).

In particular embodiments of the method for enhancing the activity of docetaxel in treating a tumor or a cancer, the fatty acid synthase inhibitor is one or more compounds, forms, and/or agents that act as an inhibitor of FASN gene expression or FASN protein activity. The choice of FASN inhibitor agents that can be co-administered with docetaxel can depend, at least in part, on the cancer being treated. In certain embodiments, docetaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for enhancing the activity of docetaxel in treating a tumor or a cancer, the cancer is selected from the group consisting of lung cancer, breast cancer, ovarian cancer, prostate cancer, colon cancer, and pancreatic cancer. In a particular embodiment, the cancer is lung cancer. In a particular embodiment, the cancer is breast cancer. In a particular embodiment, the cancer is ovarian cancer. In a particular embodiment, the cancer is prostate cancer. In a particular embodiment, the cancer is colon cancer. In a particular embodiment, the cancer is pancreatic cancer.

In particular embodiments of the method for enhancing the activity of docetaxel in treating a tumor or a cancer, the tumor or cancer is docetaxel-resistant. In certain embodiments, the docetaxel-resistant cancer is selected from the group consisting of lung cancer, breast cancer, ovarian cancer, prostate cancer, colon cancer, and pancreatic cancer. In a particular embodiment, the docetaxel-resistant cancer is lung cancer. In a particular embodiment, the docetaxel-resistant cancer is breast cancer. In a particular embodiment, the docetaxel-resistant cancer is ovarian cancer. In a particular embodiment, the docetaxel-resistant cancer is prostate cancer. In a particular embodiment, the docetaxel-resistant cancer is colon cancer. In a particular embodiment, the docetaxel-resistant cancer is pancreatic cancer.

In particular embodiments of the method for enhancing the activity of docetaxel in treating a tumor or a cancer, the fatty acid synthase inhibitor is administered simultaneously with docetaxel. In particular embodiments, the fatty acid synthase inhibitor and docetaxel are administered simultaneously as a single pharmaceutical composition. In particular embodiments, the fatty acid synthase inhibitor and docetaxel are administered simultaneously as separate dosage forms. In particular embodiments for enhancing the activity of docetaxel in treating a tumor or a cancer, the fatty acid synthase inhibitor is administered before docetaxel is administered. In particular embodiments for enhancing the activity of docetaxel in treating a tumor or a cancer, the fatty acid synthase inhibitor is administered after docetaxel is administered.

As described above, in particular embodiments, the methods and compositions described herein are useful for increasing the sensitivity of a cancer cell to docetaxel, the method comprising administering to a subject in need thereof, a therapeutically effective amount of docetaxel and a fatty acid synthase inhibitor.

In some embodiments of the method for increasing the sensitivity of a cancer cell to docetaxel, the fatty acid synthase inhibitor is a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In particular embodiments of the method for increasing the sensitivity of a cancer cell to docetaxel, the fatty acid synthase inhibitor is a compound of Formula (I), (II), (III), (IV), (VII), (IX), (XIX), (XXI), (XXIII), (XXIV), (XXV), (XXVI), (XXVII), or (XXIX).

In particular embodiments of the method for increasing the sensitivity of a cancer cell to docetaxel, the fatty acid synthase inhibitor is one or more compounds, forms, and/or agents that act as an inhibitor of FASN gene expression or FASN protein activity. The choice of FASN inhibitor agents that can be co-administered with docetaxel can depend, at least in part, on the cancer being treated. In certain embodiments, docetaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for increasing the sensitivity of a cancer cell to docetaxel, the cancer cell is selected from the group consisting of a lung cancer cell, a breast cancer cell, an ovarian cancer cell, a prostate cancer cell, a colon cancer cell, and a pancreatic cancer cell. In a particular embodiment, the cancer cell is a lung cancer cell. In a particular embodiment, the cancer cell is a breast cancer cell. In a particular embodiment, the cancer cell is an ovarian cancer cell. In a particular embodiment, the cancer cell is a prostate cancer cell. In a particular embodiment, the cancer cell is a colon cancer cell. In a particular embodiment, the cancer cell is a pancreatic cancer cell.

In particular embodiments, the administration of a fatty acid synthase inhibitor increases the sensitivity of the cancer to docetaxel by about 2 to 6 fold. In particular embodiments, the administration of a fatty acid synthase inhibitor increases the sensitivity of the cancer to docetaxel by about 2 fold. In particular embodiments, the administration of a fatty acid synthase inhibitor increases the sensitivity of the cancer to docetaxel by about 3 fold. In particular embodiments, the administration of a fatty acid synthase inhibitor increases the sensitivity of the cancer to docetaxel by about 4 fold. In particular embodiments, the administration of a fatty acid synthase inhibitor increases the sensitivity of the cancer to docetaxel by about 5 fold. In particular embodiments, the administration of a fatty acid synthase inhibitor increases the sensitivity of the cancer to docetaxel by about 6 fold.

In some embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to docetaxel by about 2 to 6 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to docetaxel by about 2 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to docetaxel by about 3 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to docetaxel by about 4 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to docetaxel by about 5 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to docetaxel by about 6 fold.

In particular embodiments, the administration of a compound of Formula (I), (II), or (III) increases the sensitivity of the cancer to docetaxel by about 2 to 6 fold. In particular embodiments, the administration of a compound of Formula (I), (II), or (III), increases the sensitivity of the cancer to docetaxel by about 2 fold. In particular embodiments, the administration of a compound of Formula (I), (II), or (III) increases the sensitivity of the cancer to docetaxel by about 3 fold. In particular embodiments, the administration of a compound of Formula (I), (II), or (III) increases the sensitivity of the cancer to docetaxel by about 4 fold. In particular embodiments, the administration of a compound of Formula (I), (II), or (III) increases the sensitivity of the cancer to docetaxel by about 5 fold. In particular embodiments, the administration of a compound of Formula (I), (II), or (III) increases the sensitivity of the cancer to docetaxel by about 6 fold.

In particular embodiments of the method of the method for increasing the sensitivity of a cancer cell to docetaxel, the fatty acid synthase inhibitor is administered simultaneously with docetaxel. In particular embodiments, the fatty acid synthase inhibitor and docetaxel are administered simultaneously as a single pharmaceutical composition. In particular embodiments, the fatty acid synthase inhibitor and docetaxel are administered simultaneously as separate dosage forms of the method for increasing the sensitivity of a cancer cell to docetaxel, the fatty acid synthase inhibitor is administered before docetaxel is administered. In particular embodiments of the method for increasing the sensitivity of a cancer cell to docetaxel, the fatty acid synthase inhibitor is administered after docetaxel is administered.

The methods and compositions described herein are useful for treating or preventing a cabazitaxel-resistant tumor or cancer in a subject in need thereof, the method comprising administering to the subject in need thereof a therapeutically effective amount of a fatty acid synthase inhibitor. In particular embodiments, the method further comprises administering to the subject in need thereof a therapeutically effective amount of cabazitaxel.

Another aspect of the present invention relates to a method of treating or preventing a cabazitaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating or preventing a cabazitaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a cabazitaxel-resistant cancer in a subject, the fatty acid synthase inhibitor is a compound having the structure of any one of the compounds of Formula (I), (II), (III), (XIX), or (XXI). In particular embodiments of the method for treating or preventing a cabazitaxel-resistant cancer in a subject, the fatty acid synthase inhibitor is a compound having the structure of any one of the compounds of Formula (I), (II), or (III).

In other embodiments of treating or preventing a cabazitaxel-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating or preventing a cabazitaxel-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating or preventing a cabazitaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a cabazitaxel-resistant tumor in a subject, the fatty acid synthase inhibitor is a compound having the structure of any one of the compounds of Formula (I), (II), (III), (XIX), or (XXI). In particular embodiments of the method for treating or preventing a cabazitaxel-resistant tumor in a subject, the fatty acid synthase inhibitor is a compound having the structure of any one of the compounds of Formula (I), (II), or (III).

In other embodiments of treating or preventing a cabazitaxel-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating or preventing a cabazitaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVII), (XIX), (XX), (XXI), (XXII), (XXIII), (XXIV), (XXV), (XXVI), (XXVII), (XXVIII), or (XXIX).

In other embodiments of the method for treating or preventing a cabazitaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a cabazitaxel-resistant cancer in a subject, the fatty acid synthase inhibitor is a compound having the structure of any one of the compounds of Formula (I), (II), (III), (XIX), or (XXI). In particular embodiments of the method for treating or preventing a cabazitaxel-resistant cancer in a subject, the fatty acid synthase inhibitor is a compound having the structure of any one of the compounds of Formula (I), (II), or (III).

In other embodiments of the method for treating or preventing a cabazitaxel-resistant cancer a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a cabazitaxel-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a cabazitaxel-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a cabazitaxel-resistant tumor or cancer in a subject, the fatty acid synthase inhibitor is a compound having the structure of any one of the compounds of Formula (I), (II), (III), (XIX), or (XXI). In particular embodiments of the method for treating a cabazitaxel-resistant tumor or cancer in a subject, the fatty acid synthase inhibitor is a compound having the structure of any one of the compounds of Formula (I), (II), or (III).

In other embodiments of the method for treating a cabazitaxel-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a cabazitaxel-resistant tumor in a subject in need thereof, the method comprising administering to the subject a fatty acid synthase inhibitor compound of any one of Formula (I), (II), (III), (IV), (V), (VI), (VII), (VII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a cabazitaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a cabazitaxel-resistant tumor in a subject, the fatty acid synthase inhibitor is a compound having the structure of any one of the compounds of Formula (I), (II), (III), (XIX), or (XXI). In particular embodiments of the method for treating a cabazitaxel-resistant tumor in a subject, the fatty acid synthase inhibitor is a compound having the structure of any one of the compounds of Formula (I), (II), or (III). In other embodiments of the method for treating a cabazitaxel-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a cabazitaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a cabazitaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a cabazitaxel-resistant cancer in a subject, the fatty acid synthase inhibitor is a compound having the structure of any one of the compounds of Formula (I), (II), (III), (XIX), or (XXI). In particular embodiments of the method for treating a cabazitaxel-resistant cancer in a subject, the fatty acid synthase inhibitor is a compound having the structure of any one of the compounds of Formula (I), (II), or (III).

In other embodiments of the method for treating a cabazitaxel-resistant cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a cabazitaxel-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a cabazitaxel-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a cabazitaxel-resistant tumor or cancer in a subject, the fatty acid synthase inhibitor is a compound having the structure of any one of the compounds of Formula (I), (II), (III), (XIX), or (XXI). In particular embodiments of the method for preventing a cabazitaxel-resistant tumor or cancer in a subject, the fatty acid synthase inhibitor is a compound having the structure of any one of the compounds of Formula (I), (II), or (III).

In other embodiments of the method for preventing a cabazitaxel-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a cabazitaxel-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a cabazitaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a cabazitaxel-resistant tumor in a subject, the fatty acid synthase inhibitor is a compound having the structure of any one of the compounds of Formula (I), (II), (III), (XIX), or (XXI). In particular embodiments of the method for preventing a cabazitaxel-resistant tumor in a subject, the fatty acid synthase inhibitor is a compound having the structure of any one of the compounds of Formula (I), (II), or (III).

In other embodiments of the method for preventing a cabazitaxel-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a cabazitaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a cabazitaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a cabazitaxel-resistant cancer in a subject, the fatty acid synthase inhibitor is a compound having the structure of any one of the compounds of Formula (I), (II), (III), (XIX), or (XXI). In particular embodiments of the method for preventing a cabazitaxel-resistant cancer in a subject, the fatty acid synthase inhibitor is a compound having the structure of any one of the compounds of Formula (I), (II), or (III).

In other embodiments of the method for preventing a cabazitaxel-resistant cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

In particular embodiments of the method for treating cabazitaxel-resistant cancer in a subject, the fatty acid synthase inhibitor is one or more compounds, forms, and/or agents that act as an inhibitor of FASN gene expression or FASN protein activity. The choice of FASN inhibitor agents that can be co-administered with cabazitaxel can depend, at least in part, on the cancer being treated. In certain embodiments, cabazitaxel, can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for treating cabazitaxel-resistant cancer, the cancer is selected from the group consisting of lung cancer, breast cancer, ovarian cancer, prostate cancer, colon cancer, and pancreatic cancer. In further aspects, the tumor can be derived from thyroid, lymph node, kidney, ureter, bladder, ovary, teste, uterus, cervix, prostate, bone, skeletal muscle, bone marrow, blood, skin, stomach, head, neck, esophagus, small bowel, colon, rectum, pancreas, liver, bile duct, gallbladder, smooth muscle, brain, spinal cord, nerves, ear, eye, nasopharynx, oropharynx, salivary gland or heart tissue, or the cancer can be metastatic. In a particular embodiment, the cabazitaxel-resistant cancer is lung cancer. In a particular embodiment, the cabazitaxel-resistant cancer is breast cancer. In a particular embodiment, the cabazitaxel-resistant cancer is ovarian cancer. In a particular embodiment, the cabazitaxel-resistant cancer is prostate cancer. In a particular embodiment, the cabazitaxel-resistant cancer is colon cancer. In a particular embodiment, the cabazitaxel-resistant cancer is pancreatic cancer.

As described above, in some embodiments, the methods and compositions described herein are useful for treating or preventing a tumor or cancer in a subject who is cabazitaxel-resistant (or who has a cabazitaxel-resistant tumor or cancer), a subject who was previously administered or treated with cabazitaxel (but not in combination with a compound of Formula (I), Formula (II), or Formula (III), etc. as described herein), a subject who does not respond or has not responded favorably or adequately to cabazitaxel therapy, and/or a subject who failed therapy with cabazitaxel. Cabazitaxel therapy should be understood to include treatment with cabazitaxel. In certain embodiments, the subject was previously treated with cabazitaxel monotherapy or was previously treated with a cabazitaxel combination therapy that did not include treatment with a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) as described herein. In certain embodiments, the cabazitaxel-resistant subject initially responded to cabazitaxel therapy, but the subject eventually exhibited decreased or no response to the cabazitaxel therapy. In certain embodiments, the cabazitaxel-resistant tumor or cancer in the subject initially responded to cabazitaxel therapy, but the tumor or cancer eventually exhibited decreased or no response to the cabazitaxel therapy. The term "cabazitaxel-resistant subject" is used generally herein to indicate a subject who is cabazitaxel-resistant or who has a cabazitaxel-resistant tumor or cancer. As used herein, the term "cabazitaxel-resistant" means that the tumor or cancer does not or may not respond or has not responded favorably or adequately to cabazitaxel therapy. In certain embodiments, a cabazitaxel-resistant subject may be a cabazitaxel treatment naïve subject, or the cabazitaxel-resistant subject may have previously been treated with cabazitaxel therapy, and did not respond favorably or adequately, either initially or after some time period. In certain embodiments, a diagnostic may be used before cabazitaxel therapy to determine if the subject is cabazitaxel-resistant, or has a cabazitaxel-resistant tumor or cancer, or if the present invention would enhance the activity of cabazitaxel alone.

In particular embodiments of the method of treating or preventing a cabazitaxel-resistant tumor or cancer in a subject in need thereof, the fatty acid synthase inhibitor is administered simultaneously with cabazitaxel. In particular embodiments, the fatty acid synthase inhibitor and cabazitaxel are administered simultaneously as a single pharmaceutical composition. In particular embodiments, the fatty acid synthase inhibitor and cabazitaxel are administered simultaneously as separate dosage forms. In particular embodiments of the method of treating or preventing a cabazitaxel-resistant tumor or cancer in a subject in need thereof, the fatty acid synthase inhibitor is administered before cabazitaxel is administered. In particular embodiments of the method of treating or preventing a cabazitaxel-resistant tumor or cancer in a subject in need thereof, the fatty acid synthase inhibitor is administered after cabazitaxel is administered.

In particular embodiments, a method for treating a cabazitaxel-resistant tumor or cancer in a subject is provided, the method comprising:

(a) determining that the subject is cabazitaxel-resistant, or has a cabazitaxel-resistant tumor or cancer, and (b) administering to the subject in need thereof a therapeutically effective amount of a fatty acid synthase inhibitor.

In particular embodiments, Steps (a) and (b) can be performed in either order. That is, step (a) can be performed before step (b) or step (b) can be performed before step (a).

In particular embodiments of the method for treating a cabazitaxel-resistant tumor or cancer in a subject, the fatty acid synthase inhibitor is one or more compounds, forms, and/or agents that act as an inhibitor of FASN gene expression or FASN protein activity. The choice of FASN inhibitor agents that can be co-administered with cabazitaxel can depend, at least in part, on the cancer being treated. In certain embodiments, cabazitaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of any of the methods described herein for treating a cabazitaxel-resistant tumor or cancer, the cabazitaxel-resistant tumor or cancer is selected from the group consisting of lung cancer, breast cancer, ovarian cancer, prostate cancer, colon cancer, and pancreatic cancer. In a particular embodiment, the cabazitaxel-resistant tumor or cancer is lung cancer. In a particular embodiment, the cabazitaxel-resistant tumor or cancer is breast cancer. In a particular embodiment, the cabazitaxel-resistant tumor or cancer is ovarian cancer. In a particular embodiment, the cabazitaxel-resistant tumor or cancer is prostate cancer. In a particular embodiment, the cabazitaxel-resistant tumor or cancer is colon cancer. In a particular embodiment, the cabazitaxel-resistant tumor or cancer is pancreatic cancer.

In particular embodiments, a cabazitaxel-resistant tumor or cancer is determined by testing cells of the tumor or cancer for their responsiveness to cabazitaxel, e.g., the effect of cabazitaxel on the growth rate or amount of growth of the tumor or cancer cells. In one embodiment, testing the subject's cancer cells comprises contacting a sample of the subject's cancer cells with cabazitaxel and contacting a different sample of the subject's cancer cells with a negative control, e.g., an unrelated compound or vehicle only. In one embodiment, testing the subject's cancer cells comprises contacting a sample of the subject's cancer cells with cabazitaxel and contacting a different sample of the subject's cancer cells with a combination of cabazitaxel and a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and comparing the response between the two groups of cancer cells. In certain embodiments, the cells are tested as described in the accompanying Example. In particular embodiments, the cells are tested in vitro. In certain embodiments, the response of the cells to either cabazitaxel, negative control, or the combination of cabazitaxel and the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) that is measured and compared is the growth rate of the cells, the growth amount of the cells, or the viability of the cells. In certain embodiments, a tumor sample is cabazitaxel-resistant if the growth rate of the tumor cells, the growth amount of the tumor cells, or the viability of the tumor cells is not significantly decreased upon treatment with cabazitaxel as compared to treatment with the negative control. In certain embodiments, a tumor sample is cabazitaxel-resistant if the growth rate or the viability of the tumor cells is significantly decreased upon treatment with the combination of cabazitaxel and a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), as compared to treatment with cabazitaxel alone. In particular embodiments, a significant decrease is a decrease greater than or equal to 25%, greater than or equal to 50%, greater than or equal to 60%, greater than or equal to 70%, greater than or equal to 80%, greater than or equal to 90%, greater than or equal to 100%, greater than or equal to 150%, greater than or equal to 200%, or greater than or equal to 500% as compared to the relevant control.

In particular embodiments of the method of treating or preventing a cabazitaxel-resistant tumor or cancer in a subject in need thereof, wherein the subject has been determined to be cabazitaxel resistant or have a cabazitaxel-resistant tumor or cancer, the fatty acid synthase inhibitor is administered simultaneously with cabazitaxel. In particular embodiments, the fatty acid synthase inhibitor and cabazitaxel are administered simultaneously as a single pharmaceutical composition. In particular embodiments, the fatty acid synthase inhibitor and cabazitaxel are administered simultaneously as separate dosage forms. In particular embodiments of the method of treating or preventing a cabazitaxel-resistant tumor or cancer in a subject in need thereof, wherein the subject has been determined to be cabazitaxel resistant or have a cabazitaxel-resistant tumor or cancer, the fatty acid synthase inhibitor is administered before cabazitaxel is administered. In particular embodiments of the method of treating or preventing a cabazitaxel-resistant tumor or cancer in a subject in need thereof, wherein the subject has been determined to be cabazitaxel resistant or have a cabazitaxel-resistant tumor or cancer, the fatty acid synthase inhibitor is administered after cabazitaxel is administered.

In particular embodiments, the methods and compositions described herein are useful for treating or preventing a tumor or cancer in a subject in need thereof, the method comprising administering to the subject in need thereof a therapeutically effective amount of a fatty acid synthase inhibitor. In particular embodiments, the method further comprises administering to the subject in need thereof a therapeutically effective amount of cabazitaxel. In some embodiments of treating or preventing a tumor or cancer in a subject in need thereof, the fatty acid synthase inhibitor is a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In particular embodiments of treating or preventing a tumor or cancer in a subject in need thereof, the fatty acid synthase inhibitor is a compound of Formula (I), (II), (III), (IV), (VII), (IX), (XIX), (XXI), (XXIII), (XXIV), (XXV), (XXVI), (XXVII), or (XXIX).

In particular embodiments, the methods and compositions described herein are useful for enhancing the activity of cabazitaxel in treating a tumor or a cancer, the method comprising administering to a subject in need thereof, a therapeutically effective amount of cabazitaxel and a fatty acid synthase inhibitor.

In some embodiments of the method for enhancing the activity of cabazitaxel in treating a tumor or a cancer, the fatty acid synthase inhibitor is a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In particular embodiments of the method for enhancing the activity of cabazitaxel in treating a tumor or a cancer, the fatty acid synthase inhibitor is a compound of Formula (I), (II), (III), (IV), (VII), (IX), (XIX), (XXI), (XXIII), (XXIV), (XXV), (XXVI), (XXVII), or (XXIX).

In particular embodiments of the method for enhancing the activity of cabazitaxel in treating a tumor or a cancer, the fatty acid synthase inhibitor is one or more compounds, forms, and/or agents that act as an inhibitor of FASN gene expression or FASN protein activity. The choice of FASN inhibitor agents that can be co-administered with cabazitaxel can depend, at least in part, on the cancer being treated. In certain embodiments, cabazitaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for enhancing the activity of cabazitaxel in treating a tumor or a cancer, the cancer is selected from the group consisting of lung cancer, breast cancer, ovarian cancer, prostate cancer, colon cancer, and pancreatic cancer. In a particular embodiment, the cancer is lung cancer. In a particular embodiment, the cancer is breast cancer. In a particular embodiment, the cancer is ovarian cancer. In a particular embodiment, the cancer is prostate cancer. In a particular embodiment, the cancer is colon cancer. In a particular embodiment, the cancer is pancreatic cancer.

In particular embodiments of the method for enhancing the activity of cabazitaxel in treating a tumor or a cancer, the tumor or cancer is cabazitaxel-resistant. In certain embodiments, the cabazitaxel-resistant cancer is selected from the group consisting of lung cancer, breast cancer, ovarian cancer, prostate cancer, colon cancer, and pancreatic cancer. In a particular embodiment, the cabazitaxel-resistant cancer is lung cancer. In a particular embodiment, the cabazitaxel-resistant cancer is breast cancer. In a particular embodiment, the cabazitaxel-resistant cancer is ovarian cancer. In a particular embodiment, the cabazitaxel-resistant cancer is prostate cancer. In a particular embodiment, the cabazitaxel-resistant cancer is colon cancer. In a particular embodiment, the cabazitaxel-resistant cancer is pancreatic cancer.

In particular embodiments of the method for enhancing the activity of cabazitaxel in treating a tumor or a cancer, the fatty acid synthase inhibitor is administered simultaneously with cabazitaxel. In particular embodiments, the fatty acid synthase inhibitor and cabazitaxel are administered simultaneously as a single pharmaceutical composition. In particular embodiments, the fatty acid synthase inhibitor and cabazitaxel are administered simultaneously as separate dosage forms. In particular embodiments for enhancing the activity of cabazitaxel in treating a tumor or a cancer, the fatty acid synthase inhibitor is administered before cabazitaxel is administered. In particular embodiments for enhancing the activity of cabazitaxel in treating a tumor or a cancer, the fatty acid synthase inhibitor is administered after cabazitaxel is administered.

As described above, in particular embodiments, the methods and compositions described herein are useful for increasing the sensitivity of a cancer cell to cabazitaxel, the method comprising administering to a subject in need thereof, a therapeutically effective amount of cabazitaxel and a fatty acid synthase inhibitor.

In some embodiments of the method for increasing the sensitivity of a cancer cell to cabazitaxel, the fatty acid synthase inhibitor is a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In particular embodiments of the method for increasing the sensitivity of a cancer cell to cabazitaxel, the fatty acid synthase inhibitor is a compound of Formula (I), (II), (III), (IV), (VII), (IX), (XIX), (XXI), (XXIII), (XXIV), (XXV), (XXVI), (XXVII), or (XXIX).

In particular embodiments of the method for increasing the sensitivity of a cancer cell to cabazitaxel, the fatty acid synthase inhibitor is one or more compounds, forms, and/or agents that act as an inhibitor of FASN gene expression or FASN protein activity. The choice of FASN inhibitor agents that can be co-administered with cabazitaxel can depend, at least in part, on the cancer being treated. In certain embodiments, cabazitaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for increasing the sensitivity of a cancer cell to cabazitaxel, the cancer cell is selected from the group consisting of a lung cancer cell, a breast cancer cell, an ovarian cancer cell, a prostate cancer cell, a colon cancer cell, and a pancreatic cancer cell. In a particular embodiment, the cancer cell is a lung cancer cell. In a particular embodiment, the cancer cell is a breast cancer cell. In a particular embodiment, the cancer cell is an ovarian cancer cell. In a particular embodiment, the cancer cell is a prostate cancer cell. In a particular embodiment, the cancer cell is a colon cancer cell. In a particular embodiment, the cancer cell is a pancreatic cancer cell.

In particular embodiments, the administration of a fatty acid synthase inhibitor increases the sensitivity of the cancer to cabazitaxel by about 2 to 6 fold. In particular embodiments, the administration of a fatty acid synthase inhibitor increases the sensitivity of the cancer to cabazitaxel by about 2 fold. In particular embodiments, the administration of a fatty acid synthase inhibitor increases the sensitivity of the cancer to cabazitaxel by about 3 fold. In particular embodiments, the administration of a fatty acid synthase inhibitor increases the sensitivity of the cancer to cabazitaxel by about 4 fold. In particular embodiments, the administration of a fatty acid synthase inhibitor increases the sensitivity of the cancer to cabazitaxel by about 5 fold. In particular embodiments, the administration of a fatty acid synthase inhibitor increases the sensitivity of the cancer to cabazitaxel by about 6 fold.

In some embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to cabazitaxel by about 2 to 6 fold. In particular embodiments, the administration of a compound of Formula (I), (II) (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to cabazitaxel by about 2 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVII), (XIX), (XX), (XXI), (XXII), (XXIII), (XXIV), (XXV), (XXVI), (XXVII), (XXVIII), or (XXIX) increases the sensitivity of the cancer to cabazitaxel by about 3 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to cabazitaxel by about 4 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to cabazitaxel by about 5 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to cabazitaxel by about 6 fold.

In particular embodiments, the administration of a compound of Formula (I), (II), or (III) increases the sensitivity of the cancer to cabazitaxel by about 2 to 6 fold. In particular embodiments, the administration of a compound of Formula (I), (II), or (III), increases the sensitivity of the cancer to cabazitaxel by about 2 fold. In particular embodiments, the administration of a compound of Formula (I), (II), or (III) increases the sensitivity of the cancer to cabazitaxel by about 3 fold. In particular embodiments, the administration of a compound of Formula (I), (II), or (III) increases the sensitivity of the cancer to cabazitaxel by about 4 fold. In particular embodiments, the administration of a compound of Formula (I), (II), or (III) increases the sensitivity of the cancer to cabazitaxel by about 5 fold. In particular embodiments, the administration of a compound of Formula (I), (II), or (III) increases the sensitivity of the cancer to cabazitaxel by about 6 fold.

In particular embodiments of the method of the method for increasing the sensitivity of a cancer cell to cabazitaxel, the fatty acid synthase inhibitor is administered simultaneously with cabazitaxel. In particular embodiments, the fatty acid synthase inhibitor and cabazitaxel are administered simultaneously as a single pharmaceutical composition. In particular embodiments, the fatty acid synthase inhibitor and cabazitaxel are administered simultaneously as separate dosage forms of the method for increasing the sensitivity of a cancer cell to cabazitaxel, the fatty acid synthase inhibitor is administered before cabazitaxel is administered. In particular embodiments of the method for increasing the sensitivity of a cancer cell to cabazitaxel, the fatty acid synthase inhibitor is administered after cabazitaxel is administered.

The methods and compositions described herein are useful for treating or preventing a paclitaxel-resistant tumor or cancer in a subject in need thereof, the method comprising administering to the subject in need thereof a therapeutically effective amount of a fatty acid synthase inhibitor. In particular embodiments, the method further comprises administering to the subject in need thereof a therapeutically effective amount of paclitaxel.

Another aspect of the present invention relates to a method of treating or preventing a paclitaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating or preventing a paclitaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX).

In other embodiments of treating or preventing a paclitaxel-resistant tumor or cancer in a subject in need thereof, the fatty acid synthase inhibitor is a compound having the structure of:

(a) Formula (I):

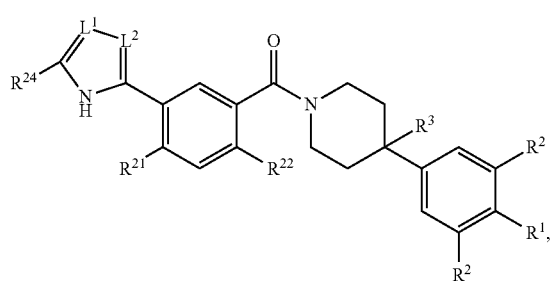

(I)

or
(b) Formula (II):

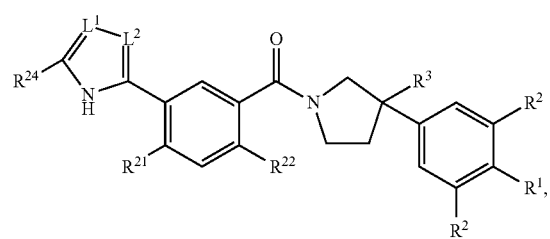

(II)

or (c) Formula (II):

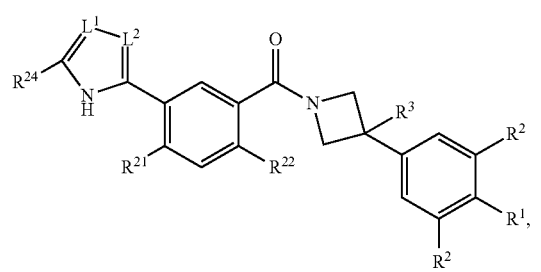

(III)

or a pharmaceutically acceptable salt thereof, wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is $CR^{23}$ or N;

$L^2$ is $CR^{23}$ or N;

at least one of $L^1$ or $L^2$ is N; and $R^{23}$ is H or $C_1$-$C_4$ straight or branched alkyl or (d) Formula (XXI):

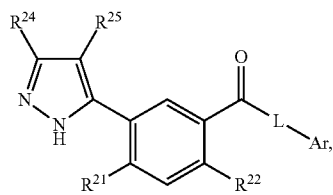

(XXI)

or a pharmaceutically acceptable salt thereof,
wherein:
L-Ar is

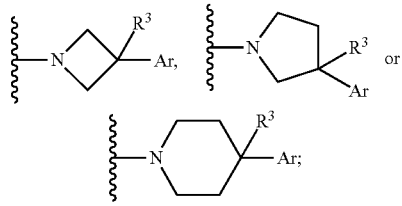

Ar is

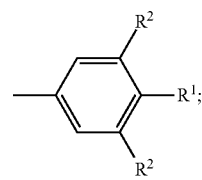

$R^1$ is H, —CN, halogen, $C_1$-$C_4$ alkyl, —O—($C_3$-$C_5$ cycloalkyl), —O-(4- to 6-membered heterocycle) or —O—

($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen;

or (e) Formula (XIX):

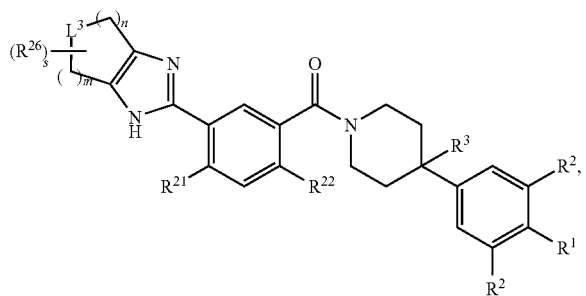

(XIX)

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: the $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^1$ is H, —OH or halogen;

$L^3$ is $C(R^{60})_2$, O or $NR^{50}$;

each $R^{60}$ is independently H, —OH, —CN, —$O_t$—($C_3$-$C_5$ cycloalkyl), —O—($C_1$-$C_4$ straight or branched alkyl), or —C(O)—$N(R^{61})_2$ wherein:

t is 0 or 1, and the $C_3$-$C_5$ cycloalkyl optionally includes an oxygen or nitrogen heteroatom;

each $R^{50}$ is independently H, —C(O)—$O_t$—($C_1$-$C_4$ straight or branched alkyl), —C(O)—$O_t$—($C_3$-$C_5$ cyclic alkyl), —$C_3$-$C_5$ cyclic alkyl optionally containing an oxygen or nitrogen heteroatom, —C(O)—$N(R^{501})_2$, $C_1$-$C_4$ straight or branched alkyl wherein:

t is 0 or 1, and the $C_3$-$C_5$ cycloalkyl optionally includes an oxygen or nitrogen heteroatom;

n is 1, 2 or 3;

m is 1 or 2;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom $R^{22}$ is H, halogen, $C_1$-$C_2$ alkyl;

each $R^{26}$ is independently —OH, —CN, halogen, $C_1$-$C_4$ straight or branched alkyl, —($C_1$-$C_4$ alkyl)$_t$-$O_t$—($C_3$-$C_5$ cycloalkyl), —($C_1$-$C_4$ alkyl)$_t$-O—($C_1$-$C_4$ straight or branched alkyl), —C(O)—$O_t$—($C_1$-$C_4$ alkyl), or —C(O)—$N(R^{501})_2$ wherein:

t is 0 or 1, and the $C_3$-$C_5$ cycloalkyl optionally includes an oxygen or nitrogen heteroatom;

s is 0, 1 or 2;

each $R^{601}$ and $R^{501}$ is independently H or $C_1$-$C_4$ straight or branched alkyl; and wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$.

In particular embodiments of treating or preventing a paclitaxel-resistant tumor or cancer in a subject in need thereof, the fatty acid synthase inhibitor is a compound having the structure of:

(a) Formula (I):

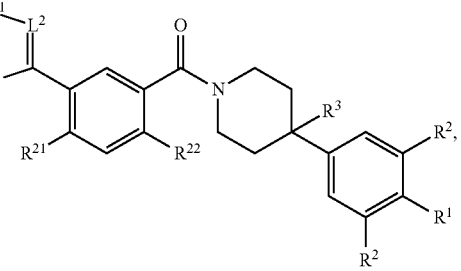

(I)

or (b) Formula (II):

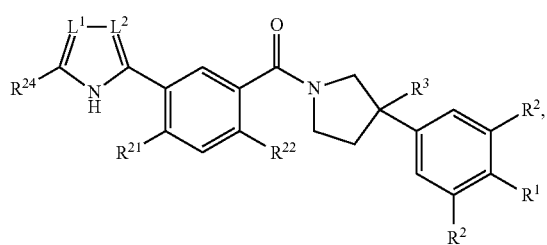

(II)

or (c) Formula (III):

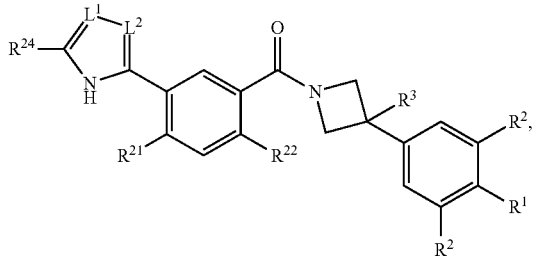

(III)

or a pharmaceutically acceptable salt thereof, wherein:

R¹ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when R¹ is not H, —CN or halogen, it is optionally substituted with one or more halogens;

each R² is independently hydrogen, halogen or $C_1$-$C_4$ straight or branched alkyl;

R³ is H, —OH, or halogen;

R²¹ is H, halogen, $C_1$-$C_4$ straight or branched alkyl, $C_3$-$C_5$ cycloalkyl wherein the
$C_3$-$C_5$ cycloalkyl optionally includes an oxygen or nitrogen heteroatom;

R²² is H, halogen, or $C_1$-$C_2$ alkyl;

R²⁴ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

L¹ is CR²³ or N;

L² is CR²³ or N;

at least one of L¹ or L² is N; and

R²³ is H or $C_1$-$C_4$ straight or branched alkyl.

In particular embodiments of treating or preventing paclitaxel-resistant a tumor or cancer in a subject in need thereof, R¹ is —CN, each R² is H, R³ is H or F, R²¹ is $C_3$-$C_4$ cycloalkyl, R²² is methyl. L¹ and L² are N, and R²⁴ is methyl, ethyl, hydroxymethyl, methoxymethyl, or 2-methoxyethyl.

In particular embodiments of the method for treating paclitaxel-resistant cancer in a subject, the compound having the structure of Formula (I) is:

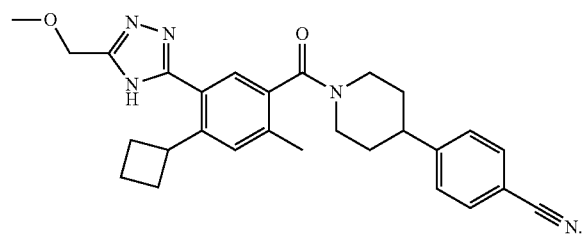

In particular embodiments of the method for treating paclitaxel-resistant cancer in a subject, the compound having the structure of Formula (I) is:

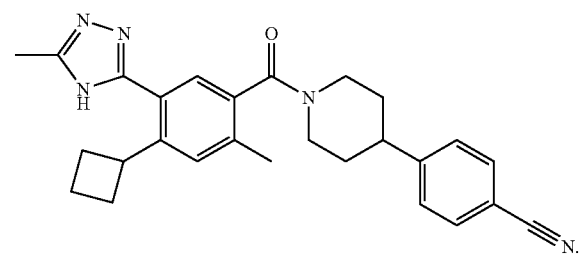 [SMILES: Cc1nnc(-c2cc(C(=O)N3CCC(c4ccc(C#N)cc4)CC3)c(C)cc2C2CCC2)[nH]1]

In particular embodiments of the method for treating paclitaxel-resistant cancer in a subject, the compound having the structure of Formula (I) is:

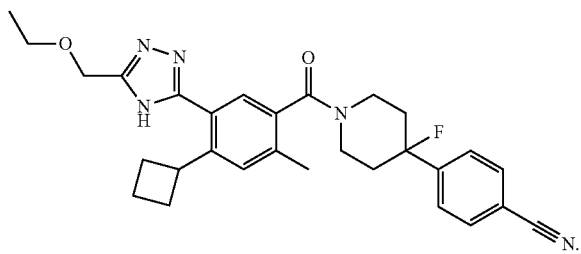

In particular embodiments of the method for treating paclitaxel-resistant cancer in a subject, the compound having the structure of Formula (I) is:

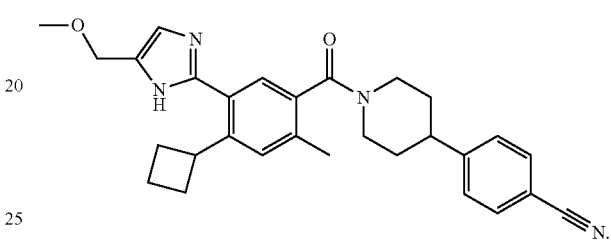

In particular embodiments of the method for treating paclitaxel-resistant cancer in a subject, the compound having the structure of Formula (III) is:

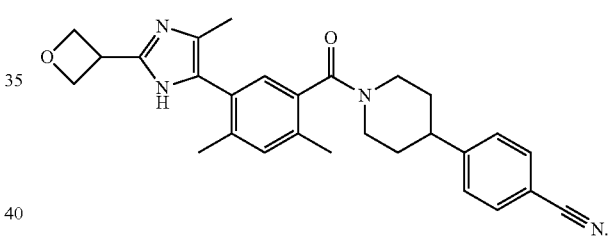

In other embodiments of treating or preventing a paclitaxel-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating or preventing a paclitaxel-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating or preventing a paclitaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a paclitaxel-resistant tumor in a subject, the fatty acid synthase inhibitor is a compound having the structure of any one of the compounds of Formula (I), (II), (III), (XIX), or (XXI). In particular embodiments of the method for treating or preventing a paclitaxel-resistant tumor in a subject, the fatty acid synthase inhibitor is a compound having the structure of any one of the compounds of Formula (I), (II), or (III).

In other embodiments of treating or preventing a paclitaxel-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating or preventing a paclitaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In other embodiments of the method for treating or preventing a paclitaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating or preventing a paclitaxel-resistant cancer in a subject, the fatty acid synthase inhibitor is a compound having the structure of any one of the compounds of Formula (I), (II), (III), (XIX), or (XXI). In particular embodiments of the method for treating or preventing a paclitaxel-resistant cancer in a subject, the fatty acid synthase inhibitor is a compound having the structure of any one of the compounds of Formula (I), (II), or (III).

In other embodiments of the method for treating or preventing a paclitaxel-resistant cancer a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a paclitaxel-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a paclitaxel-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a paclitaxel-resistant tumor or cancer in a subject, the fatty acid synthase inhibitor is a compound having the structure of any one of the compounds of Formula (I), (II), (III), (XIX), or (XXI). In particular embodiments of the method for treating a paclitaxel-resistant tumor or cancer in a subject, the fatty acid synthase inhibitor is a compound having the structure of any one of the compounds of Formula (I), (II), or (III).

In other embodiments of the method for treating a paclitaxel-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a paclitaxel-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a paclitaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a paclitaxel-resistant tumor in a subject, the fatty acid synthase inhibitor is a compound having the structure of any one of the compounds of Formula (I), (II), (III), (XIX), or (XXI). In particular embodiments of the method for treating a paclitaxel-resistant tumor in a subject, the fatty acid synthase inhibitor is a compound having the structure of any one of the compounds of Formula (I), (II), or (III).

In other embodiments of the method for treating a paclitaxel-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of treating a paclitaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for treating a paclitaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for treating a paclitaxel-resistant cancer in a subject, the fatty acid synthase inhibitor is a compound having the structure of any one of the compounds of Formula (I), (II), (III), (XIX), or (XXI). In particular embodiments of the method for treating a paclitaxel-resistant cancer in a subject, the fatty acid synthase inhibitor is a compound having the structure of any one of the compounds of Formula (I), (II), or (III).

In other embodiments of the method for treating a paclitaxel-resistant cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a paclitaxel-resistant tumor or cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a paclitaxel-resistant tumor or cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a paclitaxel-resistant tumor or cancer in a subject, the fatty acid synthase inhibitor is a compound having the structure of any one of the compounds of Formula (I), (II), (III), (XIX), or (XXI). In particular embodiments of the method for preventing a paclitaxel-resistant tumor or cancer in a subject, the fatty acid synthase inhibitor is a compound having the structure of any one of the compounds of Formula (I), (II), or (III).

In other embodiments of the method for preventing a paclitaxel-resistant tumor or cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a paclitaxel-resistant tumor in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a paclitaxel-resistant tumor in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a paclitaxel-resistant tumor in a subject, the fatty acid synthase inhibitor is a compound having the structure of any one of the compounds of Formula (I), (II), (III), (XIX), or (XXI). In particular embodiments of the method for preventing a paclitaxel-resistant tumor in a subject, the fatty acid synthase inhibitor is a compound having the structure of any one of the compounds of Formula (I), (II), or (III).

In other embodiments of the method for preventing a paclitaxel-resistant tumor in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

Another aspect of the present invention relates to a method of preventing a paclitaxel-resistant cancer in a subject in need thereof, the method comprising administering to the subject a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX).

In some embodiments of the method for preventing a paclitaxel-resistant cancer in a subject, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for preventing a paclitaxel-resistant cancer in a subject, the fatty acid synthase inhibitor is a compound having the structure of any one of the compounds of Formula (I), (II), (III), (XIX), or (XXI). In particular embodiments of the method for preventing a paclitaxel-resistant cancer in a subject, the fatty acid synthase inhibitor is a compound having the structure of any one of the compounds of Formula (I), (II), or (III).

In other embodiments of the method for preventing a paclitaxel-resistant cancer in a subject in need thereof, the fatty acid synthase inhibitor is a pharmaceutical compositions comprising any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) and a pharmaceutically acceptable carrier, excipient, or diluent.

In particular embodiments of the method for treating paclitaxel-resistant cancer in a subject, the fatty acid synthase inhibitor is one or more compounds, forms, and/or agents that act as an inhibitor of FASN gene expression or FASN protein activity. The choice of FASN inhibitor agents that can be co-administered with Nab-paclitaxel or paclitaxel can depend, at least in part, on the cancer being treated. In certain embodiments, Nab-paclitaxel and paclitaxel can be administered, for example with cerulenin, C75, orlistat, C93 (FAS93). FAS31, C247, GSK837149A, platensimycin, EGCG, luteolin, taxifolin, kaempferol, quercetin, apigenin, catchin, soy protein, and oleic acid, or the like.

In particular embodiments of the method for treating paclitaxel-resistant cancer, the cancer is selected from the group consisting of lung cancer, breast cancer, ovarian cancer, prostate cancer, colon cancer, and pancreatic cancer. In further aspects, the tumor can be derived from thyroid, lymph node, kidney, ureter, bladder, ovary, teste, uterus, cervix, prostate, bone, skeletal muscle, bone marrow, blood, skin, stomach, head, neck, esophagus, small bowel, colon, rectum, pancreas, liver, bile duct, gallbladder, smooth muscle, brain, spinal cord, nerves, ear, eye, nasopharynx, oropharynx, salivary gland or heart tissue, or the cancer can be metastatic. In a particular embodiment, the paclitaxel-resistant cancer is lung cancer. In a particular embodiment, the paclitaxel-resistant cancer is breast cancer. In a particular embodiment, the paclitaxel-resistant cancer is ovarian cancer. In a particular embodiment, the paclitaxel-resistant cancer is prostate cancer. In a particular embodiment, the paclitaxel-resistant cancer is colon cancer. In a particular embodiment, the paclitaxel-resistant cancer is pancreatic cancer.

As described above, in particular embodiments, the methods and compositions described herein are useful for treating or preventing a tumor or cancer in a subject who is paclitaxel-resistant (or who has a paclitaxel-resistant tumor or cancer), a subject who was previously administered or treated with paclitaxel (but not in combination with a compound of Formula (I), Formula (II), or Formula (III) as described herein), a subject who does not respond or has not responded favorably or adequately to paclitaxel therapy, and/or a subject who failed therapy with paclitaxel. Paclitaxel therapy should be understood to include treatment with any paclitaxel, e.g., Nab-paclitaxel. In certain embodiments, the subject was previously treated with paclitaxel monotherapy or was previously treated with a paclitaxel combination therapy that did not include treatment with a compound of Formula (I), Formula (II), or Formula (III) as described herein. In certain embodiments, the paclitaxel resistant subject initially responded to paclitaxel therapy, but the subject eventually exhibited decreased or no response to the paclitaxel therapy. In certain embodiments, the paclitaxel resistant tumor or cancer in the subject initially responded to paclitaxel therapy, but the tumor or cancer eventually exhibited decreased or no response to the paclitaxel therapy. The term "paclitaxel-resistant subject" is used generally herein to indicate a subject who is paclitaxel-resistant or who has a paclitaxel-resistant tumor or cancer. As used herein, the term "paclitaxel-resistant" means that the tumor or cancer does not or may not respond or has not responded favorably or adequately to paclitaxel therapy. In certain embodiments, a paclitaxel-resistant subject may be a paclitaxel treatment naïve subject, or the paclitaxel resistant subject may have previously been treated with paclitaxel therapy, and did not respond favorably or adequately, either initially or after some time period. In certain embodiments, a diagnostic may be used before paclitaxel therapy to determine if the subject is paclitaxel-resistant, or has a paclitaxel-resistant tumor or cancer, or if the present invention would enhance the activity of paclitaxel or Nab-paclitaxel alone.

In particular embodiments of the method of treating or preventing a paclitaxel-resistant tumor or cancer in a subject in need thereof, the fatty acid synthase inhibitor is administered simultaneously with Nab-paclitaxel or paclitaxel. In particular embodiments, the fatty acid synthase inhibitor and Nab-paclitaxel or paclitaxel are administered simultaneously as a single pharmaceutical composition. In particular embodiments, the fatty acid synthase inhibitor and Nab-paclitaxel or paclitaxel are administered simultaneously as separate dosage forms. In particular embodiments of the method of treating or preventing a paclitaxel-resistant tumor or cancer in a subject in need thereof, the fatty acid synthase inhibitor is administered before Nab-paclitaxel or paclitaxel is administered. In particular embodiments of the method of treating or preventing a paclitaxel-resistant tumor or cancer in a subject in need thereof, the fatty acid synthase inhibitor is administered after Nab-paclitaxel or paclitaxel is administered.

In particular embodiments, a method for treating a paclitaxel-resistant tumor or cancer in a subject is provided, the method comprising:
(a) determining that the subject is paclitaxel-resistant, or has a paclitaxel-resistant tumor or cancer, and
(b) administering to the subject in need thereof a therapeutically effective amount of a fatty acid synthase inhibitor.

In particular embodiments. Steps (a) and (b) can be performed in either order. That is, step (a) can be performed before step (b) or step (b) can be performed before step (a).

In particular embodiments of the method for treating a paclitaxel-resistant tumor or cancer in a subject, the method further comprises administering to the subject in need thereof a therapeutically effective mount of paclitaxel or Nab-paclitaxel.

In some embodiments of the method for treating a paclitaxel-resistant tumor or cancer in a subject, the fatty acid synthase inhibitor is a compound having the structure of any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In other embodiments of the method for treating a paclitaxel-resistant tumor or cancer in a subject, the fatty acid synthase inhibitor is a compound having the structure of any one of the compounds of Formula (I), (II), (III), (IV), (VII), (LX), (XIX), (XXI), (XXIII), (XXIV), (XXV), (XXVI), (XXVII), or (XXIX). In other embodiments of the method for treating a paclitaxel-resistant tumor or cancer in a subject, the fatty acid synthase inhibitor is a compound having the structure of any one of the compounds of Formula (I), (II), (III), (XIX), or (XXI).

In particular embodiments of the method for treating a paclitaxel-resistant tumor or cancer in a subject, the fatty acid synthase inhibitor is a compound having the structure of:

(a) Formula (I):

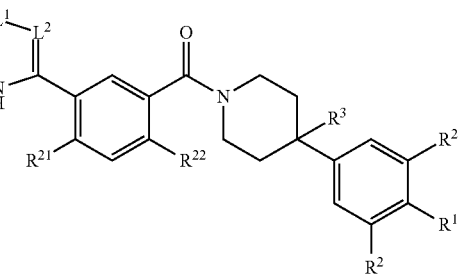

(I)

or (b) Formula (II):

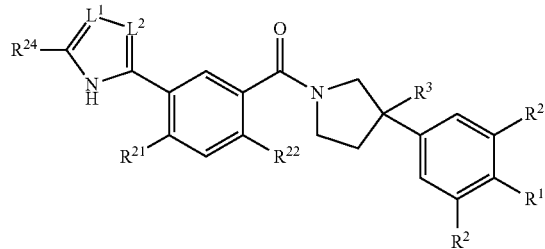

(II)

or (c) Formula (III):

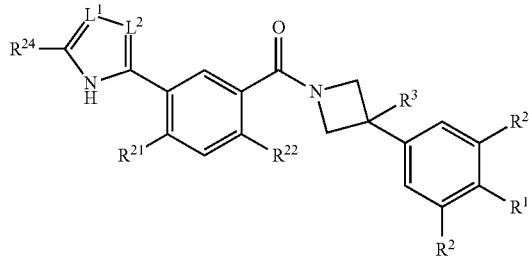

or a pharmaceutically acceptable salt thereof,
wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl)
wherein:

t is 0 or 1;

the $C_3$-$C_5$ cycloalkyl optionally includes an oxygen or nitrogen heteroatom;

$L^1$ is $CR^{23}$ or N;

$L^2$ is $CR^{23}$ or N;

at least one of $L^1$ or $L^2$ is N; and $R^{23}$ is H or $C_1$-$C_4$ straight or branched alkyl.

In particular embodiments of the method for treating a paclitaxel-resistant tumor or cancer in a subject, $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methyl, ethyl, hydroxymethyl, methoxymethyl, or 2-methoxyethyl.

In particular embodiments of the method for treating a paclitaxel-resistant tumor or cancer in a subject, the compound having the structure of Formula (I) is:

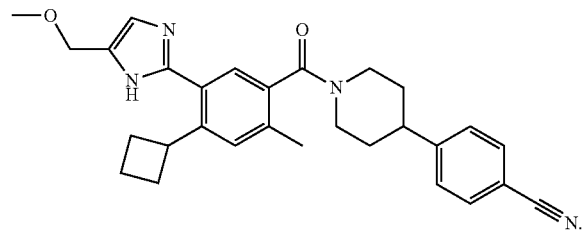 [SMILES: COCc1cnc(-c2cc(C(=O)N3CCC(c4ccc(C#N)cc4)CC3)c(C)cc2C2CCC2)[nH]1]

In particular embodiments of the method for treating a paclitaxel-resistant tumor or cancer in a subject, the compound having the structure of Formula (I) is:

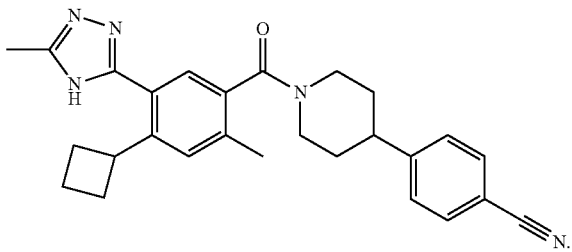

In particular embodiments of the method for treating a paclitaxel-resistant tumor or cancer in a subject, the compound having the structure of Formula (I) is:

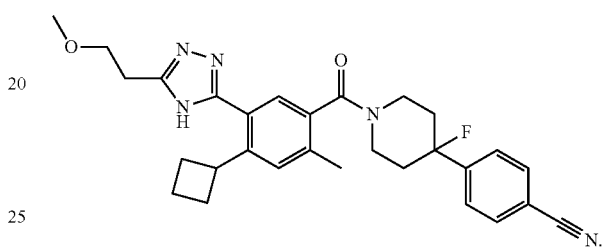

In particular embodiments of the method for treating a paclitaxel-resistant tumor or cancer in a subject, the compound having the structure of Formula (I) is:

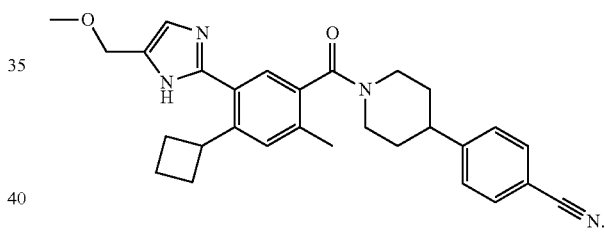

In particular embodiments of the method for treating a paclitaxel-resistant tumor or cancer in a subject, the compound having the structure of Formula (III) is:

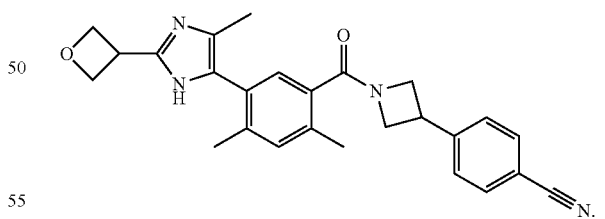

In particular embodiments of the method for treating a paclitaxel-resistant tumor or cancer in a subject, the fatty acid synthase inhibitor is one or more compounds, forms, and/or agents that act as an inhibitor of FASN gene expression or FASN protein activity. The choice of FASN inhibitor agents that can be co-administered with Nab-paclitaxel or paclitaxel can depend, at least in part, on the cancer being treated. In certain embodiments, Nab-paclitaxel and paclitaxel can be administered, for example with cerulenin, C75, orlistat, C93 (FAS93), FAS31, C247, GSK837149A, platensimycin. EGCG, luteolin, taxifolin, kaempferol, quercetin, apigenin, catchin, soy protein, and oleic acid, or the like.

In particular embodiments of any of the methods described herein for treating a paclitaxel-resistant tumor or cancer, the paclitaxel-resistant tumor or cancer is selected from the group consisting of lung cancer, breast cancer, ovarian cancer, prostate cancer, colon cancer, and pancreatic cancer. In a particular embodiment, the paclitaxel-resistant tumor or cancer is lung cancer. In a particular embodiment, the paclitaxel-resistant tumor or cancer is breast cancer. In a particular embodiment, the paclitaxel-resistant tumor or cancer is ovarian cancer. In a particular embodiment, the paclitaxel-resistant tumor or cancer is prostate cancer. In a particular embodiment, the paclitaxel-resistant tumor or cancer is colon cancer. In a particular embodiment, the paclitaxel-resistant tumor or cancer is pancreatic cancer.

In particular embodiments, a paclitaxel-resistant tumor or cancer is determined by testing cells of the tumor or cancer for their responsiveness to paclitaxel, e.g., the effect of paclitaxel on the growth rate or amount of growth of the tumor or cancer cells. In one embodiment, testing the subject's cancer cells comprises contacting a sample of the subject's cancer cells with paclitaxel and contacting a different sample of the subject's cancer cells with a negative control, e.g., an unrelated compound or vehicle only. In one embodiment, testing the subject's cancer cells comprises contacting a sample of the subject's cancer cells with paclitaxel and contacting a different sample of the subject's cancer cells with a combination of paclitaxel and a compound of Formula (I), Formula (II), or Formula (III) and comparing the response between the two groups of cancer cells. In certain embodiments, the cells are tested as described in the accompanying Example. In particular embodiments, the cells are tested in vitro. In certain embodiments, the response of the cells to either paclitaxel, negative control, or the combination of paclitaxel and the compounds of Formula (I). Formula (II), or Formula (III) that is measured and compared is the growth rate of the cells, the growth amount of the cells, or the viability of the cells. In certain embodiments, a tumor sample is paclitaxel-resistant if the growth rate of the tumor cells, the growth amount of the tumor cells, or the viability of the tumor cells is not significantly decreased upon treatment with paclitaxel as compared to treatment with the negative control. In certain embodiments, a tumor sample is paclitaxel-resistant if the growth rate or the viability of the tumor cells is significantly decreased upon treatment with the combination of paclitaxel and the compound of Formula (I), Formula (II), or Formula (III), as compared to treatment with paclitaxel alone. In particular embodiments, a significant decrease is a decrease greater than or equal to 25%, greater than or equal to 50%, greater than or equal to 60%, greater than or equal to 70%, greater than or equal to 80%, greater than or equal to 90%, greater than or equal to 100%, greater than or equal to 150%, greater than or equal to 200%, or greater than or equal to 500% as compared to the relevant control.

In particular embodiments of the method of treating or preventing a paclitaxel-resistant tumor or cancer in a subject in need thereof, wherein the subject has been determined to be paclitaxel resistant or have a paclitaxel-resistant tumor or cancer, the fatty acid synthase inhibitor is administered simultaneously with Nab-paclitaxel or paclitaxel. In particular embodiments, the fatty acid synthase inhibitor and Nab-paclitaxel or paclitaxel are administered simultaneously as a single pharmaceutical composition. In particular embodiments, the fatty acid synthase inhibitor and Nab-paclitaxel or paclitaxel are administered simultaneously as separate dosage forms. In particular embodiments of the method of treating or preventing a paclitaxel-resistant tumor or cancer in a subject in need thereof, wherein the subject has been determined to be paclitaxel resistant or have a paclitaxel-resistant tumor or cancer, the fatty acid synthase inhibitor is administered before Nab-paclitaxel or paclitaxel is administered. In particular embodiments of the method of treating or preventing a paclitaxel-resistant tumor or cancer in a subject in need thereof, wherein the subject has been determined to be paclitaxel resistant or have a paclitaxel-resistant tumor or cancer, the fatty acid synthase inhibitor is administered after Nab-paclitaxel or paclitaxel is administered.

As described above, in particular embodiments, the methods and compositions described herein are useful for treating or preventing a tumor or cancer in a subject in need thereof, the method comprising administering to the subject in need thereof a therapeutically effective amount of a fatty acid synthase inhibitor. In particular embodiments, the method further comprises administering to the subject in need thereof a therapeutically effective amount of paclitaxel or Nab-paclitaxel.

In some embodiments of treating or preventing a tumor or cancer in a subject in need thereof, the fatty acid synthase inhibitor is a compound having the structure of any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In other embodiments of treating or preventing a tumor or cancer in a subject in need thereof, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of treating or preventing a tumor or cancer in a subject in need thereof, the fatty acid synthase inhibitor is a compound having the structure of any one of the compounds of Formula (I), (II), (III), (XIX), or (XXI).

In particular embodiments of treating or preventing a tumor or cancer in a subject in need thereof, the fatty acid synthase inhibitor is a compound having the structure of:

(a) Formula (I):

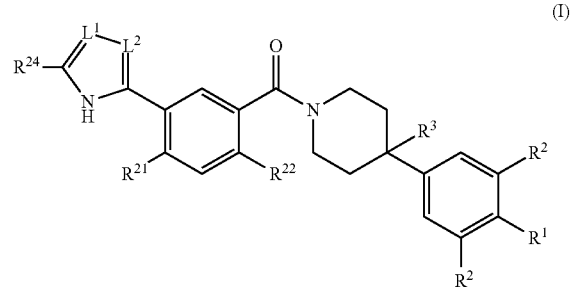

(I)

or
(b) Formula (II):

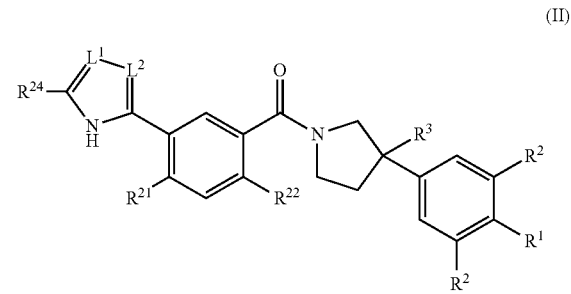

(II)

or
(c) Formula (III):

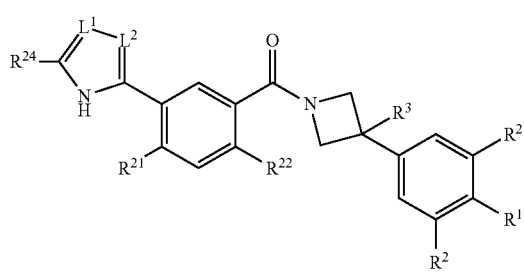

or a pharmaceutically acceptable salt thereof,
wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when $R^1$ is not H, —CN or halogen, it is optionally substituted with one or more halogens;
each $R^2$ is independently hydrogen, halogen or $C_1$-$C_4$ straight or branched alkyl;
$R^3$ is H, —OH, or halogen;
$R^{21}$ is H, halogen, $C_1$-$C_4$ straight or branched alkyl, $C_3$-$C_5$ cycloalkyl wherein the
$C_3$-$C_5$ cycloalkyl optionally includes an oxygen or nitrogen heteroatom;
$R^{22}$ is H, halogen, or $C_1$-$C_2$ alkyl;
$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:
t is 0 or 1;
the $C_3$-$C_5$ cycloalkyl optionally includes an oxygen or nitrogen heteroatom;
$L^1$ is $CR^{23}$ or N;
$L^2$ is $CR^{23}$ or N;
at least one of $L^1$ or $L^2$ is N; and
$R^{23}$ is H or $C_1$-$C_4$ straight or branched alkyl.

In particular embodiments of treating or preventing a tumor or cancer in a subject in need thereof, $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methyl, ethyl, hydroxymethyl, methoxymethyl, or 2-methoxyethyl.

In some embodiments of treating cancer in a subject in need thereof, the fatty acid synthase inhibitor is a compound having the structure of any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In other embodiments of treating cancer in a subject in need thereof, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of treating cancer in a subject in need thereof, the fatty acid synthase inhibitor is a compound having the structure of any one of the compounds of Formula (I), (II), (III), (XIX), or (XXI).

In particular embodiments of the method for treating cancer in a subject, the compound having the structure of Formula (I) is:

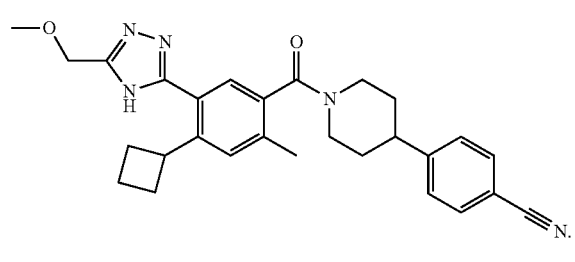

In particular embodiments of the method for treating cancer in a subject, the compound having the structure of Formula (I) is:

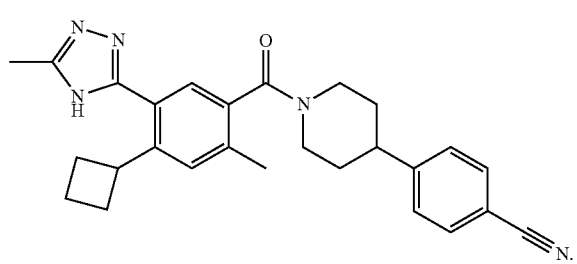 [SMILES: Cc1nnc(-c2cc(C(=O)N3CCC(c4ccc(C#N)cc4)CC3)c(C)cc2C2CCC2)[nH]1]

In particular embodiments of the method for treating cancer in a subject, the compound having the structure of Formula (I) is:

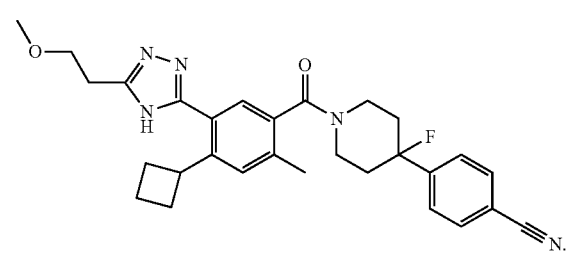 [SMILES: COCCc1nnc(-c2cc(C(=O)N3CCC(F)(c4ccc(C#N)cc4)CC3)c(C)cc2C2CCC2)[nH]1]

In particular embodiments of the method for treating cancer in a subject, the compound having the structure of Formula (I) is:

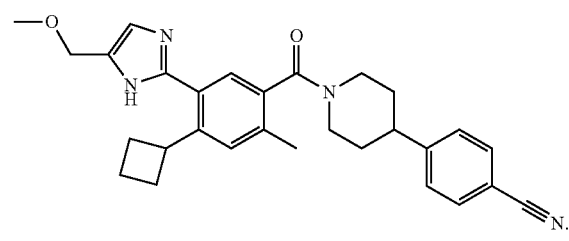 [SMILES: COCc1cnc(-c2cc(C(=O)N3CCC(c4ccc(C#N)cc4)CC3)c(C)cc2C2CCC2)[nH]1]

In particular embodiments of the method for treating cancer in a subject, the compound having the structure of Formula (III) is:

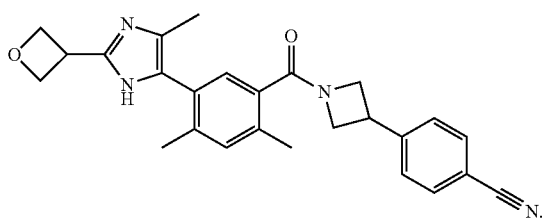 [SMILES: Cc1cc(C)c(-c2[nH]c(C3COC3)nc2C)cc1C(=O)N1CC(c2ccc(C#N)cc2)C1]

In particular embodiments of the method for treating cancer in a subject, the fatty acid synthase inhibitor is one or more compounds, forms, and/or agents that act as an inhibitor of FASN gene expression or FASN protein activity. The choice of FASN inhibitor agents that can be co-administered with Nab-paclitaxel or paclitaxel can depend, at least in part, on the cancer being treated. In certain embodiments, Nab-paclitaxel and paclitaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for treating cancer, the cancer is selected from the group consisting of lung cancer, breast cancer, ovarian cancer, prostate cancer, colon cancer, and pancreatic cancer. In further aspects, the tumor can be derived from thyroid, lymph node, kidney, ureter, bladder, ovary, teste, uterus, cervix, prostate, bone, skeletal muscle, bone marrow, blood, skin, stomach, head, neck, esophagus, small bowel, colon, rectum, pancreas, liver, bile duct, gallbladder, smooth muscle, brain, spinal cord, nerves, ear, eye, nasopharynx, oropharynx, salivary gland or heart tissue, or the cancer can be metastatic. In a particular embodiment, the paclitaxel-resistant cancer is lung cancer. In a particular embodiment, the paclitaxel-resistant cancer is breast cancer. In a particular embodiment, the paclitaxel-resistant cancer is ovarian cancer. In a particular embodiment, the paclitaxel-resistant cancer is prostate cancer. In a particular embodiment, the paclitaxel-resistant cancer is colon cancer. In a particular embodiment, the paclitaxel-resistant cancer is pancreatic cancer.

In particular embodiments of the method of treating or preventing a tumor or cancer in a subject in need thereof, the fatty acid synthase inhibitor is administered simultaneously with Nab-paclitaxel or paclitaxel. In particular embodiments, the fatty acid synthase inhibitor and Nab-paclitaxel or paclitaxel are administered simultaneously as a single pharmaceutical composition. In particular embodiments, the fatty acid synthase inhibitor and Nab-paclitaxel or paclitaxel are administered simultaneously as separate dosage forms. In particular embodiments of the method of treating or preventing a tumor or cancer in a subject in need thereof, the fatty acid synthase inhibitor is administered before Nab-paclitaxel or paclitaxel is administered. In particular embodiments of the method of treating or preventing a tumor or cancer in a subject in need thereof, the fatty acid synthase inhibitor is administered after Nab-paclitaxel or paclitaxel is administered.

As described above, in particular embodiments, the methods and compositions described herein are useful for enhancing the activity of paclitaxel or Nab-paclitaxel in treating a tumor or a cancer, the method comprising administering to a subject in need thereof, a therapeutically effective amount of Nab-paclitaxel or paclitaxel and a fatty acid synthase inhibitor.

In some embodiments of the method for enhancing the activity of paclitaxel or Nab-paclitaxel in treating a tumor or a cancer, the fatty acid synthase inhibitor is a compound having the structure of any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In other embodiments of the method for enhancing the activity of paclitaxel or Nab-paclitaxel in treating a tumor or a cancer, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for enhancing the activity of paclitaxel or Nab-paclitaxel in treating a tumor or a cancer, the fatty acid synthase inhibitor is a compound having the structure of any one of the compounds of Formula (I), (II), (III), (XIX), or (XXI).

In particular embodiments of the method for enhancing the activity of paclitaxel or Nab-paclitaxel in treating a tumor or a cancer, the fatty acid synthase inhibitor is a compound having the structure of:

(a) Formula (I):

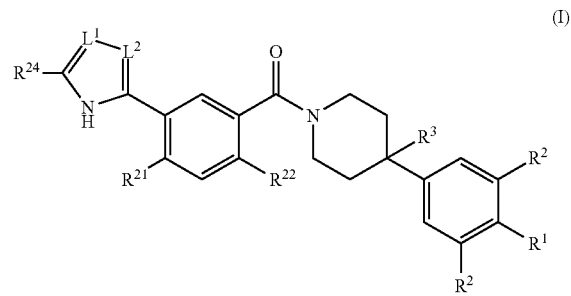

Or
(b) Formula II):

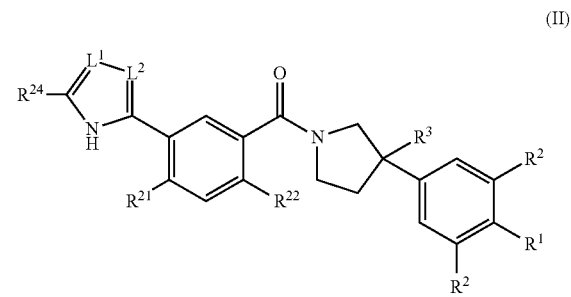

or
(c) Formula (III):

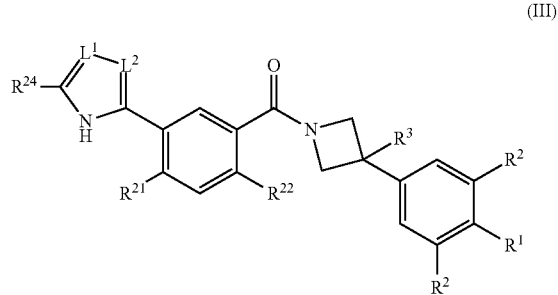

or a pharmaceutically acceptable salt thereof, wherein:

R¹ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when R¹ is not H, —CN or halogen, it is optionally substituted with one or more halogens;

each R² is independently hydrogen, halogen or $C_1$-$C_4$ straight or branched alkyl;

R³ is H, —OH, or halogen;

R²¹ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

R²² is H, halogen, or $C_1$-$C_2$ alkyl;

R²⁴ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

L¹ is CR²³ or N;

L² is CR²³ or N;

at least one of L¹ or L² is N; and

R²³ is H or $C_1$-$C_4$ straight or branched alkyl.

In particular embodiments of the method for enhancing the activity of paclitaxel or Nab-paclitaxel in treating a tumor or a cancer, R¹ is —CN, each R² is H, R³ is H or F, R²¹ is $C_3$-$C_4$ cycloalkyl, R²² is methyl, L¹ and L² are N, and R²⁴ is methyl, ethyl, hydroxymethyl, methoxymethyl, or 2-methoxyethyl.

In particular embodiments of the method for enhancing the activity of paclitaxel or Nab-paclitaxel in treating a tumor or a cancer, the compound having structure (I) is:

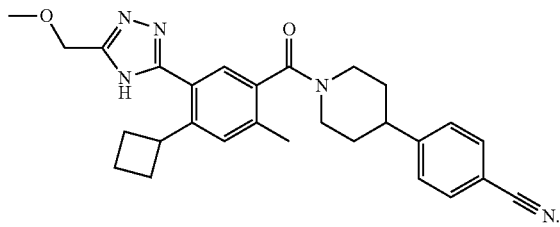

In particular embodiments of the method for enhancing the activity of paclitaxel or Nab-paclitaxel in treating a tumor or a cancer, the compound having structure (I) is:

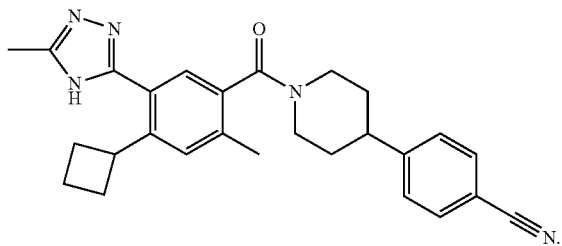 [SMILES: Cc1nnc(-c2cc(C(=O)N3CCC(c4ccc(C#N)cc4)CC3)c(C)cc2C2CCC2)[nH]1]

In particular embodiments of the method for enhancing the activity of paclitaxel or Nab-paclitaxel in treating a tumor or a cancer, the compound having structure (I) is:

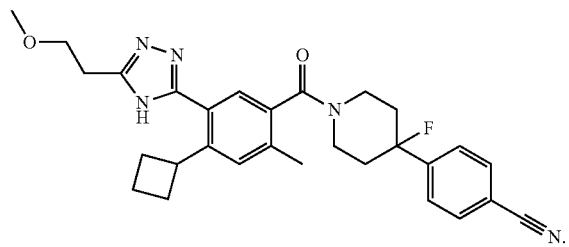 [SMILES: COCCc1nnc(-c2cc(C(=O)N3CCC(F)(c4ccc(C#N)cc4)CC3)c(C)cc2C2CCC2)[nH]1]

In particular embodiments of the method for enhancing the activity of paclitaxel or Nab-paclitaxel in treating a tumor or a cancer, the compound having structure (I) is:

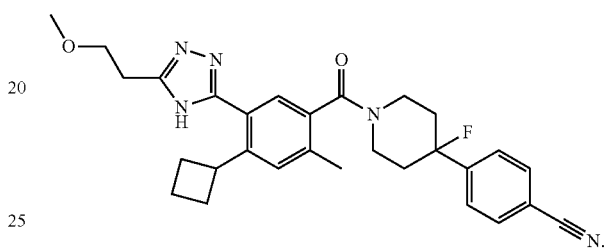

In particular embodiments of the method for enhancing the activity of paclitaxel or Nab-paclitaxel in treating a tumor or a cancer, the compound having structure (III) is:

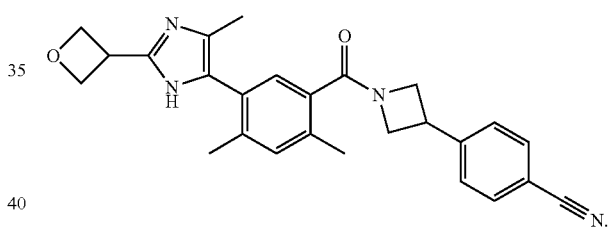

In particular embodiments of the method for enhancing the activity of paclitaxel or Nab-paclitaxel in treating a tumor or a cancer, the fatty acid synthase inhibitor is one or more compounds, forms, and/or agents that act as an inhibitor of FASN gene expression or FASN protein activity. The choice of FASN inhibitor agents that can be co-administered with Nab-paclitaxel or paclitaxel can depend, at least in part, on the cancer being treated. In certain embodiments, Nab-paclitaxel and paclitaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for enhancing the activity of paclitaxel or Nab-paclitaxel in treating a tumor or a cancer, the cancer is selected from the group consisting of lung cancer, breast cancer, ovarian cancer, prostate cancer, colon cancer, and pancreatic cancer. In a particular embodiment, the cancer is lung cancer. In a particular embodiment, the cancer is breast cancer. In a particular embodiment, the cancer is ovarian cancer. In a particular embodiment, the cancer is prostate cancer. In a particular embodiment, the cancer is colon cancer. In a particular embodiment, the cancer is pancreatic cancer.

In particular embodiments of the method for enhancing the activity of paclitaxel or Nab-paclitaxel in treating a tumor or a cancer, the tumor or cancer is paclitaxel-resistant. In certain embodiments, the paclitaxel-resistant cancer is selected from the group consisting of lung cancer, breast cancer, ovarian cancer, prostate cancer, colon cancer, and pancreatic cancer. In a particular embodiment, the paclitaxel-resistant cancer is lung cancer. In a particular embodiment, the paclitaxel-resistant cancer is breast cancer. In a particular embodiment, the paclitaxel-resistant cancer is ovarian cancer. In a particular embodiment, the paclitaxel-resistant cancer is prostate cancer. In a particular embodiment, the paclitaxel-resistant cancer is colon cancer. In a particular embodiment, the paclitaxel-resistant cancer is pancreatic cancer.

In particular embodiments of the method for enhancing the activity of paclitaxel or Nab-paclitaxel in treating a tumor or a cancer, the fatty acid synthase inhibitor is administered simultaneously with Nab-paclitaxel or paclitaxel. In particular embodiments, the fatty acid synthase inhibitor and Nab-paclitaxel or paclitaxel are administered simultaneously as a single pharmaceutical composition. In particular embodiments, the fatty acid synthase inhibitor and Nab-paclitaxel or paclitaxel are administered simultaneously as separate dosage forms. In particular embodiments for enhancing the activity of paclitaxel or Nab-paclitaxel in treating a tumor or a cancer, the fatty acid synthase inhibitor is administered before Nab-paclitaxel or paclitaxel is administered. In particular embodiments for enhancing the activity of paclitaxel or Nab-paclitaxel in treating a tumor or a cancer, the fatty acid synthase inhibitor is administered after Nab-paclitaxel or paclitaxel is administered.

As described above, in particular embodiments, the methods and compositions described herein are useful for increasing the sensitivity of a cancer cell to paclitaxel or Nab-paclitaxel, the method comprising administering to a subject in need thereof, a therapeutically effective amount of Nab-paclitaxel or paclitaxel and a fatty acid synthase inhibitor.

In some embodiments of the method for increasing the sensitivity of a cancer cell to paclitaxel or Nab-paclitaxel, the fatty acid synthase inhibitor is a compound having the structure of any one of the compounds of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX). In other embodiments of the method for increasing the sensitivity of a cancer cell to paclitaxel or Nab-paclitaxel, the fatty acid synthase inhibitor is a compound having the structure of any one of the compounds of Formula (I), (II), (III), (IV), (VII), (IX), (XIX), (XXI), (XXIII), (XXIV), (XXV), (XXVI), (XXVII), or (XXIX). In other embodiments of the method for increasing the sensitivity of a cancer cell to paclitaxel or Nab-paclitaxel, the fatty acid synthase inhibitor is a compound having the structure of any one of the compounds of Formula (I), (II), (III), (XIX), or (XXI).

In particular embodiments of the method for increasing the sensitivity of a cancer cell to paclitaxel or Nab-paclitaxel, the fatty acid synthase inhibitor is a compound having the structure of:

(a) Formula (I):

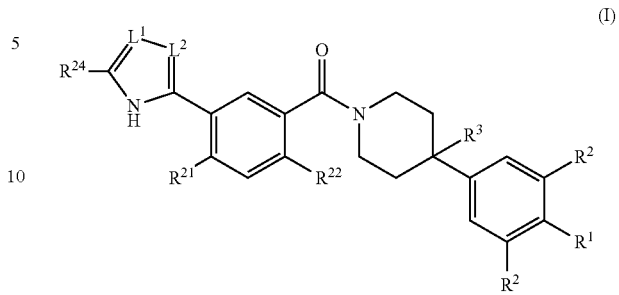

or
(b) Formula (II):

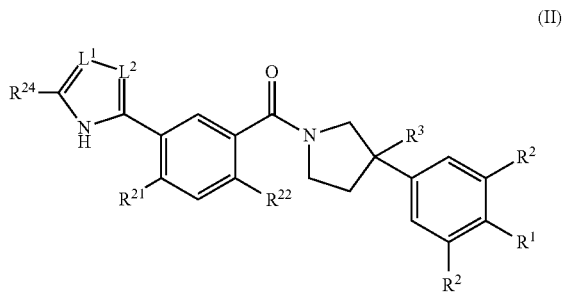

or
(c) Formula (III):

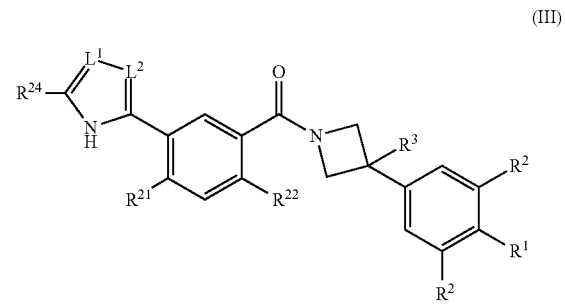

or a pharmaceutically acceptable salt thereof,
wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein: $C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH, —($C_1$-$C_4$ alkyl)$_t$-$O_t$—($C_3$-$C_5$ cycloalkyl), or —($C_1$-$C_4$ alkyl)$_t$-O—($C_1$-$C_4$ straight or branched alkyl) wherein:

t is 0 or 1;

the $C_3$-$C_5$ cycloalkyl optionally includes an oxygen or nitrogen heteroatom;

$L^1$ is $CR^{23}$ or N;

$L^2$ is $CR^{23}$ or N;

at least one of $L^1$ or $L^2$ is N; and $R^{23}$ is H or $C_1$-$C_4$ straight or branched alkyl.

In particular embodiments of the method for increasing the sensitivity of a cancer cell to paclitaxel or Nab-paclitaxel, $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methyl, ethyl, hydroxymethyl, methoxymethyl, or 2-methoxyethyl.

In particular embodiments of the method for increasing the sensitivity of a cancer cell to paclitaxel or Nab-paclitaxel, the compound having the structure of Formula (I) is:

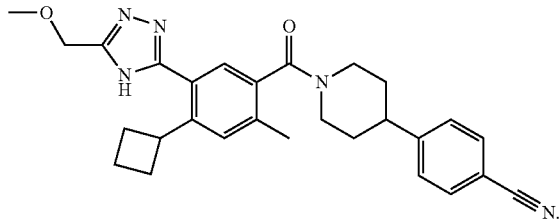

In particular embodiments of the method for increasing the sensitivity of a cancer cell to paclitaxel or Nab-paclitaxel, the compound having the structure of Formula (I) is:

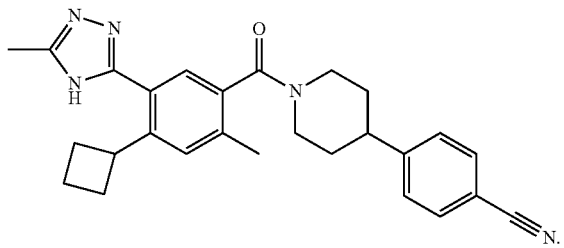 [SMILES: Cc1nnc(-c2cc(C(=O)N3CCC(c4ccc(C#N)cc4)CC3)c(C)cc2C2CCC2)[nH]1]

In particular embodiments of the method for increasing the sensitivity of a cancer cell to paclitaxel or Nab-paclitaxel, the compound having the structure of Formula (I) is:

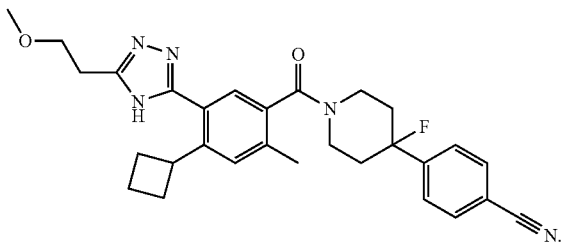 [SMILES: COCCc1nnc(-c2cc(C(=O)N3CCC(F)(c4ccc(C#N)cc4)CC3)c(C)cc2C2CCC2)[nH]1]

In particular embodiments of the method for increasing the sensitivity of a cancer cell to paclitaxel or Nab-paclitaxel, the compound having the structure of Formula (I) is:

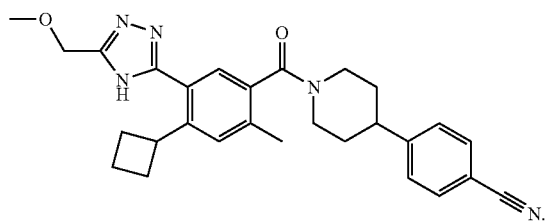 [SMILES: COCc1nnc(-c2cc(C(=O)N3CCC(c4ccc(C#N)cc4)CC3)c(C)cc2C2CCC2)[nH]1]

In particular embodiments of the method for increasing the sensitivity of a cancer cell to paclitaxel or Nab-paclitaxel, the compound having the structure of Formula (III) is:

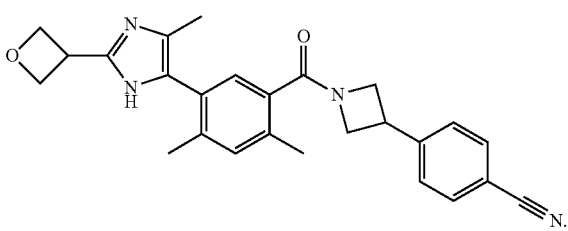 [SMILES: Cc1cc(C)c(-c2[nH]c(C3COC3)nc2C)cc1C(=O)N1CC(c2ccc(C#N)cc2)C1]

In particular embodiments of the method for increasing the sensitivity of a cancer cell to paclitaxel or Nab-paclitaxel, the fatty acid synthase inhibitor is one or more compounds, forms, and/or agents that act as an inhibitor of FASN gene expression or FASN protein activity. The choice of FASN inhibitor agents that can be co-administered with Nab-paclitaxel or paclitaxel can depend, at least in part, on the cancer being treated. In certain embodiments, Nab-paclitaxel and paclitaxel can be administered, for example with cerulenin, C75, orlistat, C93 (FAS93), FAS31, C247, GSK837149A, platensimycin, EGCG, luteolin, taxifolin, kaempferol, quercetin, apigenin, catchin, soy protein, and oleic acid, or the like.

In particular embodiments of the method for increasing the sensitivity of a cancer cell to paclitaxel or Nab-paclitaxel, the cancer cell is selected from the group consisting of a lung cancer cell, a breast cancer cell, an ovarian cancer cell, a prostate cancer cell, a colon cancer cell, and a pancreatic cancer cell. In a particular embodiment, the cancer cell is a lung cancer cell. In a particular embodiment, the cancer cell is a breast cancer cell. In a particular embodiment, the cancer cell is an ovarian cancer cell. In a particular embodiment, the cancer cell is a prostate cancer cell. In a particular embodiment, the cancer cell is a colon cancer cell. In a particular embodiment, the cancer cell is a pancreatic cancer cell.

In particular embodiments, the administration of a fatty acid synthase inhibitor increases the sensitivity of the cancer to paclitaxel or Nab-paclitaxel by about 2 to 6 fold. In particular embodiments, the administration of a fatty acid synthase inhibitor increases the sensitivity of the cancer to paclitaxel or Nab-paclitaxel by about 2 fold. In particular embodiments, the administration of a fatty acid synthase inhibitor increases the sensitivity of the cancer to paclitaxel or Nab-paclitaxel by about 3 fold. In particular embodiments, the administration of a fatty acid synthase inhibitor increases the sensitivity of the cancer to paclitaxel or Nab-paclitaxel by about 4 fold. In particular embodiments, the administration of a fatty acid synthase inhibitor increases the sensitivity of the cancer to paclitaxel or Nab-paclitaxel by about 5 fold. In particular embodiments, the administration of a fatty acid synthase inhibitor increases the sensitivity of the cancer to paclitaxel or Nab-paclitaxel by about 6 fold.

In some embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to paclitaxel or Nab-paclitaxel by about 2 to 6 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to paclitaxel or Nab-paclitaxel by about 2 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to paclitaxel or Nab-paclitaxel by about 3 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to paclitaxel or Nab-paclitaxel by about 4 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to paclitaxel or Nab-paclitaxel by about 5 fold. In particular embodiments, the administration of a compound of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX) increases the sensitivity of the cancer to paclitaxel or Nab-paclitaxel by about 6 fold.

In particular embodiments, the administration of a compound of Formula (I), Formula (II), or Formula (III) increases the sensitivity of the cancer to paclitaxel or Nab-paclitaxel by about 2 to 6 fold. In particular embodiments, the administration of a compound of Formula (I), Formula (II), or Formula (III) increases the sensitivity of the cancer to paclitaxel or Nab-paclitaxel by about 2 fold. In particular embodiments, the administration of a compound of Formula (I), Formula (II), or Formula (III) increases the sensitivity of the cancer to paclitaxel or Nab-paclitaxel by about 3 fold. In particular embodiments, the administration of a compound of Formula (I), Formula (II), or Formula (III) increases the sensitivity of the cancer to paclitaxel or Nab-paclitaxel by about 4 fold. In particular embodiments, the administration of a compound of Formula (I), Formula (II), or Formula (III) increases the sensitivity of the cancer to paclitaxel or Nab-paclitaxel by about 5 fold. In particular embodiments, the administration of a compound of Formula (I), Formula (II), or Formula (III) increases the sensitivity of the cancer to paclitaxel or Nab-paclitaxel by about 6 fold.

In particular embodiments of the method of the method for increasing the sensitivity of a cancer cell to paclitaxel or Nab-paclitaxel, the fatty acid synthase inhibitor is administered simultaneously with Nab-paclitaxel or paclitaxel. In particular embodiments, the fatty acid synthase inhibitor and Nab-paclitaxel or paclitaxel are administered simultaneously as a single pharmaceutical composition. In particular embodiments, the fatty acid synthase inhibitor and Nab-paclitaxel or paclitaxel are administered simultaneously as separate dosage forms, of the method for increasing the sensitivity of a cancer cell to paclitaxel or Nab-paclitaxel, the fatty acid synthase inhibitor is administered before Nab-paclitaxel or paclitaxel is administered. In particular embodiments of the method for increasing the sensitivity of a cancer cell to paclitaxel or Nab-paclitaxel, the fatty acid synthase inhibitor is administered after Nab-paclitaxel or paclitaxel is administered.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a taxane-resistant tumor or cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a taxane-resistant tumor in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a taxane-resistant cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a taxane-resistant tumor or cancer in a subject in need thereof.

Another aspect of the present invention relates to the use of a fatty acid synthase inhibitor compound of any one of Formula (I), (II), (II), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a taxane-resistant tumor in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a taxane-resistant cancer in a subject in need thereof.

Another aspect of the present invention relates to the use of a fatty acid synthase inhibitor compound of any one of Formula (I), (II), (III), (IV), (V), (VI), (VII), (VIII), (IX), (X)

(XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a taxane-resistant tumor or cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a taxane-resistant tumor in a subject in need thereof.

Another aspect of the present invention relates to the use of a fatty acid synthase inhibitor compound of any one of Formula (I), (II), (II), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a taxane-resistant cancer in a subject in need thereof.

In another aspect, the present invention relates to the use of a fatty acid synthase inhibitor compound of any one of Formula (I), (II), (II), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for enhancing the activity of a taxane in treating a tumor or a cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for increasing the sensitivity of a cancer cell to a taxane in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a docetaxel-resistant tumor or cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a docetaxel-resistant tumor in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a docetaxel-resistant cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a docetaxel-resistant tumor or cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a docetaxel-resistant tumor in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a docetaxel-resistant cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a docetaxel-resistant tumor or cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a docetaxel-resistant tumor in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a docetaxel-resistant cancer in a subject in need thereof.

Another aspect of the present invention relates to the use of a fatty acid synthase inhibitor compound of any one of Formula (I), (II), (II), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for enhancing the activity of docetaxel in treating a tumor or a cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for increasing the sensitivity of a cancer cell to docetaxel in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a cabazitaxel-resistant tumor or cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a cabazitaxel-resistant tumor in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a cabazitaxel-resistant cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a cabazitaxel-resistant tumor or cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a cabazitaxel-resistant tumor in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a cabazitaxel-resistant cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a cabazitaxel-resistant tumor or cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a cabazitaxel-resistant tumor in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a cabazitaxel-resistant cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for enhancing the activity of cabazitaxel in treating a tumor or a cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for increasing the sensitivity of a cancer cell to cabazitaxel in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a paclitaxel- or Nab-paclitaxel-resistant tumor or cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a paclitaxel- or Nab-paclitaxel-resistant tumor in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating or preventing a paclitaxel- or Nab-paclitaxel-resistant cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a paclitaxel- or Nab-paclitaxel-resistant tumor or cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a paclitaxel- or Nab-paclitaxel-resistant tumor in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for treating a paclitaxel- or Nab-paclitaxel-resistant cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for preventing a paclitaxel- or Nab-paclitaxel-resistant tumor or cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVI), or (XXIX), or a pharmaceutically acceptable salt thereof, in the manufacture of a medicament for preventing a paclitaxel- or Nab-paclitaxel-resistant tumor in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVI), or (XXIX), or a pharmaceutically acceptable salt thereof, in the manufacture of a medicament for preventing a paclitaxel- or Nab-paclitaxel-resistant cancer in a subject in need thereof.

Another aspect of the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for enhancing the activity of paclitaxel or Nab-paclitaxel in treating a tumor or a cancer in a subject in need thereof.

In another aspect, the present invention relates to the use of a fatty acid synthase inhibitor compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, in the manufacture of a medicament for increasing the sensitivity of a cancer cell to paclitaxel or Nab-paclitaxel in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a taxane-resistant tumor or cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a taxane-resistant tumor in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a taxane-resistant cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a taxane-resistant tumor or cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a taxane-resistant tumor in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXIII), (XXIII), (XXIV), (XXV), (XXVI), (XXVII), (XXVIII), or (XXIX), or a pharmaceutically acceptable salt thereof, for use in a method of treating a taxane-resistant cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a taxane-resistant tumor or cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a taxane-resistant tumor in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a taxane-resistant or cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method for enhancing the activity of a taxane in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method for increasing the sensitivity of a cancer cell to a taxane in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a docetaxel-resistant tumor or cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a docetaxel-resistant tumor in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a docetaxel-resistant cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a docetaxel-resistant tumor or cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a docetaxel-resistant tumor in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a docetaxel-resistant cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a docetaxel-resistant tumor or cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a docetaxel-resistant tumor in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a docetaxel-resistant cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method for enhancing the activity of docetaxel in a subject in need thereof.

In another aspect, the present invention relates to a compound of any one of Formula (I), (II) (III), (IV), (V), (VI), (VII), (VIII), (IX), (X) (XI), (XII), (XIII), (XIV), (XV), (XVI), (XVII), (XVIII), (XIX), (XX), (XXI), (XXIII), (XXIII), (XXIV), (XXV), (XXVI), (XXVII), (XXVIII), or (XXIX), or a pharmaceutically acceptable salt thereof, for use in a method for increasing the sensitivity of a cancer cell to docetaxel in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXIII), (XXIII), (XXIV), (XXV), (XXVI), (XXVII), (XXVIII), or (XXIX), or a pharmaceutically acceptable salt thereof, for use in a method of treating or preventing a cabazitaxel-resistant tumor or cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a cabazitaxel-resistant tumor in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a cabazitaxel-resistant cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a cabazitaxel-resistant tumor or cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a cabazitaxel-resistant tumor in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a cabazitaxel-resistant cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a cabazitaxel-resistant tumor or cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a cabazitaxel-resistant tumor in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a cabazitaxel-resistant cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method for enhancing the activity of cabazitaxel in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method for increasing the sensitivity of a cancer cell to cabazitaxel in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a paclitaxel- or Nab-paclitaxel-resistant tumor or cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a paclitaxel- or Nab-paclitaxel-resistant tumor in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating or preventing a paclitaxel- or Nab-paclitaxel-resistant cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a paclitaxel- or Nab-paclitaxel-resistant tumor or cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a paclitaxel- or Nab-paclitaxel-resistant tumor in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of treating a paclitaxel- or Nab-paclitaxel-resistant cancer in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a paclitaxel- or Nab-paclitaxel-resistant tumor or cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a paclitaxel- or Nab-paclitaxel-resistant tumor in a subject in need thereof.

In another aspect, the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method of preventing a paclitaxel- or Nab-paclitaxel-resistant cancer in a subject in need thereof.

Another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method for enhancing the activity of paclitaxel or Nab-paclitaxel in a subject in need thereof.

In another aspect of the present invention relates to a compound of any one of Formula (I), (II), (III), (IV), (V), (VI), (VII), (VIII), (IX), (X) (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), or (XXIX), or a pharmaceutically acceptable salt thereof, for use in a method for increasing the sensitivity of a cancer cell to paclitaxel or Nab-paclitaxel in a subject in need thereof.

Formulations, Routes of Administration, and Effective Doses

For the purposes of administration, the compounds of the present invention may be administered to a patient or subject as a raw chemical or may be formulated as pharmaceutical compositions. Pharmaceutical compositions of the present invention generally comprise a compound of the invention and a pharmaceutically acceptable carrier, diluent or excipient. The compound is present in the composition in an amount which is effective to treat a particular disease or condition of interest, as described herein, and preferably with acceptable toxicity to the patient. The activity of compounds can be determined by one skilled in the art, for example, as described in the Examples below. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate. Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

The frequency of administration of the compounds and compositions described herein may vary from once-a-day (QD) to twice-a-day (BID) or thrice-a-day (TID), etc., the precise frequency of administration varying with, for example, the patient's condition, the dosage, etc.

EXAMPLES

The following Examples illustrate various representative methods of making compounds of this invention, i.e., compounds of Formula (I), Formula (II), or Formula (III), or a stereoisomer, prodrug or pharmaceutically acceptable salt thereof. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich. Lancaster Synthesis, Inc., Maybridge, Matrix Scientific, TCI, and Fluorochem USA, etc, or synthesized according to sources known to those skilled in the art (see, e.g., Advanced Organic Chemistry: Reactions, Mechanisms, and Structure, 5th edition (Wiley, December 2000)) or prepared as described in this invention.

The following examples are provided for purposes of illustration, not limitation.

Examples 1-4

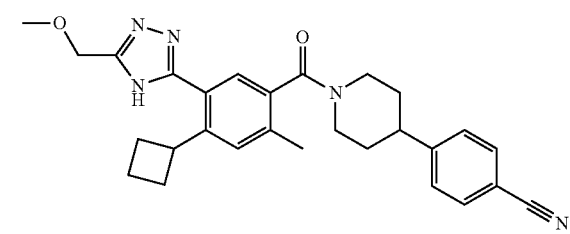

1

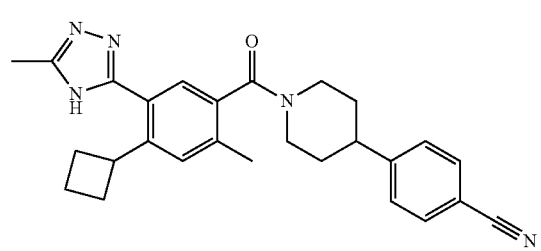

2

3

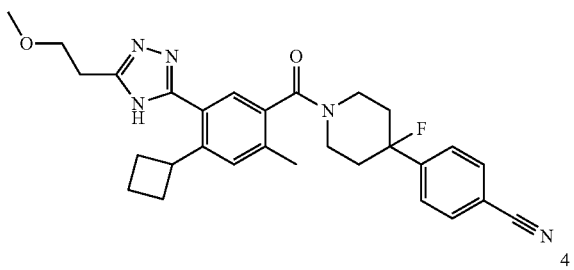

4

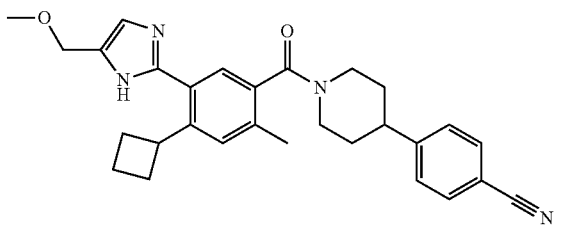

The compounds of Formula (I) in general and compounds 1-4, specifically, are disclosed in US 2012/0264737, which is incorporated herein in its entirety.

Example 5

5

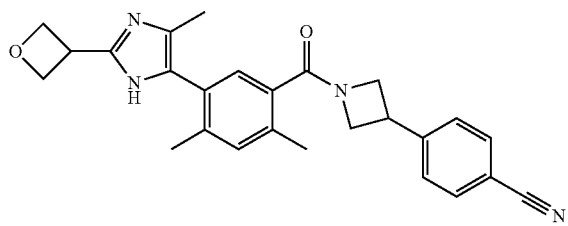

The compounds of Formula (II) and Formula (III) in general and compound 5, specifically, are disclosed in WO 2014/008197, which is incorporated herein in its entirety.

The compounds of Formula (IV)-(XXIX) in general and compound are disclosed in WO 2015/105860, which is incorporated herein in its entirety.

Example 6

FASN Inhibition in Combination with Nab-paclitaxel Induces Sensitivity to Paclitaxel in Paclitaxel Resistant Tumor Cell Lines For drug treatment, MIA PaCa-2 or BxPC-3 cells were plated in ⅜-well plates in RPMI medium plus 10% FBS. Parental (paclitaxel sensitive) or AbR (paclitaxel resistant) variants of the MIA PaCa-2 or BxPC-3 cell lines were used. Compound 5 was prepared in DMSO and further diluted 1:10 in RPMI medium for addition to the assay solution at a final concentration of either 0.2 or 2.0 µM. Serial dilutions of Nab-paclitaxel were prepared in DMSO and further diluted 1:10 in RPMI medium for addition to the assay solution. RPMI-diluted compounds were added to each well 24-hours after cell plating. Assays were done in triplicate for each drug concentration, with cell viability measured at 3 or 7 days after compound addition. The number of viable cells was measured using the CellTiter-Glo assay (Promega) according to the manufactures instructions. Luminosity per well was determined and the signal intensity was analyzed versus drug concentration. For each FASN inhibitor, the concentration of drug resulting in 50% inhibition of the maximum signal was determined, and this value was reported as the $IC_{50}$.

Compound 2 was tested in an in-vitro model of paclitaxel-resistant pancreatic cancer to evaluate whether FASN inhibition can reverse resistance in tumor cells with acquired drug resistance. Compound 2 or DMSO was added to MIA PaCa-2 or BxPC-3 pancreatic cancer cells at either 0.2 or 2.0 µM. A 3-fold serial-dilution dose response of Nab-paclitaxel was added to the cells 1 hour after Compound 2 addition. In the paclitaxel resistant cells (AbR), Compound 2 shifted the Nab-paclitaxel $IC_{50}$ value between 2.2 and 3.1 fold. The Nab-paclitaxel $IC_{50}$ value was not significantly affected in the parental (paclitaxel sensitive) cell lines. Compound 2 shifted the BxPC-3 Nab-paclitaxel $IC_{50}$ value 2.2 fold. Similarly, the MIA PaCa-2 Nab-paclitaxel $IC_{50}$ value was shifted 3.1 fold (Table 1).

TABLE 1

Compound 2 induces paclitaxel sensitivity in pancreatic tumor cell lines with paclitaxel acquired-resistance.

| Cell Line Name | Compound 2 Concentration (µM) | 3-Day $IC_{50}$ (µM) | 3-Day $IC_{50}$ Ratio + Compound 2 |
|---|---|---|---|
| BxPC3 Parental | 0 | 2.0E−09 | 1.00 |
| BxPC3 Parental | 0.2 | 2.1E−09 | 0.93 |
| BxPC3 Parental | 2.0 | 3.0E−09 | 0.65 |
| BxPC3 AbR | 0 | 9.0E−08 | 1.00 |
| BxPC3 AbR | 0.2 | 8.8E−08 | 1.02 |
| BxPC3 AbR | 2.0 | 4.2E−08 | 2.16 |
| MIA PaCa-2 Parental | 0 | 1.4E−09 | 1.00 |
| MIA PaCa-2 Parental | 0.2 | 1.3E−09 | 1.04 |
| MIA PaCa-2 Parental | 2.0 | 1.3E−09 | 1.08 |
| MIA PaCa-2 AbR | 0 | 5.2E−07 | 1.00 |
| MIA PaCa-2 AbR | 0.2 | 3.2E−07 | 1.62 |
| MIA PaCa-2 AbR | 2.0 | 1.7E−07 | 3.12 |

Compound 5 was tested in an in-vitro model of paclitaxel-resistant pancreatic cancer to evaluate whether FASN inhibition can reverse resistance in tumor cells with acquired drug resistance. Compound 5 or DMSO was added to MIA PaCa-2 or BxPC-3 pancreatic cancer cells at either 0.2 or 2.0 µM. A 3-fold serial-dilution dose response of Nab-paclitaxel was added to the cells 1 hour after Compound 5 addition. In the paclitaxel resistant cells (AbR), Compound 5 shifted the Nab-paclitaxel $IC_{50}$ value between 2.7 and 5.6 fold. The Nab-paclitaxel $IC_{50}$ value was not significantly affected in the parental (paclitaxel sensitive) cell lines. Compound 5 shifted the BxPC-3 Nab-paclitaxel $IC_{50}$ value 4.0 and 5.6 fold. Similarly, the MIA PaCa-2 Nab-paclitaxel $IC_{50}$ value was shifted 2.7 and 3.4 fold (Table 2). When BxPC-3 cells are treated with Nab-paclitaxel and Compound 5 in the presence of 50 µM exogenous palmitate (the product of FASN) the $IC_{50}$ value is not shifted (Table 3) demonstrating that Compound 5 is acting through inhibition of FASN to sensitize the cells to Nab-paclitaxel.

TABLE 2

| | Compound 5 Concentration (μM) | 3-Day IC$_{50}$ (μM) | 3-Day IC$_{50}$ Ratio + Compound 5 | 7-Day IC$_{50}$ (μM) | 7-Day IC$_{50}$ Ratio + Compound 5 |
|---|---|---|---|---|---|
| Cell Line Name | | | | | |
| BxPC3 Parental | 0 | 4.39E−03 | 1.00 | 7.89E−03 | 1.00 |
| BxPC3 Parental | 0.2 | 4.77E−03 | 0.92 | 1.30E−02 | 0.61 |
| BxPC3 Parental | 2.0 | 6.96E−03 | 0.63 | 1.25E−02 | 0.63 |
| BxPC3 AbR | 0 | 6.40E−01 | 1.00 | 3.01E−01 | 1.00 |
| BxPC3 AbR | 0.2 | 4.39E−01 | 1.46 | 2.34E−01 | 1.29 |
| BxPC3 AbR | 2.0 | 1.15E−01 | 5.57 | 7.57E−02 | 3.98 |
| MIA PaCa-2 Parental | 0 | 8.45E−10 | 1.00 | 1.09E−08 | 1.00 |
| MIA PaCa-2 Parental | 0.2 | 7.14E−10 | 1.18 | 9.99E−09 | 1.09 |
| MIA PaCa-2 Parental | 2.0 | 5.33E−10 | 1.59 | 5.80E−09 | 1.88 |
| MIA PaCa-2 AbR | 0 | 3.09E−07 | 1.00 | 7.45E−07 | 1.00 |
| MIA PaCa-2 AbR | 0.2 | 2.12E−07 | 1.46 | 7.15E−07 | 1.04 |
| MIA PaCa-2 AbR | 2.0 | 1.13E−07 | 2.73 | 2.21E−07 | 3.37 |

Compound 5 induces paclitaxel sensitivity in pancreatic tumor cell lines with paclitaxel acquired-resistance.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating a taxane-resistant tumor or cancer in a subject, the method comprising administering to the subject in need thereof a therapeutically effective amount of:
   (i) a fatty acid synthase inhibitor having the structure of:

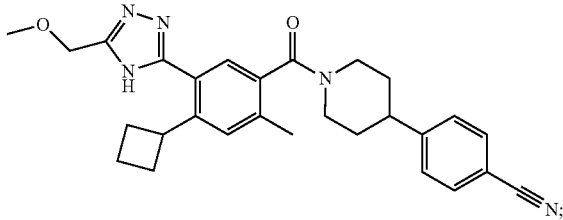 [SMILES: COCc1nnc(-c2cc(C(=O)N3CCC(c4ccc(C#N)cc4)CC3)c(C)cc2C2CCC2)[nH]1]

and
   (ii) a taxane.

2. The method of claim 1 wherein the taxane-resistant cancer is lung cancer.

3. The method of claim 1 wherein the taxane-resistant cancer is breast cancer.

4. The method of claim 1 wherein the taxane-resistant cancer is ovarian cancer.

5. The method of claim 1 wherein the taxane-resistant cancer is prostate cancer.

6. The method of claim 1 wherein the taxane-resistant cancer is colon cancer.

7. The method of claim 1 wherein the taxane-resistant cancer is pancreatic cancer.

8. The method of claim 1 wherein the fatty acid synthase inhibitor is administered simultaneously with the taxane.

9. The method of claim 8 wherein the fatty acid synthase inhibitor and the taxane are administered simultaneously as a single pharmaceutical composition.

10. The method of claim 8 wherein the fatty acid synthase inhibitor and the taxane are administered simultaneously as separate dosage forms.

11. The method of claim 1 wherein the fatty acid synthase inhibitor is administered before the taxane is administered.

12. The method of claim 1 wherein the fatty acid synthase inhibitor is administered after the taxane is administered.

13. The method of claim 1, wherein the taxane-resistant tumor is resistant to paclitaxel.

14. The method of claim 1, wherein the taxane-resistant tumor is resistant to Nab-paclitaxel.

15. The method of claim 1, wherein the taxane is paclitaxel.

16. The method of claim 1, wherein the taxane is Nab-paclitaxel.

17. The method of claim 1, wherein the taxane is docetaxel.

18. The method of claim 1, wherein the taxane is cabazitaxel.

19. The method of claim 1, wherein the taxane-resistant tumor is resistant to cabazitaxel.

20. The method of claim 1, wherein the taxane-resistant tumor is resistant to docetaxel.

* * * * *

UNITED STATES PATENT AND TRADEMARK OFFICE
CERTIFICATE OF CORRECTION

PATENT NO. : 10,363,249 B2
APPLICATION NO. : 15/503809
DATED : July 30, 2019
INVENTOR(S) : Timothy Sean Heuer Page 1 of 1

It is certified that error appears in the above-identified patent and that said Letters Patent is hereby corrected as shown below:

In the Claims

At Column 179, Claim number 1, beginning at Line number 38:

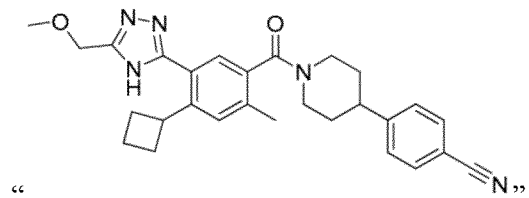

"

Should read:

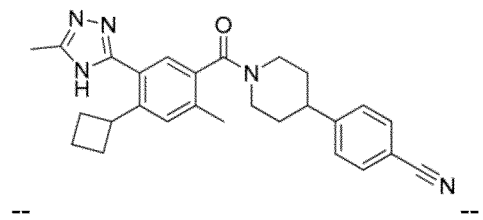

--                                                                        --

Signed and Sealed this
Seventeenth Day of September, 2019

Andrei Iancu
*Director of the United States Patent and Trademark Office*